US011400156B2

(12) United States Patent
Sagi et al.

(10) Patent No.: US 11,400,156 B2
(45) Date of Patent: *Aug. 2, 2022

(54) METHODS OF PREVENTING SECONDARY INFECTIONS

(71) Applicant: Yeda Research and Development Co. Ltd., Rehovot (IL)

(72) Inventors: Irit Sagi, Rehovot (IL); Dalit Talmi-Frank, Rehovot (IL); Inna Solomonov, Rehovot (IL); Ido Amit, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 55 days.

This patent is subject to a terminal disclaimer.

(21) Appl. No.: 16/830,461

(22) Filed: Mar. 26, 2020

(65) Prior Publication Data

US 2020/0261577 A1 Aug. 20, 2020

Related U.S. Application Data

(63) Continuation of application No. 15/549,161, filed as application No. PCT/IL2016/050156 on Feb. 9, 2016, now Pat. No. 10,610,588.

(60) Provisional application No. 62/113,551, filed on Feb. 9, 2015.

(51) Int. Cl.

| | |
|---|---|
| ***A61K 39/395*** | (2006.01) |
| ***A61K 31/215*** | (2006.01) |
| ***C07K 16/40*** | (2006.01) |
| ***A61K 45/06*** | (2006.01) |
| ***A61K 39/00*** | (2006.01) |
| ***A61K 39/215*** | (2006.01) |
| ***A61K 31/196*** | (2006.01) |
| ***A61K 31/351*** | (2006.01) |

(52) U.S. Cl.

CPC ........ *A61K 39/3955* (2013.01); *A61K 31/196* (2013.01); *A61K 31/215* (2013.01); *A61K 31/351* (2013.01); *A61K 39/215* (2013.01); *A61K 45/06* (2013.01); *C07K 16/40* (2013.01); *A61K 2039/505* (2013.01)

(58) Field of Classification Search

CPC ........... A61K 2039/5256; A61K 35/13; A61K 39/0011; A61K 39/3955; A61K 2300/00; A61K 2039/505; A61K 31/196; A61K 38/00; C12N 9/6491; A61P 11/00; A61P 31/00; A61P 31/04

See application file for complete search history.

(56) References Cited

U.S. PATENT DOCUMENTS

| | | | | |
|---|---|---|---|---|
| 7,910,620 B2 * | 3/2011 | Broadhurst, III .. | A61K 31/7056 514/451 |
| 10,610,588 B2 * | 4/2020 | Sagi ..................... | A61K 31/196 |
| 2003/0036560 A1 | 2/2003 | Sonis et al. | |
| 2018/0028650 A1 | 2/2018 | Sagi et al. | |

FOREIGN PATENT DOCUMENTS

| | | |
|---|---|---|
| JP | 2018-507847 | 3/2018 |
| WO | WO 2004/064728 | 8/2004 |
| WO | WO 2004/103364 | 12/2004 |
| WO | WO 2015/031654 | 3/2015 |
| WO | WO 2016/128975 | 8/2016 |

OTHER PUBLICATIONS

Notice of Reason(s) for Rejection dated Sep. 28, 2021 From the Japan Patent Office Re. Application No. 2020-177658. (4 Pages).
Advisory Action Before the Filing of an Appeal Brief dated Jun. 21, 2019 From the US Patent and Trademark Office Re. U.S. Appl. No. 15/549,161. ( 2 pages).
Notice of Reasons for Refusal dated Dec. 16, 2019 From the Japan Patent Office Re. Application No. 2017-541661 and Its Translation Into English. (8 Pages).
Official Action dated Oct. 5, 2018 From the US Patent and Trademark Office Re. U.S. Appl. No. 15/549,161. (19 Pages).
Official Action dated Aug. 9, 2019 From the US Patent and Trademark Office Re. U.S. Appl. No. 15/549,161. (4 Pages).
Official Action dated Feb. 26, 2019 From the US Patent and Trademark Office Re. U.S. Appl. No. 15/549,161. (5 Pages).
Restriction Official Action dated Jun. 27, 2018 From the US Patent and Trademark Office Re. U.S. Appl. No. 15/549,161. (10 pages).
Zarrabi et al. "Inhibition of Matrix Metalloproteinase 14 (MMP-14)-Mediated Cancer Cell Migration", The Journal of Biological Chemistry, 286(38): 33167-33177, Published Online Jul. 27, 2011.
International Preliminary Report on Patentability dated Aug. 24, 2017 From the International Bureau of WIPO Re. Application No. PCT/2016/050156. (9 Pages).
International Search Report and the Written Opinion dated Apr. 14, 2016 From the International Searching Authority Re. Application No. PCT/IL2016/050156.
Supplementary European Search Report and the European Search Opinion dated May 29, 2018 From the European Patent Office Re. Application No. 16748836.0. (10 Pages).

(Continued)

*Primary Examiner* — Bao Q Li

(57) ABSTRACT

A method of treating or preventing a disease associated with a secondary infection in a subject infected with a pathogen is provided. The method comprises administering to the subject a therapeutically effective amount of an anti-pathogenic agent directed towards the pathogen and a therapeutically effective amount of an agent which down-regulates at least one extracellular matrix-associated polypeptide.

10 Claims, 22 Drawing Sheets
(15 of 22 Drawing Sheet(s) Filed in Color)
Specification includes a Sequence Listing.

(56) References Cited

OTHER PUBLICATIONS

Abdulkhalek et al. "Neul Sialidase and Matrix Metalloproteinase-9 Cross-Talk is Essential for Toll-Like Rceptor Activation and Cellular Signaling", The Journal of Biological Chemistry, 286(42): 36532-36549, Published Online Aug. 26, 2011.

Chow et al. "Acute Actions and Novel Targets of Matrix Metalloproteinases in the Heart and Vasculature", British Journal of Pharmacology, 152(2): 189-205, Published Online Jun. 25, 2007.

Devy et al. "New Strategies for the Next Generation of Matrix-Metalloproteinase Inhibitors: Selectively Targeting Membrane-Anchored MMPs With Therapeutic Antibodies", Biochemistry Research International, 2011: 1-11, Published Online Oct. 28, 2010.

Elkington et al. "The Paradox of Matrix Metalloproteinases in Infectious Disease", Clinical and Experimental Immunology, XP008146400, 142(1): 12-20, Published Online Jun. 16, 2005. p. 13, col. 2, Para 3—p. 15, col. 2, Para 3. Fig. 1, p. 16, col. 2, Para 2—p. 17, col. 1, Para 1.

Fujita et al. "Doxycycline Attenuated Lung Injury by Its Biological Effect Apart From Its Antimicrobial Function", Pulmonary Pharmacology & Therapeutics, 20(6): 669-675, Published Online Sep. 14, 2007. p. 669, Last Para, p. 670, 2nd Para, p. 673, 1st Para, Figs.2, 4.

Leib et al. "Inhibition of Matrix Metalloproteinases and Tumour Necrosis Factor Alpha Converting Enzyme as Adjuvant Therapy in Pneumococcal Meningitis", Brain, XP055476051, 124(9): 1734-1742, Sep. 2001. Abstract, p. 1734-1741.

Musher et al. "Resistance of *Streptococcus pneumoniae* to the Macrolides, Azalides, Lincosamines, and Ketolides", UpToDate, Written, Reprint, 3 P., Dec. 31, 2007. Introduction.

Ng et al. "Doxycycline Treatment Attenuates Acute Lung Injury in Mice Infected With Virulent Influenza H3N2 Virus: Involvement of Matrix Metalloproteinases", Experimental and Molecular Pathology, XP028423891, 92(3): 287-295, Available Online Mar. 7, 2012. Abstract, p. 288, 1st and 2nd Para, Result Section. p. 294, 2nd Para, p. 294, col. 1, Para 2, Last Para.

Renckens et al. "Matrix Metalloproteinase-9 Deficiencv Impairs Host Defense Against Abdominal Sepsis". The Journal of Immunology, 176(6): 3735-3741, Mar. 15, 2006.

Sagi "Tissue and Extracellular Remodelling/MMPs", 41st Lorne Conference on Protein Structure and Function 2016, Lorne, Victoria, Australia, Feb. 7-11, 2016, Oral Presentation, # 02, Feb. 7, 2016.

Talmi-Frank et al. "Controlling Extra Cellular Degradation Rescues Tissue Phenotypes During Influenza Infection", ILANIT Meeting, Elat, Israel, Poster, Feb. 10-13, 2014.

Udi et al. "Inhibition Mechanism of Membrane Metalloproteinase by An Exosite-Swiveling Conformational Antibody", Structure. 23(1): 104-115, Published Online Dec. 4, 2014.

Udi et al. "Novel Inhibition Mechanism of Membrane Metalloproteinase by an Exosite-Swiveling Conformational Antibody", Supplemental Information. Structure, 23(1): 1-18, Published Online Dec. 4, 2014.

Vandenbroucke et al. "Is There New Hope for Therapeutic Matrix Metalloproteinase Inhibition?", Nature Reviews Drug Discovery, 13(12): 904-927, Published Online Nov. 7, 2014. p. 8, 2nd Para , 2 Last Para, p. 9, Right Line, 2nd Para, p. 10, 1st Para—p. 13, Left col. 2nd Para, Tables 1, 2, Fig.3.

Vanlaere et al. "Matrix Metalloproteinases as Drug Targets in Infections Caused by Gram-Negative Bacteria and in Septic Shock", Clinical Microbiology Reviews, 22(2): 224-239, Apr. 2009.

Communication Pursuant to Article 94(3) EPC dated Jul. 15, 2020 From the European Patent Office Re. Application No. 16748836.0. (11 Pages).

Translation dated Oct. 26, 2021 of Notice of Reason for Rejection dated Sep. 28, 2021 From the Japan Patent Office Re. Application No. 2020-177658. (4 Pages).

Examination Report dated Sep. 10, 2021 From the Servico Publico Federal, Ministerio da Economia, Institute Nacional da Propriedade Industrial do Brasil RE Application No. BR11 2017 017115 5 and its Summary Into English. (7 Pages).

* cited by examiner

Control
Vehicle/ Control Ab
Influenza
Anti-MT1-MMP (-1)
Time (days) -1 0 1 2 3 4 5 6 7 8 9 10 11 12

Control
Vehicle
Control Ab
Anti-MT1-MMP Ab
Alveoli
Bronchi

Wall thickness
Wall thickness (μm)
0 2 4 6 8
***
***
Control Vehicle Control Ab Anti-MT1-MMP Cell number
Number of cells per FOV
0 20 40 60 80 100
***
***
Control Vehicle Control Ab Anti-MT1-MMP

SEQUENCE LISTING

```
<160> NUMBER OF SEQ ID NOS: 55

<210> SEQ ID NO 1
<211> LENGTH: 931
<212> TYPE: DNA
<213> ORGANISM: homo sapiens

<400> SEQUENCE: 1

tttcgtcggc ccgccccttg gcttctgcac tgatggtggg tggatgagta atgcatccag     60

gaagcctgga ggcctgtggt ttccgcaccc gctgccaccc ccgcccctag cgtggacatt    120

tatcctctag cgctcaggcc ctgccgccat cgccgcagat ccagcgccca gagagacacc    180

agagaaccca ccatggcccc ctttgagccc ctggcttctg gcatcctgtt gttgctgtgg    240

ctgatagccc ccagcagggc ctgcacctgt gtcccacccc acccacagac ggccttctgc    300

aattccgacc tcgtcatcag ggccaagttc gtggggacac cagaagtcaa ccagaccacc    360

ttataccagc gttatgagat caagatgacc aagatgtata aagggttcca agccttaggg    420

gatgccgctg acatccggtt cgtctacacc cccgccatgg agagtgtctg cggatacttc    480

cacaggtccc acaaccgcag cgaggagttt ctcattgctg gaaaactgca ggatggactc    540

ttgcacatca ctacctgcag ttttgtggct ccctggaaca gcctgagctt agctcagcgc    600

cggggcttca ccaagaccta cactgttggc tgtgaggaat gcacagtgtt tccctgttta    660

tccatcccct gcaaactgca gagtggcact cattgcttgt ggacggacca gctcctccaa    720

ggctctgaaa agggcttcca gtcccgtcac cttgcctgcc tgcctcggga gccagggctg    780

tgcacctggc agtccctgcg gtcccagata gcctgaatcc tgcccggagt ggaagctgaa    840

gcctgcacag tgtccaccct gttcccactc ccatctttct tccggacaat gaaataaaga    900

gttaccaccc agcagaaaaa aaaaaaaaaa a                                   931

<210> SEQ ID NO 2
<211> LENGTH: 4410
<212> TYPE: DNA
<213> ORGANISM: homo sapiens

<400> SEQUENCE: 2

ggggagaacc cacagggaga cccacagaca catatgcacg agagagacag aggaggaaag     60

agacagagac aaaggcacag cggaagaagg cagagacagg gcaggcacag aagcggccca    120

gacagagtcc tacagaggga gaggccagag aagctgcaga agacacaggc agggagagac    180

aaagatccag gaaaggaggg ctcaggagga gagtttggag aagccagacc cctgggcacc    240
```

```
tctcccaagc ccaaggacta agttttctcc atttccttta acggtcctca gcccttctga    300
aaactttgcc tctgaccttg gcaggagtcc aagcccccag gctacagaga ggagctttcc    360
aaagctaggg tgtggaggac ttggtgccct agacggcctc agtccctccc agctgcagta    420
ccagtgccat gtcccagaca ggctcgcatc ccgggagggg cttggcaggg cgctggctgt    480
ggggagccca accctgcctc ctgctcccca ttgtgccgct ctcctggctg gtgtggctgc    540
ttctgctact gctggcctct ctcctgccct cagcccggct ggccagcccc ctcccccggg    600
aggaggagat cgtgtttcca gagaagctca acggcagcgt cctgcctggc tcgggcgccc    660
ctgccaggct gttgtgccgc ttgcaggcct ttggggagac gctgctacta gagctggagc    720
aggactccgg tgtgcaggtc gaggggctga cagtgcagta cctgggccag gcgcctgagc    780
tgctgggtgg agcagagcct ggcacctacc tgactggcac catcaatgga gatccggagt    840
cggtggcatc tctgcactgg gatgggggag ccctgttagg cgtgttacaa tatcgggggg    900
ctgaactcca cctccagccc ctggagggag gcacccctaa ctctgctggg ggacctgggg    960
ctcacatcct acgccggaag agtcctgcca gcggtcaagg tcccatgtgc aacgtcaagg   1020
ctcctcttgg aagccccagc cccagacccc gaagagccaa gcgctttgct tcactgagta   1080
gatttgtgga gacactggtg gtggcagatg acaagatggc cgcattccac ggtgcggggc   1140
taaagcgcta cctgctaaca gtgatggcag cagcagccaa ggccttcaag cacccaagca   1200
tccgcaatcc tgtcagcttg gtggtgactc ggctagtgat cctggggtca ggcgaggagg   1260
ggccccaagt ggggcccagt gctgcccaga ccctgcgcag cttctgtgcc tggcagcggg   1320
gcctcaacac ccctgaggac tcggaccctg accactttga cacagccatt ctgtttaccc   1380
gtcaggacct gtgtggagtc tccacttgcg acacgctggg tatggctgat gtgggcaccg   1440
tctgtgaccc ggctcggagc tgtgccattg tggaggatga tgggctccag tcagccttca   1500
ctgctgctca tgaactgggt catgtcttca acatgctcca tgacaactcc aagccatgca   1560
tcagtttgaa tgggcctttg agcacctctc gccatgtcat ggcccctgtg atggctcatg   1620
tggatcctga ggagccctgg tccccctgca gtgcccgctt catcactgac ttcctggaca   1680
atggctatgg gcactgtctc ttagacaaac cagaggctcc attgcatctg cctgtgactt   1740
tccctggcaa ggactatgat gctgaccgcc agtgccagct gaccttcggg cccgactcac   1800
gccattgtcc acagctgccg ccgccctgtg ctgccctctg gtgctctggc cacctcaatg   1860
gccatgccat gtgccagacc aaacactcgc cctgggccga tggcacaccc tgcgggcccg   1920
cacaggcctg catgggtggt cgctgcctcc acatggacca gctccaggac ttcaatattc   1980
cacaggctgg tggctggggt ccttggggac catggggtga ctgctctcgg acctgtgggg   2040
gtggtgtcca gttctcctcc cgagactgca cgaggcctgt cccccggaat ggtggcaagt   2100
actgtgaggg ccgccgtacc cgcttccgct cctgcaacac tgaggactgc ccaactggct   2160
cagccctgac cttccgcgag gagcagtgtg ctgcctacaa ccaccgcacc gacctcttca   2220
agagcttccc agggcccatg gactgggttc ctcgctacac aggcgtggcc ccccaggacc   2280
agtgcaaact cacctgccag gcccaggcac tgggctacta ctatgtgctg gagccacggg   2340
tggtagatgg gacccccctgt tccccggaca gctcctcggt ctgtgtccag ggccgatgca   2400
tccatgctgg ctgtgatcgc atcattggct ccaagaagaa gtttgacaag tgcatggtgt   2460
gcggagggga cggttctggt tgcagcaagc agtcaggctc cttcaggaaa ttcaggtacg   2520
gatacaacaa tgtggtcact atccccgcgg gggccaccca cattcttgtc cggcagcagg   2580
gaaaccctgg ccaccggagc atctacttgg ccctgaagct gccagatggc tcctatgccc   2640
```

```
tcaatggtga atacacgctg atgccctccc ccacagatgt ggtactgcct ggggcagtca   2700

gcttgcgcta cagcggggcc actgcagcct cagagacact gtcaggccat gggccactgg   2760

cccagccttt gacactgcaa gtcctagtgg ctggcaaccc ccaggacaca cgcctccgat   2820

acagcttctt cgtgccccgg ccgacccctt caacgccacg ccccactccc caggactggc   2880

tgcaccgaag agcacagatt ctggagatcc ttcggcggcg cccctgggcg ggcaggaaat   2940

aacctcacta tcccggctgc cctttctggg caccggggcc tcggacttag ctgggagaaa   3000

gagagagctt ctgttgctgc ctcatgctaa gactcagtgg ggaggggctg tgggcgtgag   3060

acctgcccct cctctctgcc ctaatgcgca ggctggccct gccctggttt cctgccctgg   3120

gaggcagtga tgggttagtg gatggaaggg gctgacagac agccctccat ctaaactgcc   3180

ccctctgccc tgcgggtcac aggagggagg gggaaggcag ggagggcctg ggccccagtt   3240

gtatttattt agtatttatt cacttttatt tagcaccagg gaaggggaca aggactaggg   3300

tcctggggaa cctgacccct gacccctcat agccctcacc ctggggctag gaaatccagg   3360

gtggtggtga taggtataag tggtgtgtgt atgcgtgtgt gtgtgtgtga aaatgtgtgt   3420

gtgcttatgt atgaggtaca acctgttctg ctttcctctt cctgaatttt atttttttggg   3480

aaaagaaaag tcaagggtag ggtgggcctt cagggagtga gggattatct tttttttttt   3540

ttctttcttt ctttcttttt tttttttgag acagaatctc gctctgtcgc ccaggctgga   3600

gtgcaatggc acaatctcgg ctcactgcat cctccgcctc ccgggttcaa gtgattctca   3660

tgcctcagcc tcctgagtag ctgggattac aggctcctgc caccacgccc ggctaatttt   3720

tgttttgttt tgtttggaga cagagtctcg ctattgtcac cagggctgga atgatttcag   3780

ctcactgcaa ccttcgccac ctgggttcca gcaattctcc tgcctcagcc tcccgagtag   3840

ctgagattat aggcacctac caccacgccc ggctaatttt tgtattttta gtagagacgg   3900

ggtttcacca tgttggccag gctggtctcg aactcctgac cttaggtgat ccactcgcct   3960

tcatctccca aagtgctggg attacaggcg tgagccaccg tgcctggcca cgcccaacta   4020

atttttgtat ttttagtaga gacagggttt caccatgttg gccaggctgc tcttgaactc   4080

ctgacctcag gtaatcgacc tgcctcggcc tcccaaagtg ctgggattac aggtgtgagc   4140

caccacgccc ggtacatatt ttttaaattg aattctacta tttatgtgat ccttttggag   4200

tcagacagat gtggttgcat cctaactcca tgtctctgag cattagattt ctcatttgcc   4260

aataataata cctcccttag aagtttgttg tgaggattaa ataatgtaaa taaagaacta   4320

gcataacact caaaaaaaaa aaaaaaaaaa aaaaaaaaaa aaaaaaaaaa aaaaaaaaaa   4380

aaaaaaaaaa aaaaaaaaaa aaaaaaaaaa                                    4410
```

<210> SEQ ID NO 3
<211> LENGTH: 8605
<212> TYPE: DNA
<213> ORGANISM: homo sapiens

<400> SEQUENCE: 3

```
aattcgccaa ctgaaaaagt gggaaaggat gtctggaggc gaggcgtccc attacagagg     60

aaggagctcg ctatataagc cagccaaagt tggctgcacc ggccacagcc tgcctactgt    120

cacccgcctc tcccgcgcgc agatacacgc ccccgcctcc gtgggcacaa aggcagcgct    180

gctggggaac tcgggggaac gcgcacgtgg gaaccgccgc agctccacac tccaggtact    240

tcttccaagg acctaggtct ctcgcccatc ggaaagaaaa taattctttc aagaagatca    300
```

```
gggacaactg atttgaagtc tactctgtgc ttctaaatcc ccaattctgc tgaaagtgag    360
ataccctaga gccctagagc cccagcagca cccagccaaa cccacctcca ccatgggggc    420
catgactcag ctgttggcag gtgtctttct tgctttcctt gccctcgcta ccgaaggtgg    480
ggtcctcaag aaagtcatcc ggcacaagcg acagagtggg gtgaacgcca ccctgccaga    540
agagaaccag ccagtggtgt ttaaccacgt ttacaacatc aagctgccag tgggatccca    600
gtgttcggtg gatctggagt cagccagtgg ggagaaagac ctggcaccgc cttcagagcc    660
cagcgaaagc tttcaggagc acacagtgga tggggaaaac cagattgtct tcacacatcg    720
catcaacatc ccccgccggg cctgtggctg tgccgcagcc cctgatgtta aggagctgct    780
gagcagactg gaggagctgg agaacctggt gtcttccctg agggagcaat gtactgcagg    840
agcaggctgc tgtctccagc ctgccacagg ccgcttggac accaggccct tctgtagcgg    900
tcggggcaac ttcagcactg aaggatgtgg ctgtgtctgc gaacctggct ggaaaggccc    960
caactgctct gagcccgaat gtccaggcaa ctgtcacctt cgaggccggt gcattgatgg   1020
gcagtgcatc tgtgacgacg gcttcacggg cgaggactgc agccagctgg cttgccccag   1080
cgactgcaat gaccagggca agtgcgtaaa tggagtctgc atctgtttcg aaggctacgc   1140
cggggctgac tgcagccgtg aaatctgccc agtgccctgc agtgaggagc acggcacatg   1200
tgtagatggc ttgtgtgtgt gccacgatgg ctttgcaggc gatgactgca acaagcctct   1260
gtgtctcaac aattgctaca accgtggacg atgcgtggag aatgagtgcg tgtgtgatga   1320
gggtttcacg ggcgaagact gcagtgagct catctgcccc aatgactgct tcgaccgggg   1380
ccgctgcatc aatggcacct gctactgcga agaaggcttc acaggtgaag actgcgggaa   1440
acccacctgc ccacatgcct gccacaccca gggccggtgt gaggaggggc agtgtgtatg   1500
tgatgagggc tttgccggtg tggactgcag cgagaagagg tgtcctgctg actgtcacaa   1560
tcgtggccgc tgtgtagacg ggcggtgtga gtgtgatgat ggtttcactg gagctgactg   1620
tggggagctc aagtgtccca atggctgcag tggccatggc cgctgtgtca atgggcagtg   1680
tgtgtgtgat gagggctata ctggggagga ctgcagccag ctacggtgcc ccaatgactg   1740
tcacagtcgg ggccgctgtg tcgagggcaa atgtgtatgt gagcaaggct tcaagggcta   1800
tgactgcagt gacatgagct gccctaatga ctgtcaccag cacggccgct gtgtgaatgg   1860
catgtgtgtt tgtgatgacg gctacacagg ggaagactgc cgggatcgcc aatgccccag   1920
ggactgcagc aacaggggcc tctgtgtgga cggacagtgc gtctgtgagg acggcttcac   1980
cggccctgac tgtgcagaac tctcctgtcc aaatgactgc catggccagg gtcgctgtgt   2040
gaatgggcag tgcgtgtgcc atgaaggatt tatgggcaaa gactgcaagg agcaaagatg   2100
tcccagtgac tgtcatggcc agggccgctg cgtggacggc cagtgcatct gccacgaggg   2160
cttcacaggc ctggactgtg gccagcactc ctgccccagt gactgcaaca acttaggaca   2220
atgcgtctcg ggccgctgca tctgcaacga gggctacagc ggagaagact gctcagaggt   2280
gtctcctccc aaagacctcg ttgtgacaga agtgacggaa gagacggtca acctggcctg   2340
ggacaatgag atgcgggtca cagagtacct tgtcgtgtac acgcccaccc acgagggtgg   2400
tctggaaatg cagttccgtg tgcctgggga ccagacgtcc accatcatcc aggagctgga   2460
gcctggtgtg gagtacttta tccgtgtatt tgccatcctg gagaacaaga agagcattcc   2520
tgtcagcgcc agggtggcca cgtacttacc tgcacctgaa ggcctgaaat tcaagtccat   2580
caaggagaca tctgtggaag tggagtggga tcctctagac attgcttttg aaacctggga   2640
gatcatcttc cggaatatga ataaagaaga tgagggagag atcaccaaaa gcctgaggag   2700
```

gccagagacc tcttaccggc aaactggtct agctcctggg caagagtatg agatatctct 2760
gcacatagtg aaaaacaata cccggggccc tggcctgaag agggtgacca ccacacgctt 2820
ggatgccccc agccagatcg aggtgaaaga tgtcacagac accactgcct tgatcacctg 2880
gttcaagccc ctggctgaga tcgatggcat tgagctgacc tacggcatca aagacgtgcc 2940
aggagaccgt accaccatcg atctcacaga ggacgagaac cagtactcca tcgggaacct 3000
gaagcctgac actgagtacg aggtgtccct catctcccgc agaggtgaca tgtcaagcaa 3060
cccagccaaa gagaccttca caacaggcct cgatgctccc aggaatcttc gacgtgtttc 3120
ccagacagat aacagcatca ccctggaatg gaggaatggc aaggcagcta ttgacagtta 3180
cagaattaag tatgccccca tctctggagg ggaccacgct gaggttgatg ttccaaagag 3240
ccaacaagcc acaaccaaaa ccacactcac aggtctgagg ccgggaactg aatatgggat 3300
tggagtttct gctgtgaagg aagacaagga gagcaatcca gcgaccatca acgcagccac 3360
agagttggac acgcccaagg accttcaggt ttctgaaact gcagagacca gcctgaccct 3420
gctctggaag acaccgttgg ccaaatttga ccgctaccgc ctcaattaca gtctccccac 3480
aggccagtgg gtgggagtgc agcttccaag aaacaccact tcctatgtcc tgagaggcct 3540
ggaaccagga caggagtaca atgtcctcct gacagccgag aaaggcagac acaagagcaa 3600
gcccgcacgt gtgaaggcat ccactgaaca agcccctgag ctggaaaacc tcaccgtgac 3660
tgaggttggc tgggatggcc tcagactcaa ctggaccgca gctgaccagg cctatgagca 3720
ctttatcatt caggtgcagg aggccaacaa ggtggaggca gctcggaacc tcaccgtgcc 3780
tggcagcctt cgggctgtgg acataccggg cctcaaggct gctacgcctt atacagtctc 3840
catctatggg gtgatccagg gctatagaac accagtgctc tctgctgagg cctccacagg 3900
ggaaactccc aatttgggag aggtcgtggt ggccgaggtg ggctgggatg ccctcaaact 3960
caactggact gctccagaag ggcctatga gtactttttc attcaggtgc aggaggctga 4020
cacagtagag gcagcccaga acctcaccgt cccaggagga ctgaggtcca cagacctgcc 4080
tgggctcaaa gcagccactc attataccat caccatccgc ggggtcactc aggacttcag 4140
cacaacccct ctctctgttg aagtcttgac agaggaggtt ccagatatgg gaaacctcac 4200
agtgaccgag gttagctggg atgctctcag actgaactgg accacgccag atggaaccta 4260
tgaccagttt actattcagg tccaggaggc tgaccaggtg gaagaggctc acaatctcac 4320
ggttcctggc agcctgcgtt ccatggaaat cccaggcctc agggctggca ctccttacac 4380
agtcaccctg cacggcgagg tcaggggcca cagcactcga ccccttgctg tagaggtcgt 4440
cacagaggat ctcccacagc tgggagattt agccgtgtct gaggttggct gggatggcct 4500
cagactcaac tggaccgcag ctgacaatgc ctatgagcac tttgtcattc aggtgcagga 4560
ggtcaacaaa gtggaggcag cccagaacct cacgttgcct ggcagcctca gggctgtgga 4620
catcccgggc ctcgaggctg ccacgcctta tagagtctcc atctatgggg tgatccgggg 4680
ctatagaaca ccagtactct ctgctgaggc ctccacagcc aaagaacctg aaattggaaa 4740
cttaaatgtt tctgacataa ctcccgagag cttcaatctc tcctggatgg ctaccgatgg 4800
gatcttcgag acctttacca ttgaaattat tgattccaat aggttgctgg agactgtgga 4860
atataatatc tctggtgctg aacgaactgc ccatatctca gggctacccc ctagtactga 4920
ttttattgtc tacctctctg gacttgctcc cagcatccgg accaaaacca tcagtgccac 4980
agccacgaca gaggccctgc cccttctgga aaacctaacc atttccgaca ttaatcccta 5040

```
cgggttcaca gtttcctgga tggcatcgga gaatgccttt gacagctttc tagtaacggt   5100
ggtggattct gggaagctgc tggaccccca ggaattcaca ctttcaggaa cccagaggaa   5160
gctggagctt agaggcctca taactggcat tggctatgag gttatggtct ctggcttcac   5220
ccaagggcat caaaccaagc ccttgagggc tgagattgtt acagaagccg aaccggaagt   5280
tgacaacctt ctggtttcag atgccacccc agacggtttc cgtctgtcct ggacagctga   5340
tgaaggggtc ttcgacaatt ttgttctcaa aatcagagat accaaaaagc agtctgagcc   5400
actggaaata accctacttg cccccgaacg taccagggac ataacaggtc tcagagaggc   5460
tactgaatac gaaattgaac tctatggaat aagcaaagga aggcgatccc agacagtcag   5520
tgctatagca acaacagcca tgggctcccc aaaggaagtc attttctcag acatcactga   5580
aaattcggct actgtcagct ggagggcacc cacagcccaa gtggagagct tccggattac   5640
ctatgtgccc attacaggag gtacaccctc catggtaact gtggacggaa ccaagactca   5700
gaccaggctg gtgaaactca tacctggcgt ggagtacctt gtcagcatca tcgccatgaa   5760
gggctttgag gaaagtgaac ctgtctcagg gtcattcacc acagctctgg atggcccatc   5820
tggcctggtg acagccaaca tcactgactc agaagccttg gccaggtggc agccagccat   5880
tgccactgtg gacagttatg tcatctccta cacaggcgag aaagtgccag aaattacacg   5940
cacggtgtcc gggaacacag tggagtatgc tctgaccgac ctcgagcctg ccacggaata   6000
cacactgaga atctttgcag agaaagggcc ccagaagagc tcaaccatca ctgccaagtt   6060
cacaacagac ctcgattctc caagagactt gactgctact gaggttcagt cggaaactgc   6120
cctccttacc tggcgacccc cccgggcatc agtcaccggt tacctgctgg tctatgaatc   6180
agtggatggc acagtcaagg aagtcattgt gggtccagat accacctcct acagcctggc   6240
agacctgagc ccatccaccc actacacagc caagatccag gcactcaatg ggcccctgag   6300
gagcaatatg atccagacca tcttcaccac aattggactc ctgtacccct tccccaagga   6360
ctgctcccaa gcaatgctga atggagacac gacctctggc ctctacacca tttatctgaa   6420
tggtgataag gctgaggcgc tggaagtctt ctgtgacatg acctctgatg gggggtggatg   6480
gattgtgttc ctgagacgca aaaacggacg cgagaacttc taccaaaact ggaaggcata   6540
tgctgctgga tttggggacc gcagagaaga attctggctt gggctggaca acctgaacaa   6600
aatcacagcc caggggcagt acgagctccg ggtggacctg cgggaccatg gggagacagc   6660
ctttgctgtc tatgacaagt tcagcgtggg agatgccaag actcgctaca agctgaaggt   6720
ggaggggtac agtgggacag caggtgactc catggcctac cacaatggca gatccttctc   6780
cacctttgac aaggacacag attcagccat caccaactgt gctctgtcct acaaaggggc   6840
tttctggtac aggaactgtc accgtgtcaa cctgatgggg agatatgggg acaataacca   6900
cagtcagggc gttaactggt tccactggaa gggccacgaa cactcaatcc agtttgctga   6960
gatgaagctg agaccaagca acttcagaaa tcttgaaggc aggcgcaaac gggcataaat   7020
tccagggacc actgggtgag agaggaataa ggcccagagc gaggaaagga ttttaccaaa   7080
gcatcaatac aaccagccca accatcggtc cacacctggg catttggtga gagtcaaagc   7140
tgaccatgga tccctggggc caacggcaac agcatgggcc tcacctcctc tgtgatttct   7200
ttctttgcac caaagacatc agtctccaac atgtttctgt tttgttgttt gattcagcaa   7260
aaatctccca gtgacaacat cgcaatagtt ttttacttct cttaggtggc tctgggaatg   7320
ggagaggggt aggatgtaca ggggtagttt gttttagaac cagccgtatt ttacatgaag   7380
ctgtataatt aattgtcatt atttttgtta gcaaagatta aatgtgtcat tggaagccat   7440
```

ccctttttt acatttcata caacagaaac cagaaaagca atactgtttc cattttaagg 7500
atatgattaa tattattaat ataataatga tgatgatgat gatgaaaact aaggattttt 7560
caagagatct ttctttccaa aacatttctg gacagtacct gattgtattt ttttttaaa 7620 taaaagcaca agtacttttg agtttgttat tttgctttga attgttgagt ctgaatttca 7680
ccaaagccaa tcatttgaac aaagcgggga atgttgggat aggaaaggta agtagggata 7740
gtggtcaagt gggaggggtg gaaaggagac taaagactgg gagagaggga agcacttttt 7800
ttaaataaag ttgaacacac ttgggaaaag cttacaggcc aggcctgtaa tcccaacact 7860
ttgggaggcc aaggtgggag gatagcttaa ccccaggagt ttgagaccag cctgagcaac 7920
atagtgagaa cttgtctcta cagaaaaaaa aaaaaaaaaa aatttaatta ggcaagcgtg 7980
gtagtgcgca cctgtcgtcc cagctactca ggaggctgag gtaggaaaat cactggagcc 8040
caggagttag aggttacagt gagctatgat cacactactg cactccagcc tgggcaacag 8100
agggagaccc tgtctctaaa taaaaaaaga aaagaaaaaa aaagcttaca acttgagatt 8160
cagcatcttg ctcagtattt ccaagactaa tagattatgg tttaaaagat gcttttatac 8220
tcattttcta atgcaactcc tagaaactct atgatatagt tgaggtaagt attgttacca 8280
cacatgggct aagatcccca gaggcagact gcctgagttc aattcttggc tccaccattc 8340
ccaagttccc taacctctct atgcctcagt ttcctcttct gtaaagtagg gacactcata 8400
cttctcattt cagaacattt ttgtgaagaa taaattatgt tatccatttg aggcccttag 8460
aatggtaccc ggtgtatatt aagtgctagt acatgttagc tatcatcatt atcactttat 8520
atgagatgga ctggggttca tagaaaccca atgacttgat tgtggctact actcaataaa 8580
taatagaatt tggatttaaa aaaaa 8605

<210> SEQ ID NO 4
<211> LENGTH: 4193
<212> TYPE: DNA
<213> ORGANISM: homo sapiens

<400> SEQUENCE: 4
cttcttctcg ctgagtctcc tcctcggctc tgacggtaca gtgatataat gatgatgggt 60
gtcacaaccc gcatttgaac ttgcaggcga gctgccccga gcctttctgg ggaagaactc 120
caggcgtgcg gacgcaacag ccgagaacat taggtgttgt ggacaggagc tgggaccaag 180
atcttcggcc agccccgcat cctcccgcat cttccagcac cgtcccgcac cctccgcatc 240
cttccccggg ccaccacgct tcctatgtga cccgcctggg caacgccgaa cccagtcgcg 300
cagcgctgca gtgaattttc cccccaaact gcaataagcc gccttccaag gccaagatgt 360
tcataaatat aaagagcatc ttatggatgt gttcaacctt aatagtaacc catgcgctac 420
ataaagtcaa agtgggaaaa agcccaccgg tgaggggctc cctctctgga aaagtcagcc 480
taccttgtca tttttcaacg atgcctactt tgccacccag ttacaacacc agtgaatttc 540
tccgcatcaa atggtctaag attgaagtgg acaaaaatgg aaaagatttg aaagagacta 600
ctgtccttgt ggcccaaaat ggaaatatca agattggtca ggactacaaa gggagagtgt 660
ctgtgcccac acatcccgag gctgtgggcg atgcctccct cactgtggtc aagctgctgg 720
caagtgatgc gggtctttac cgctgtgacg tcatgtacgg gattgaagac acacaagaca 780
cggtgtcact gactgtggat ggggttgtgt ttcactacag ggcggcaacc agcaggtaca 840
cactgaattt tgaggctgct cagaaggctt gtttggacgt tggggcagtc atagcaactc 900

-continued

```
cagagcagct ctttgctgcc tatgaagatg gatttgagca gtgtgacgca ggctggctgg    960
ctgatcagac tgtcagatat cccatccggg ctcccagagt aggctgttat ggagataaga   1020
tgggaaaggc aggagtcagg acttatggat tccgttctcc ccaggaaact tacgatgtgt   1080
attgttatgt ggatcatctg gatggtgatg tgttccacct cactgtcccc agtaaattca   1140
ccttcgagga ggctgcaaaa gagtgtgaaa accaggatgc caggctggca acagtggggg   1200
aactccaggc ggcatggagg aacggctttg accagtgcga ttacgggtgg ctgtcggatg   1260
ccagcgtgcg ccaccctgtg actgtggcca gggcccagtg tggaggtggt ctacttgggg   1320
tgagaaccct gtatcgtttt gagaaccaga caggcttccc tccccctgat agcagatttg   1380
atgcctactg ctttaaacga cctgatcgct gcaaaatgaa cccgtgcctt aacggaggca   1440
cctgttatcc tactgaaact tcctacgtat gcacctgtgt gccaggatac agcggagacc   1500
agtgtgaact tgattttgat gaatgtcact ctaatccctg tcgtaatgga gccacttgtg   1560
ttgatggttt taacacattc aggtgcctct gccttccaag ttatgttggt gcactttgtg   1620
agcaagatac cgagacatgt gactatggct ggcacaaatt ccaagggcag tgctacaaat   1680
actttgccca tcgacgcaca tgggatgcag ctgaacggga atgccgtctg cagggtgccc   1740
atctcacaag catcctgtct cacgaagaac aaatgtttgt taatcgtgtg ggccatgatt   1800
atcagtggat aggcctcaat gacaagatgt ttgagcatga cttccgttgg actgatggca   1860
gcacactgca atacgagaat tggagaccca accagccaga cagcttcttt tctgctggag   1920
aagactgtgt tgtaatcatt tggcatgaga atggccagtg gaatgatgtt ccctgcaatt   1980
accatctcac ctatacgtgc aagaaaggaa cagtcgcttg cggccagccc cctgttgtag   2040
aaaatgccaa gacctttgga aagatgaaac ctcgttatga aatcaactcc ctgattagat   2100
accactgcaa agatggtttc attcaacgtc accttccaac tatccggtgc ttaggaaatg   2160
gaagatgggc tatacctaaa attacctgca tgaacccatc tgcataccaa aggacttatt   2220
ctatgaaata ctttaaaaat tcctcatcag caaaggacaa ttcaataaat acatccaaac   2280
atgatcatcg ttggagccgg aggtggcagg agtcgaggcg ctgatcccta aaatggcgaa   2340
catgtgtttt catcatttca gccaaagtcc taacttcctg tgcctttcct atcacctcga   2400
gaagtaatta tcagttggtt tggatttttg gaccaccgtt cagtcatttt gggttgccgt   2460
gctcccaaaa cattttaaat gaaagtattg gcattcaaaa agacagcaga caaaatgaaa   2520
gaaaatgaga gcagaaagta agcatttcca gcctatctaa tttctttagt tttctatttg   2580
cctccagtgc agtccatttc ctaatgtata ccagcctact gtactattta aaatgctcaa   2640
tttcagcacc gatggccatg taaataagat gatttaatgt tgattttaat cctgtatata   2700
aaataaaaag tcacaatgag tttgggcata tttaatgatg attatggagc cttagaggtc   2760
tttaatcatt ggttcggctg cttttatgta gtttaggctg gaaatggttt cacttgctct   2820
ttgactgtca gcaagactga agatggcttt tcctggacag ctagaaaaca caaaatcttg   2880
taggtcattg cacctatctc agccataggt gcagtttgct tctacatgat gctaaaggct   2940
gcgaatggga tcctgatgga actaaggact ccaatgtcga actcttcttt gctgcattcc   3000
tttttcttca cttacaagaa aggcctgaat ggaggacttt tctgtaacca ggaacatttt   3060
ttaggggtca aagtgctaat aattaactca accaggtcta ctttttaatg gctttcataa   3120
cactaactca taaggttacc gatcaatgca tttcatacgg atatagacct agggctctgg   3180
agggtggggg attgttaaaa cacatgcaaa aaaaaaaaaa aaaaaaaaaa aagaaatttt   3240
gtatatataa ccattttaat cttttataaa gttttgaatg ttcatgtatg aatgctgcag   3300
```

```
ctgtgaagca tacataaata aatgaagtaa gccatactga tttaatttat tggatgttat   3360

tttccctaag acctgaaaat gaacatagta tgctagttat ttttcagtgt tagcctttta   3420

ctttcctcac acaatttgga atcatataat ataggtactt tgtccctgat taaataatgt   3480

gacggataga atgcatcaag tgtttattat gaaaagagtg gaaaagtata tagcttttag   3540

caaaaggtgt ttgcccattc taagaaatga gcgaatatat agaaatagtg tgggcatttc   3600

ttcctgttag gtggagtgta tgtgttgaca tttctcccca tctcttccca ctctgttttc   3660

tccccattat ttgaataaag tgactgctga agatgacttt gaatccttat ccacttaatt   3720

taatgtttaa agaaaaacct gtaatggaaa gtaagactcc ttccctaatt tcagtttaga   3780

gcaacttgaa gaagagtaga caaaaaataa aatgcacata gaaaaagaga aaaagggcac   3840

aaagggattg gcccaatatt gattcttttt ttataaaacc tcctttggct tagaaggaat   3900

gactctagct acaataatac acagtatgtt taagcaggtt cccttggttg ttgcattaaa   3960

tgtaatccac ctttaggtat tttagagcac agaacaacac tgtgttgatc tagtaggttt   4020

ctatttttcc tttctcttta caatgcacat aatactttcc tgtatttata tcataacgtg   4080

tatagtgtaa aatgtgaatg actttttttg tgaatgaaaa tctaaaatct ttgtaacttt   4140

ttatatctgc ttttgtttca ccaaagaaac ctaaaatcct tcttttacta cac          4193
```

<210> SEQ ID NO 5
<211> LENGTH: 7253
<212> TYPE: DNA
<213> ORGANISM: homo sapiens

<400> SEQUENCE: 5

```
agccgctgcg cccgagctgg cctgcgagtt cagggctcct gtcgctctcc aggagcaacc     60

tctactccgg acgcacaggc attccccgcg cccctccagc cctcgccgcc ctcgccaccg    120

ctcccggccg ccgcgctccg gtacacacag gatccctgct gggcaccaac agctccacca    180

tggggctggc ctggggacta ggcgtcctgt tcctgatgca tgtgtgtggc accaaccgca    240

ttccagagtc tggcggagac aacagcgtgt ttgacatctt tgaactcacc ggggccgccc    300

gcaaggggtc tgggcgccga ctggtgaagg gccccgaccc ttccagccca gctttccgca    360

tcgaggatgc caacctgatc ccccctgtgc ctgatgacaa gttccaagac ctggtggatg    420

ctgtgcgggc agaaaagggt ttcctccttc tggcatccct gaggcagatg aagaagaccc    480

ggggcacgct gctggccctg gagcggaaag accactctgg ccaggtcttc agcgtggtgt    540

ccaatggcaa ggcgggcacc ctggacctca gcctgaccgt ccaaggaaag cagcacgtgg    600

tgtctgtgga agaagctctc ctggcaaccg gccagtggaa gagcatcacc ctgtttgtgc    660

aggaagacag ggcccagctg tacatcgact gtgaaaagat ggagaatgct gagttggacg    720

tccccatcca aagcgtcttc accagagacc tggccagcat cgccagactc cgcatcgcaa    780

agggggggcgt caatgacaat ttccaggggg tgctgcagaa tgtgaggttt gtctttggaa    840

ccacaccaga agacatcctc aggaacaaag gctgctccag ctctaccagt gtcctcctca    900

cccttgacaa caacgtggtg aatggttcca gccctgccat ccgcactaac tacattggcc    960

acaagacaaa ggacttgcaa gccatctgcg gcatctcctg tgatgagctg tccagcatgg   1020

tcctggaact caggggcctg cgcaccattg tgaccacgct gcaggacagc atccgcaaag   1080

tgactgaaga gaacaaagag ttggccaatg agctgaggcg gcctccccta tgctatcaca   1140

acggagttca gtacagaaat aacgaggaat ggactgttga tagctgcact gagtgtcact   1200
```

gtcagaactc agttaccatc tgcaaaaagg tgtcctgccc catcatgccc tgctccaatg 1260
ccacagttcc tgatggagaa tgctgtcctc gctgttggcc cagcgactct gcggacgatg 1320
gctggtctcc atggtccgag tggacctcct gttctacgag ctgtggcaat ggaattcagc 1380
agcgcggccg ctcctgcgat agcctcaaca accgatgtga gggctcctcg gtccagacac 1440
ggacctgcca cattcaggag tgtgacaaga gatttaaaca ggatggtggc tggagccact 1500
ggtccccgtg gtcatcttgt tctgtgacat gtggtgatgg tgtgatcaca aggatccggc 1560
tctgcaactc tcccagcccc cagatgaacg ggaaaccctg tgaaggcgaa gcgcgggaga 1620
ccaaagcctg caagaaagac gcctgcccca tcaatggagg ctggggtcct tggtcaccat 1680
gggacatctg ttctgtcacc tgtggaggag ggtacagaa acgtagtcgt ctctgcaaca 1740
accccacacc ccagtttgga ggcaaggact gcgttggtga tgtaacagaa aaccagatct 1800
gcaacaagca ggactgtcca attgatggat gcctgtccaa tccctgcttt gccggcgtga 1860
agtgtactag ctaccctgat ggcagctgga aatgtggtgc ttgtccccct ggttacagtg 1920
gaaatggcat ccagtgcaca gatgttgatg agtgcaaaga agtgcctgat gcctgcttca 1980
accacaatgg agagcaccgg tgtgagaaca cggaccccgg ctacaactgc ctgccctgcc 2040
ccccacgctt caccggctca cagcccttcg gccagggtgt cgaacatgcc acggccaaca 2100
aacaggtgtg caagccccgt aacccctgca cggatgggac ccacgactgc aacaagaacg 2160
ccaagtgcaa ctacctgggc cactatagcg accccatgta ccgctgcgag tgcaagcctg 2220
gctacgctgg caatggcatc atctgcgggg aggacacaga cctggatggc tggcccaatg 2280
agaacctggt gtgcgtggcc aatgcgactt accactgcaa aaaggataat tgccccaacc 2340
ttcccaactc agggcaggaa gactatgaca aggatggaat tggtgatgcc tgtgatgatg 2400
acgatgacaa tgataaaatt ccagatgaca gggacaactg tccattccat tacaacccag 2460
ctcagtatga ctatgacaga gatgatgtgg gagaccgctg tgacaactgt ccctacaacc 2520
acaacccaga tcaggcagac acagacaaca atggggaagg agacgcctgt gctgcagaca 2580
ttgatggaga cggtatcctc aatgaacggg acaactgcca gtacgtctac aatgtggacc 2640
agagagacac tgatatggat ggggttggag atcagtgtga caattgcccc ttggaacaca 2700
atccggatca gctggactct gactcagacc gcattggaga tacctgtgac aacaatcagg 2760
atattgatga agatggccac cagaacaatc tggacaactg tccctatgtg cccaatgcca 2820
accaggctga ccatgacaaa gatggcaagg gagatgcctg tgaccacgat gatgacaacg 2880
atggcattcc tgatgacaag gacaactgca gactcgtgcc caatcccgac cagaaggact 2940
ctgacggcga tggtcgaggt gatgcctgca aagatgattt tgaccatgac agtgtgccag 3000
acatcgatga catctgtcct gagaatgttg acatcagtga gaccgatttc cgccgattcc 3060
agatgattcc tctggacccc aaagggacat cccaaaatga ccctaactgg gttgtacgcc 3120
atcagggtaa agaactcgtc cagactgtca actgtgatcc tggactcgct gtaggttatg 3180
atgagtttaa tgctgtggac ttcagtggca ccttcttcat caacaccgaa agggacgatg 3240
actatgctgg atttgtcttt ggctaccagt ccagcagccg cttttatgtt gtgatgtgga 3300
agcaagtcac ccagtcctac tgggacacca accccacgag ggctcaggga tactcgggcc 3360
tttctgtgaa agttgtaaac tccaccacag ggcctggcga gcacctgcgg aacgccctgt 3420
ggcacacagg aaacacccct ggccaggtgc gcaccctgtg gcatgaccct cgtcacatag 3480
gctggaaaga tttcaccgcc tacagatggc gtctcagcca caggccaaag acgggtttca 3540
ttagagtggt gatgtatgaa gggaagaaaa tcatggctga ctcaggaccc atctatgata 3600
aaacctatgc tggtggtaga ctagggttgt ttgtcttctc tcaagaaatg gtgttcttct 3660
ctgacctgaa atacgaatgt agagatccct aatcatcaaa ttgttgattg aaagactgat 3720
cataaaccaa tgctggtatt gcaccttctg gaactatggg cttgagaaaa cccccaggat 3780
cacttctcct tggcttcctt cttttctgtg cttgcatcag tgtggactcc tagaacgtgc 3840
gacctgcctc aagaaaatgc agttttcaaa aacagactca gcattcagcc tccaatgaat 3900
aagacatctt ccaagcatat aaacaattgc tttggtttcc ttttgaaaaa gcatctactt 3960
gcttcagttg ggaaggtgcc cattccactc tgcctttgtc acagagcagg gtgctattgt 4020
gaggccatct ctgagcagtg gactcaaaag cattttcagg catgtcagag aagggaggac 4080
tcactagaat tagcaaacaa aaccaccctg acatcctcct tcaggaacac ggggagcaga 4140
ggccaaagca ctaaggggag ggcgcatacc cgagacgatt gtatgaagaa aatatggagg 4200
aactgttaca tgttcggtac taagtcattt tcaggggatt gaaagactat tgctggattt 4260
catgatgctg actggcgtta gctgattaac ccatgtaaat aggcacttaa atagaagcag 4320
gaaagggaga caaagactgg cttctggact tcctccctga tccccaccct tactcatcac 4380
ctgcagtggc cagaattagg gaatcagaat caaaccagtg taaggcagtg ctggctgcca 4440
ttgcctggtc acattgaaat tggtggcttc attctagatg tagcttgtgc agatgtagca 4500
ggaaaatagg aaaacctacc atctcagtga gcaccagctg cctcccaaag gaggggcagc 4560
cgtgcttata tttttatggt tacaatggca caaaattatt atcaacctaa ctaaaacatt 4620
ccttttctct tttttcctga attatcatgg agttttctaa ttctctcttt tggaatgtag 4680
attttttta aatgctttac gatgtaaaat atttattttt tacttattct ggaagatctg 4740
gctgaaggat tattcatgga acaggaagaa gcgtaaagac tatccatgtc atctttgttg 4800
agagtcttcg tgactgtaag attgtaaata cagattattt attaactctg ttctgcctgg 4860
aaatttaggc ttcatacgga aagtgtttga gagcaagtag ttgacattta tcagcaaatc 4920
tcttgcaaga acagcacaag gaaaatcagt ctaataagct gctctgcccc ttgtgctcag 4980
agtggatgtt atgggattct ttttttctct gttttatctt ttcaagtgga attagttggt 5040
tatccatttg caaatgtttt aaattgcaaa gaaagccatg aggtcttcaa tactgtttta 5100
ccccatccct tgtgcatatt tccagggaga aggaaagcat atacactttt ttctttcatt 5160
tttccaaaag agaaaaaaat gacaaaaggt gaaacttaca tacaaatatt acctcatttg 5220
ttgtgtgact gagtaaagaa tttttggatc aagcggaaag agtttaagtg tctaacaaac 5280
ttaaagctac tgtagtacct aaaaagtcag tgttgtacat agcataaaaa ctctgcagag 5340
aagtattccc aataaggaaa tagcattgaa atgttaaata caatttctga aagttatgtt 5400
ttttttctat catctggtat accattgctt tatttttata aattattttc tcattgccat 5460
tggaatagat atctcagatt gtgtagatat gctatttaaa taatttatca ggaaatactg 5520
cctgtagagt tagtatttct atttttatat aatgtttgca cactgaattg aagaattgtt 5580
ggtttttttct ttttttttgtt ttgttttttt tttttttttt ttttgctttt gacctcccat 5640
ttttactatt tgccaatacc tttttctagg aatgtgcttt tttttgtaca catttttatc 5700
cattttacat tctaaagcag tgtaagttgt atattactgt ttcttatgta caaggaacaa 5760
caataaatca tatggaaatt tatatttata cttactgtat ccatgcttat ttgttctcta 5820
ctggctttat gtcatgaagt atatgcgtaa ataccattca taaatcaata tagcatatac 5880
aaaaataaat tacagtaagt catagcaaca ttcacagttt gtatgtgatt gagaaagact 5940

```
gagttgctca ggcctaggct tagaatttgc tgcgtttgtg gaataaaaga acaaaatgat   6000
acattagcct gccatatcaa aaacatataa aagagaaatt atccctaagt caagggcccc   6060
cataagaata aaatttctta ttaaggtcat tagatgtcat tgaatccttt tcaaagtgca   6120
gtatgaaaac aaagggaaaa acactgaagc acacgcaact ctcacagcga cattttctga   6180
cccacgaatg atgccttggg tgggcaacac gattgcatgt tgtggagaca cttcggaagt   6240
aaatgtggat gagggaggag ctgtccttgc aatgttgagc caagcattac agatacctcc   6300
tcttgaagaa ggaataataa gtttaatcaa aaaagaagac taaaaaatgt aaaatttgga   6360
aggaatccat aaatgcgtgt gtgtctaaat acaaattatc atgtgaagaa aaggcccaag   6420
tgtaccaata agcagacctt gatttttgga tgggctaatt atgaatgtgg aatactgacc   6480
agttaatttc cagttttaat gaaaacagat caaagaagaa attttatgag taggttaaag   6540
gtctggcttt gaggtctatt aaacactaga aaggactggc tgggtgagat aaaatcttcc   6600
ttgttgattt tcactctcat tctataaata ctcatctttc tgagtagcca tgatcacata   6660
caaatgtaaa ttgccaaatc attttatagt accaaggtga agaagcagga actagaaagt   6720
gttgataata gctgtggagt taggaaaact gatgtgaagg aaataattct ttgaaatggc   6780
aaagaattaa ataccatcat tcattatcag aagagttcaa cgtttgaagt gctgggagat   6840
aattctaatt cattcttgga tagtgaagca aaactgattg aaaataccaa gataagacag   6900
aaaaagtgac tggaaagagg agcttttctt ccaggcatgt tccagtttca ccctaagact   6960
gaccttcaaa taatcaggtt gtactgaaat aaaggacttg ttaaaaatta aaattatgtc   7020
atcgagatga tagctttttt cctcctccaa cagtttattg tcatgtgttg tgggagagct   7080
cgagtgaaga gcaataaact ccaggtctta taagaatgta catacaataa aggtggtgcc   7140
agcagttttt ttttttctaa agagtcacat gtagaaaagc ctccagtatt aagctcctga   7200
attcattcct taaataaatt ggctctctct ctcttctata aaaaaaaaaa aaa          7253

<210> SEQ ID NO 6
<211> LENGTH: 2683
<212> TYPE: DNA
<213> ORGANISM: homo sapiens

<400> SEQUENCE: 6

ctgatataga gcaggcgccg cgggtcgcag cacagtgcgg agaccgcagc cccggagccc     60
gggccagggt ccacctgtcc ccgcagcgcc ggctcgcgcc ctcctgccgc agccaccgag    120
ccgccgtcta gcgccccgac ctcgccacca tgagagccct gctggcgcgc ctgcttctct    180
gcgtcctggt cgtgagcgac tccaaagtga gtgcgctctt gctttgactg atgctgccca    240
aggacctctg atcagcacca ggggagagga ggggctgctc agggagctgg ggtcctccgg    300
attccatcca cagcagggcc agactctccc caggaaatgg gacagggtgg cagcggaggc    360
ttgagaacca cgggggttgg cactggctgg caagggagga agaggccgcc gggactgccc    420
cagcctgcgg gcatctggta gatgaagctt gcttgggtca atccatttct cctggctgga    480
aacccatggt cttccatttg agaactagat acgaacaggc gaactgtgac tgtctaaatg    540
gaggaacatg tgtgtccaac aagtacttct ccaacattca ctggtgcaac tgcccaaaga    600
aattcggagg gcagcactgt gaaatagata agtcaaaaac ctgctatgag gggaatggtc    660
acttttaccg aggaaaggcc agcactgaca ccatgggccg gccctgcctg ccctggaact    720
ctgccactgt ccttcagcaa acgtaccatg cccacagatc tgatgctctt cagctgggcc    780
tggggaaaca taattactgc aggaacccag acaaccggag gcgaccctgg tgctatgtgc    840
```

```
aggtgggcct aaagccgctt gtccaagagt gcatggtgca tgactgcgca gatggaaaaa    900

agccctcctc tcctccagaa gaattaaaat ttcagtgtgg ccaaaagact ctgaggcccc    960

gctttaagat tattggggga gaattcacca ccatcgagaa ccagccctgg tttgcggcca   1020

tctacaggag gcaccggggg ggctctgtca cctacgtgtg tggaggcagc ctcatcagcc   1080

cttgctgggt gatcagcgcc acacactgct tcattgatta cccaaagaag gaggactaca   1140

tcgtctacct gggtcgctca aggcttaact ccaacacgca aggggagatg aagtttgagg   1200

tggaaaacct catcctacac aaggactaca gcgctgacac gcttgctcac cacaacgaca   1260

ttgccttgct gaagatccgt tccaaggagg gcaggtgtgc gcagccatcc cggactatac   1320

agaccatctg cctgccctcg atgtataacg atccccagtt tggcacaagc tgtgagatca   1380

ctggctttgg aaaagagaat tctaccgact atctctatcc ggagcagctg aaaatgactg   1440

ttgtgaagct gatttcccac cgggagtgtc agcagcccca ctactacggc tctgaagtca   1500

ccaccaaaat gctgtgtgct gctgacccac agtggaaaac agattcctgc cagggagact   1560

caggggggacc cctcgtctgt tccctccaag gccgcatgac tttgactgga attgtgagct   1620

ggggccgtgg atgtgccctg aaggacaagc caggcgtcta cacgagagtc tcacacttct   1680

taccctggat ccgcagtcac accaaggaag agaatggcct ggccctctga gggtccccag   1740

ggaggaaacg ggcaccaccc gctttcttgc tggttgtcat tttgcagta gagtcatctc   1800

catcagctgt aagaagagac tgggaagata ggctctgcac agatggattt gcctgtgcca   1860

cccaccaggg cgaacgacaa tagctttacc ctcaggcata ggcctgggtg ctggctgccc   1920

agacccctct ggccaggatg gaggggtggt cctgactcaa catgttactg accagcaact   1980

tgtctttttc tggactgaag cctgcaggag ttaaaaaggg cagggcatct cctgtgcatg   2040

ggtgaaggga gagccagctc cccgacggt gggcatttgt gaggcccatg gttgagaaat   2100

gaataatttc ccaattagga agtgtaacag ctgaggtctc ttgagggagc ttagccaatg   2160

tgggagcagc ggtttgggga gcagagacac taacgacttc agggcagggc tctgatattc   2220

catgaatgta tcaggaaata tatatgtgtg tgtatgtttg cacacttgtg tgtgggctgt   2280

gagtgtaagt gtgagtaaga gctggtgtct gattgttaag tctaaatatt tccttaaact   2340

gtgtggactg tgatgccaca cagagtggtc tttctggaga ggttataggt cactcctggg   2400

gcctcttggg tcccccacgt gacagtgcct gggaatgtat tattctgcag catgacctgt   2460

gaccagcact gtctcagttt cactttcaca tagatgtccc tttcttggcc agttatccct   2520

tccttttagc ctagttcatc caatcctcac tgggtggggt gaggaccact cctgtacact   2580

gaatatttat atttcactat ttttatttat atttttgtaa ttttaaataa aagtgatcaa   2640

taaaatgtga tttttctgat gacaaaaaaa aaaaaaaaaa aaa                     2683
```

<210> SEQ ID NO 7
<211> LENGTH: 2137
<212> TYPE: DNA
<213> ORGANISM: homo sapiens

<400> SEQUENCE: 7

```
cacagagagg ctgggagagc aagccggaga gaagagagag cccggccaga cccactgcga     60

tgagacagga cgcgcccaag cccactcctg cagcctgccg ctgctccggc ctggcccgga    120

gggtgctgac catcgccttc gccctgctca tcctgggcct catgacctgg gcctacgccg    180

ccggggtgcc gctggcctcc gatcgctacg gcctcctggc cttcggcctc tacggggcct    240
```

```
tcctttcagc gcacctggtg gcgcagagcc tcttcgcgta cctggagcac cggcgggtgg    300
cggcggcggc gcgggggccg ctggatgcag ccaccgcgcg cagtgtggcg ctgaccatct    360
ccgcctacca ggaggacccc gcgtacctgc gccagtgcct ggcgtccgcc cgcgccctgc    420
tgtacccgcg cgcgcggctg cgcgtcctca tggtggtgga tggcaaccgc gccgaggacc    480
tctacatggt cgacatgttc cgcgaggtct tcgctgacga ggaccccgcc acgtacgtgt    540
gggacggcaa ctaccaccag ccctgggaac ccgcggcggc gggcgcggtg ggcgccggag    600
cctatcggga ggtggaggcg gaggatcctg ggcggctggc agtggaggcg ctggtgagga    660
ctcgcaggtg cgtgtgcgtg gcgcagcgct ggggcggcaa gcgcgaggtc atgtacacag    720
ccttcaaggc gctcggagat tcggtggact acgtgcaggt ctgtgactcg gacacaaggt    780
tggaccccat ggcactgctg gagctcgtgc gggtactgga cgaggacccc cgggtagggg    840
ctgttggtgg ggacgtgcgg atccttaacc ctctggactc ctgggtcagc ttcctaagca    900
gcctgcgata ctgggtagcc ttcaatgtgg agcgggcttg tcagagctac ttccactgtg    960
tatcctgcat cagcggtcct ctaggcctat ataggaataa cctcttgcag cagtttcttg   1020
aggcctggta caaccagaag ttcctgggta cccactgtac ttttggggat gaccggcacc   1080
tcaccaaccg catgctcagc atgggttatg ctaccaagta cacctccagg tcccgctgct   1140
actcagagac gccctcgtcc ttcctgcggt ggctgagcca gcagacacgc tggtccaagt   1200
cgtacttccg tgagtggctg tacaacgcgc tctggtggca ccggcaccat gcgtggatga   1260
cctacgaggc ggtggtctcc ggcctgttcc ccttcttcgt ggcggccact gtgctgcgtc   1320
tgttctacgc gggccgccct tgggcgctgc tgtgggtgct gctgtgcgtg cagggcgtgg   1380
cactggccaa ggcggccttc gcggcctggc tgcggggctg cctgcgcatg gtgcttctgt   1440
cgctctacgc gcccctctac atgtgtggcc tcctgcctgc caagttcctg gcgctagtca   1500
ccatgaacca gagtggctgg ggcacctcgg gccggcggaa gctggccgct aactacgtcc   1560
ctctgctgcc cctggcgctc tgggcgctgc tgctgcttgg gggcctggtc cgcagcgtag   1620
cacacgaggc cagggccgac tggagcggcc cttcccgcgc agccgaggcc taccacttgg   1680
ccgcgggggc cggcgcctac gtgggctact gggtggccat gttgacgctg tactgggtgg   1740
gcgtgcggag gctttgccgg cggcggaccg gggctaccg cgtccaggtg tgagtccagc   1800
cacgcggatg ccgcctcaag ggtcttcagg ggaggccaga ggagagctgc tgggccccga   1860
gccacgaact tgctgggtgg ttctctgggc ctcagtttcc ctcctctgca aaacgagggg   1920
gtcagcccaa gattcttcag tctggactat attgggactg ggacttctgg gtctccaggg   1980
agggtattta ttggtcaggg tgtgggatct gaggagtgga gggaaagggt cctgctttct   2040
cctcgttctt atttaatctc catttctact gtgtgatcag gatgtaataa agaattttat   2100
ttattttcaa aaaaaaaaaa aaaaaaaaaa aaaaaaa                            2137
```

<210> SEQ ID NO 8
<211> LENGTH: 1629
<212> TYPE: DNA
<213> ORGANISM: homo sapiens

<400> SEQUENCE: 8

```
attcatgaaa atccactact ccagacagac ggctttggaa tccaccagct acatccagct     60
ccctgaggca gagttgagaa tggagagaat gttacctctc ctggctctgg ggctcttggc    120
ggctgggttc tgccctgctg tcctctgcca ccctaacagc ccacttgacg aggagaatct    180
gacccaggag aaccaagacc gagggacaca cgtggacctc ggattagcct ccgccaacgt    240
```

```
ggacttcgct ttcagcctgt acaagcagtt agtcctgaag gcccctgata agaatgtcat    300

cttctcccca ctgagcatct ccaccgcctt ggccttcctg tctctggggg cccataatac    360

caccctgaca gagattctca aaggcctcaa gttcaacctc acggagactt ctgaggcaga    420

aattcaccag agcttccagc acctcctgcg caccctcaat cagtccagcg atgagctgca    480

gctgagtatg ggaaatgcca tgtttgtcaa agagcaactc agtctgctgg acaggttcac    540

ggaggatgcc aagaggctgt atggctccga ggcctttgcc actgactttc aggactcagc    600

tgcagctaag aagctcatca acgactacgt gaagaatgga actaggggga aaatcacaga    660

tctgatcaag gaccttgact cgcagacaat gatggtcctg gtgaattaca tcttctttaa    720

agccaaatgg gagatgccct ttgaccccca agatactcat cagtcaaggt tctacttgag    780

caagaaaaag tgggtaatgg tgcccatgat gagtttgcat cacctgacta taccttactt    840

ccgggacgag gagctgtcct gcaccgtggt ggagctgaag tacacaggca atgccagcgc    900

actcttcatc ctccctgatc aagacaagat ggaggaagtg gaagccatgc tgctcccaga    960

gaccctgaag cggtggagag actctctgga gttcagagag ataggtgagc tctacctgcc   1020

aaagttttcc atctcgaggg actataacct gaacgacata cttctccagc tgggcattga   1080

ggaagccttc accagcaagg ctgacctgtc agggatcaca ggggccagga acctagcagt   1140

ctcccaggtg gtccataagg ctgtgcttga tgtatttgag gagggcacag aagcatctgc   1200

tgccacagca gtcaaaatca ccctcctttc tgcattagtg gagacaagga ccattgtgcg   1260

tttcaacagg cccttcctga tgatcattgt ccctacagac acccagaaca tcttcttcat   1320

gagcaaagtc accaatccca agcaagccta gagcttgcca tcaagcagtg gggctctcag   1380

taaggaactt ggaatgcaag ctggatgcct gggtctctgg gcacagcctg gcccctgtgc   1440

accgagtggc catggcatgt gtggccctgt ctgcttatcc ttggaaggtg acagcgattc   1500

cctgtgtagc tctcacatgc acaggggccc atggactctt cagtctggag ggtcctgggc   1560

ctcctgacag caataaataa tttcgttgga aaaaaaaaaa aaaaaaaaaa aaaaaaaaaa   1620

aaaaaaaaa                                                           1629
```

<210> SEQ ID NO 9
<211> LENGTH: 3207
<212> TYPE: DNA
<213> ORGANISM: homo sapiens

<400> SEQUENCE: 9

```
ggcccacaga ggagcacagc tgtgtttggc tgcagggcca agagcgctgt caagaagacc     60

cacacgcccc cctccagcag ctgaattcct gcagctcagc agccgccgcc agagcaggac    120

gaaccgccaa tcgcaaggca cctctgagaa cttcaggatg cagatgtctc cagccctcac    180

ctgcctagtc ctgggcctgg cccttgtctt tggtgaaggg tctgctgtgc accatccccc    240

atcctacgtg gcccacctgg cctcagactt cggggtgagg gtgtttcagc aggtggcgca    300

ggcctccaag gaccgcaacg tggttttctc accctatggg gtggcctcgg tgttggccat    360

gctccagctg acaacaggag gagaaaccca gcagcagatt caagcagcta tgggattcaa    420

gattgatgac aagggcatgg cccccgccct ccggcatctg tacaaggagc tcatggggcc    480

atggaacaag gatgagatca gcaccacaga cgcgatcttc gtccagcggg atctgaagct    540

ggtccagggc ttcatgcccc acttcttcag gctgttccgg agcacggtca agcaagtgga    600

cttttcagag gtggagagag ccagattcat catcaatgac tgggtgaaga cacacacaaa    660
```

-continued

```
aggtatgatc agcaacttgc ttgggaaagg agccgtggac cagctgacac ggctggtgct    720
ggtgaatgcc ctctacttca acggccagtg gaagactccc ttccccgact ccagcaccca    780
ccgccgcctc ttccacaaat cagacggcag cactgtctct gtgcccatga tggctcagac    840
caacaagttc aactatactg agttcaccac gcccgatggc cattactacg acatcctgga    900
actgccctac cacggggaca ccctcagcat gttcattgct gccccttatg aaaaagaggt    960
gcctctctct gccctcacca acattctgag tgcccagctc atcagccact ggaaaggcaa   1020
catgaccagg ctgccccgcc tcctggttct gcccaagttc tccctggaga ctgaagtcga   1080
cctcaggaag cccctagaga acctgggaat gaccgacatg ttcagacagt ttcaggctga   1140
cttcacgagt ctttcagacc aagagcctct ccacgtcgcg caggcgctgc agaaagtgaa   1200
gatcgaggtg aacgagagtg gcacggtggc ctcctcatcc acagctgtca tagtctcagc   1260
ccgcatggcc cccgaggaga tcatcatgga cagacccttc ctctttgtgg tccggcacaa   1320
ccccacagga acagtccttt tcatgggcca agtgatggaa ccctgaccct ggggaaagac   1380
gccttcatct gggacaaaac tggagatgca tcgggaaaga agaaactccg aagaaaagaa   1440
ttttagtgtt aatgactctt tctgaaggaa gagaagacat ttgccttttg ttaaaagatg   1500
gtaaaccaga tctgtctcca agaccttggc ctctccttgg aggaccttta ggtcaaactc   1560
cctagtctcc acctgagacc ctgggagaga agtttgaagc acaactccct taaggtctcc   1620
aaaccagacg gtgacgcctg cgggaccatc tggggcacct gcttccaccc gtctctctgc   1680
ccactcgggt ctgcagacct ggttcccact gaggcccttt gcaggatgga actacggggc   1740
ttacaggagc ttttgtgtgc ctggtagaaa ctatttctgt tccagtcaca ttgccatcac   1800
tcttgtactg cctgccaccg cggaggaggc tggtgacagg ccaaaggcca gtggaagaaa   1860
cacccttca tctcagagtc cactgtggca ctggccaccc ctccccagta caggggtgct   1920
gcaggtggca gagtgaatgt cccccatcat gtggcccaac tctcctggcc tggccatctc   1980
cctccccaga aacagtgtgc atgggttatt ttggagtgta ggtgacttgt ttactcattg   2040
aagcagattt ctgcttcctt ttatttttat aggaatagag gaagaaatgt cagatgcgtg   2100
cccagctctt caccccccaa tctcttggtg gggaggggtg tacctaaata tttatcatat   2160
ccttgccctt gagtgcttgt tagagagaaa gagaactact aaggaaaata atattattta   2220
aactcgctcc tagtgtttct ttgtggtctg tgtcaccgta tctcaggaag tccagccact   2280
tgactggcac acacccctcc ggacatccag cgtgacggag cccacactgc caccttgtgg   2340
ccgcctgaga ccctcgcgcc ccccgcgccc ctctttttcc ccttgatgga aattgaccat   2400
acaatttcat cctccttcag gggatcaaaa ggacggagtg gggggacaga gactcagatg   2460
aggacagagt ggtttccaat gtgttcaata gatttaggag cagaaatgca aggggctgca   2520
tgacctacca ggacagaact ttccccaatt acagggtgac tcacagccgc attggtgact   2580
cacttcaatg tgtcatttcc ggctgctgtg tgtgagcagt ggacacgtga ggggggggtg   2640
ggtgagagag acaggcagct cggattcaac taccttagat aatatttctg aaaacctacc   2700
agccagaggg tagggcacaa agatggatgt aatgcacttt gggaggccaa ggcgggagga   2760
ttgcttgagc ccaggagttc aagaccagcc tgggcaacat accaagaccc ccgtctcttt   2820
aaaaatatat atattttaaa tatacttaaa tatatatttc taatatcttt aaatatatat   2880
atatatttta aagaccaatt tatgggagaa ttgcacacag atgtgaaatg aatgtaatct   2940
aatagaagcc taatcagccc accatgttct ccactgaaaa atcctctttc tttggggttt   3000
ttctttcttt ctttttgat tttgcactgg acggtgacgt cagccatgta caggatccac   3060
```

-continued aggggtggtg tcaaatgcta ttgaaattgt gttgaattgt atgctttttc acttttgata 3120
aataaacatg taaaaatgtt tcaaaaaaat aataaaataa ataaatacga agaatatgtc 3180
aggacagtca aaaaaaaaaa aaaaaaa 3207

<210> SEQ ID NO 10
<211> LENGTH: 1906
<212> TYPE: DNA
<213> ORGANISM: homo sapiens

<400> SEQUENCE: 10
aaagcaagga tgagtcaagc tgcgggtgat ccaaacaaac actgtcactc tttaaaagct 60
gcgctcccga ggttggacct acaaggaggc aggcaagaca gcaaggcata gagacaacat 120
agagctaagt aaagccagtg gaaatgaaga gtcttccaat cctactgttg ctgtgcgtgg 180
cagtttgctc agcctatcca ttggatggag ctgcaagggg tgaggacacc agcatgaacc 240
ttgttcagaa atatctagaa aactactacg acctcaaaaa agatgtgaaa cagtttgtta 300
ggagaaagga cagtggtcct gttgttaaaa aaatccgaga aatgcagaag ttccttggat 360
tggaggtgac ggggaagctg gactccgaca ctctggaggt gatgcgcaag cccaggtgtg 420
gagttcctga tgttggtcac ttcagaacct ttcctggcat cccgaagtgg aggaaaaccc 480
accttacata caggattgtg aattatacac cagatttgcc aaaagatgct gttgattctg 540
ctgttgagaa agctctgaaa gtctgggaag aggtgactcc actcacattc tccaggctgt 600
atgaaggaga ggctgatata atgatctctt ttgcagttag agaacatgga gacttttacc 660
cttttgatgg acctggaaat gttttggccc atgcctatgc ccctgggcca gggattaatg 720
gagatgccca ctttgatgat gatgaacaat ggacaaagga tacaacaggg accaatttat 780
ttctcgttgc tgctcatgaa attggccact ccctgggtct ctttcactca gccaacactg 840
aagctttgat gtacccactc tatcactcac tcacagacct gactcggttc cgcctgtctc 900
aagatgatat aaatggcatt cagtccctct atggacctcc ccctgactcc cctgagaccc 960
ccctggtacc cacggaacct gtccctccag aacctgggac gccagccaac tgtgatcctg 1020
ctttgtcctt tgatgctgtc agcactctga ggggagaaat cctgatcttt aaagacaggc 1080
acttttggcg caaatccctc aggaagcttg aacctgaatt gcatttgatc tcttcatttt 1140
ggccatctct tccttcaggc gtggatgccg catatgaagt tactagcaag gacctcgttt 1200
tcatttttaa aggaaatcaa ttctgggcta tcagaggaaa tgaggtacga gctggatacc 1260
caagaggcat ccacacccta ggtttccctc caaccgtgag gaaaatcgat gcagccattt 1320
ctgataagga aaagaacaaa acatatttct ttgtagagga caaatactgg agatttgatg 1380
agaagagaaa ttccatggag ccaggctttc ccaagcaaat agctgaagac tttccaggga 1440
ttgactcaaa gattgatgct gtttttgaag aatttgggtt cttttatttc tttactggat 1500
cttcacagtt ggagtttgac ccaaatgcaa agaaagtgac acacactttg aagagtaaca 1560
gctggcttaa ttgttgaaag agatatgtag aaggcacaat atgggcactt taaatgaagc 1620
taataattct tcacctaagt ctctgtgaat tgaaatgttc gttttctcct gcctgtgctg 1680
tgactcgagt cacactcaag ggaacttgag cgtgaatctg tatcttgccg gtcattttta 1740
tgttattaca gggcattcaa atgggctgct gcttagcttg caccttgtca catagagtga 1800
tctttcccaa gagaagggga agcactcgtg tgcaacagac aagtgactgt atctgtgtag 1860
actatttgct tatttaataa agacgatttg tcagttattt tatctt 1906

<210> SEQ ID NO 11
<211> LENGTH: 5676
<212> TYPE: DNA
<213> ORGANISM: homo sapiens

<400> SEQUENCE: 11
atgcttctgc tgggcatcct aaccctggct ttcgccgggc gaaccgctgg aggctctgag 60
ccagagcggg aggtagtcgt tcccatccga ctggacccgg acattaacgg ccgccgctac 120
tactggcggg gtcccgagga ctccggggat cagggactca tttttcagat cacagcattt 180
caggaggact tttacctaca cctgacgccg gatgctcagt tcttggctcc cgccttctcc 240
actgagcatc tgggcgtccc cctccagggg ctcaccgggg gctcttcaga cctgcgacgc 300
tgcttctatt ctggggacgt gaacgccgag ccggactcgt tcgctgctgt gagcctgtgc 360
ggggggctcc gcggagcctt tggctaccga ggcgccgagt atgtcattag cccgctgccc 420
aatgctagcg cgccggcggc gcagcgcaac agccagggcg cacaccttct ccagcgccgg 480
ggtgttccgg gcgggccttc cggagacccc acctctcgct gcggggtggc ctcgggctgg 540
aaccccgcca tcctacgggc cctggaccct tacaagccgc ggcgggcggg cttcggggag 600
agtcgtagcc ggcgcaggtc tgggcgcgcc aagcgtttcg tgtctatccc gcggtacgtg 660
gagacgctgg tggtcgcgga cgagtcaatg gtcaagttcc acggcgcgga cctggaacat 720
tatctgctga cgctgctggc aacggcggcg cgactctacc gccatcccag catcctcaac 780
cccatcaaca tcgttgtggt caaggtgctg cttcttagag atcgtgactc cgggcccaag 840
gtcaccggca atgcggccct gacgctgcgc aacttctgtg cctggcagaa gaagctgaac 900
aaagtgagtg acaagcaccc cgagtactgg gacactgcca tcctcttcac caggcaggac 960
ctgtgtggag ccaccacctg tgacaccctg ggcatggctg atgtgggtac catgtgtgac 1020
cccaagagaa gctgctctgt cattgaggac gatgggcttc catcagcctt caccactgcc 1080
cacgagctgg gccacgtgtt caacatgccc catgacaatg tgaaagtctg tgaggaggtg 1140
tttgggaagc tccgagccaa ccacatgatg tccccgaccc tcatccagat cgaccgtgcc 1200
aacccctggt cagcctgcag tgctgccatc atcaccgact tcctggacag cgggcacggt 1260
gactgcctcc tggaccaacc cagcaagccc atctccctgc ccgaggatct gccgggcgcc 1320
agctacaccc tgagccagca gtgcgagctg gcttttggcg tgggctccaa gccctgtcct 1380
tacatgcagt actgcaccaa gctgtggtgc accgggaagg ccaagggaca gatggtgtgc 1440
cagacccgcc acttcccctg ggccgatggc accagctgtg gcgagggcaa gctctgcctc 1500
aaaggggcct gcgtggagag acacaacctc aacaagcaca gggtggatgg ttcctgggcc 1560
aaatgggatc cctatggccc ctgctcgcgc acatgtggtg ggggcgtgca gctggccagg 1620
aggcagtgca ccaaccccac ccctgccaac gggggcaagt actgcgaggg agtgagggtg 1680
aaataccgat cctgcaatct ggagccctgc cccagctcag cctccggaaa gagcttccgg 1740
gaggagcagt gtgaggcttt caacggctac aaccacagca ccaaccggct cactctcgcc 1800
gtggcatggg tgcccaagta ctccggcgtg tctccccggg acaagtgcaa gctcatctgc 1860
cgagccaatg gcactggcta cttctatgtg ctggcaccca aggtggtgga cggcacgctg 1920
tgctctcctg actccacctc cgtctgtgtc caaggcaagt gcatcaaggc tggctgtgat 1980
gggaacctgg gctccaagaa gagattcgac aagtgtgggg tgtgtggggg agacaataag 2040
agctgcaaga aggtgactgg actcttcacc aagcccatgc atggctacaa tttcgtggtg 2100
gccatccccg caggcgcctc aagcatcgac atccgccagc gcggttacaa agggctgatc 2160
ggggatgaca actacctggc tctgaagaac agccaaggca agtacctgct caacgggcat 2220
ttcgtggtgt cggcggtgga gcgggacctg gtggtgaagg gcagtctgct gcggtacagc 2280
ggcacgggca cagcggtgga gagcctgcag gcttcccggc ccatcctgga gccgctgacc 2340
gtggaggtcc tctccgtggg gaagatgaca ccgccccggg tccgctactc cttctatctg 2400
cccaaagagc ctcgggagga caagtcctct catcccaagg acccccgggg accctctgtc 2460
ttgcacaaca gcgtcctcag cctctccaac caggtggagc agccggacga caggccccct 2520
gcacgctggg tggctggcag ctgggggccg tgctccgcga gctgcggcag tggcctgcag 2580
aagcgggcgg tggactgccg gggctccgcc gggcagcgca cggtccctgc ctgtgatgca 2640
gcccatcggc ccgtggagac acaagcctgc ggggagccct gccccacctg ggagctcagc 2700
gcctggtcac cctgctccaa gagctgcggc cggggatttc agaggcgctc actcaagtgt 2760
gtgggccacg gaggccggct gctggcccgg gaccagtgca acttgcaccg caagccccag 2820
gagctggact tctgcgtcct gaggccgtgc tgagtggggt catcgctttc tccccctcac 2880
tctccacccc actgatatgc cagcgttctg ccagctggag tagcgggcag aggacggtgg 2940
ccaggggctc acgccacgat gtcacccaca tccggggaca aggaccatgg gctggggcga 3000
gaggttccct cctcctccct ggactgggca gagggaagcc caggaactcc cgcacagtct 3060
acctcaggcc ccgctcctcg ggccggttgc ggggagaggc tttgaggtgc agggcagaag 3120
gtgctgaggc ccagtttcca aggaacttgg aggatgggca ccttccaggc agaacttcag 3180
ggaccccggc ccccagaacg gaggccacag gctgctggaa gagccatgtc ccagcagctt 3240
ggcaccctca ggtggcccca tggctctgga gccgtgtctg aacgaggcag ggttttcacg 3300
gtgcttttag cccactttcc tttttgaact gacatggact aagcaataaa agctggctgg 3360
ggctgggcag aagccacggg gagagtgaga ttagggcccc tggagcctgg cactccacct 3420
tggaagacgt ggacgtgcac agggagtccc gaggtttctc atcctgcact cttggccctc 3480
ctataaagaa gcagcctctc cttcctctga tgtgcagggt gtaggactag tggtagggct 3540
gccacggaag tgtcctctga ggctctgcag gtagcgggga aagccagtag ggagtctgct 3600
gtcttcttca agatggagcc ggccattaca gaaagatgtt gacatttgct aggggctatg 3660
cagtctgtgg ctgatgcagg gagttttcag aaagttctgg agggttctgc tgtcactgga 3720
ctggggttgg tgctgagctc tgggcctggc tttgggagat gtcaccctgg gatagggagg 3780
aggaagctgc atttctaatg gcttcctcct ccagagaggc acgtatatgc aggctgacat 3840
ccgagggtct gtgtcgcctc agacagccct gacagtggcc acagtcccgt acccattgtg 3900
aggggctggg gcatgcctag gagggctagg tgctgaacat ctatgtgcct ataaactcgt 3960
cttcgttcca aacagctact gctgtctgcc ctgggcacgt cacgttgcat cctaggcctt 4020
agcttctcca ctgtttgcta cctcagatta tgccctctgg gaacccagcc gtatccctcc 4080
cctaggacag tggtgacctg gtccttccac cacactcagt ctttggagag cgagctgtcc 4140
agccacagaa atgagggtgt ggtgcgtggc ttcctgctcc ccacagccca gccccctgtt 4200
ggggctccaa agccgaagac agggcctctt cagactcctt gggagtaggt ttcaggaggc 4260
accaagaatc aatgactgac ccaggggggcc tggcagccac tagtatgaac tgctggagac 4320
ctgtctgtct tatagacatg tcaggaaaat agaaacaggc attttctcta gctccaagtg 4380
gggagatatt ttggggtcac agcttctttg gctaagcagg gtgtttcttg aaggttcaga 4440
tgccccactg tgtacatggg atattctgct tctgagtgta ggtgatgaat ccaggtcctc 4500

-continued

```
agtggagaat tttctggagc taagatcaaa gcatgtgtct tcctgggaga gaagagttcc   4560
gttcttttat gtgggtttcc ctaatagtca gaatccacaa accagccagc cagccagcca   4620
agcctctgcg atgatgttct catccggtct aacgctgggc tggaaacctt ggacagagtt   4680
catgcggggg cagagggggt gccagtctct gaggcagggc tgcagtcacc cctgaagaac   4740
taagtgaaca ggaacccctc tgtgccagtg accactgtgg ggctaaaggg acaaaaagga   4800
ccagggtacc aggcagaagc agatccttga tagctgacga cagcactgcg ccctgtgctt   4860
ggtgcactcc ctccttcagg aggagagggt ggcatggggt ctgtgcggga tggcaggggg   4920
attgggtggg tgggaagaga ggtgccatcg gtaggaggct ggcctccagt agaggagagc   4980
agcttttgcc atcagtcact ttacaaacca tttcaaggaa ggacaacctc tctggctcct   5040
gacacaagcc aggcctcggt gcttttatct gttgtggtgg tttttcttct ttcccttttt   5100
aaaagacgca tgaccaagac aacctaggga gtttgtcttg cttgcctttg actatttcct   5160
taatccaacc atgctctcga gggctgagca gagactagac tcaaggcaca ggtttctggt   5220
gatggagtaa agttacagcg gtatctcatg tctacacaag aagaggaacg ttctgaaagc   5280
tccaacaact tcttgagggg gatggaccaa tacagctttg ggctcaggat tccctagcct   5340
cctctgccca tcgcgtgcac tgattggagg agtctggccc aaacactctc atatgaacct   5400
cgacatgctg gagtggggtc tggcaggagc tgatgacagt ttgagggact tgagtgtccc   5460
tagcctggca gttggctccc ggaagcacta gacactgaca ctcattggta gaccctccct   5520
ccccgccgtt gtgtttggtt cttttgcact ccatgtactg cagaaggatg gaaggacctg   5580
ggtgctggct gggctgtgta tactgtgtat acaagggagc tggctgctga ggtgaccaca   5640
gccttctcct aataaagctg taagtattta aaacct                             5676
```

<210> SEQ ID NO 12
<211> LENGTH: 1391
<212> TYPE: DNA
<213> ORGANISM: homo sapiens

<400> SEQUENCE: 12

```
acacaccctg acccgcatcg ccctgggtct ctcgagcctg ctgcctgctc ccccgcccca     60
ccagccatgg tggtttctgg agcgccccca gccctgggtg ggggctgtct cggcaccttc    120
acctccctgc tgctgctggc gtcgacagcc atcctcaatg cggccaggat acctgttccc    180
ccagcctgtg ggaagcccca gcagctgaac cgggttgtgg gcggcgagga cagcactgac    240
agcgagtggc cctggatcgt gagcatccag aagaatggga cccaccactg cgcaggttct    300
ctgctcacca gccgctgggt gatcactgct gcccactgtt tcaaggacaa cctgaacaaa    360
ccatacctgt tctctgtgct gctgggggcc tggcagctgg ggaaccctgg ctctcggtcc    420
cagaaggtgg gtgttgcctg ggtggagccc caccctgtgt attcctggaa ggaaggtgcc    480
tgtgcagaca ttgccctggt gcgtctcgag cgctccatac agttctcaga gcgggtcctg    540
cccatctgcc tacctgatgc ctctatccac ctccctccaa acacccactg ctggatctca    600
ggctggggga gcatccaaga tggagttccc ttgccccacc ctcagaccct gcagaagctg    660
aaggttccta tcatcgactc ggaagtctgc agccatctgt actggcgggg agcaggacag    720
ggacccatca ctgaggacat gctgtgtgcc ggctacttgg agggggagcg ggatgcttgt    780
ctgggcgact ccgggggccc cctcatgtgc caggtggacg gcgcctggct gctggccggc    840
atcatcagct ggggcgaggg ctgtgccgag cgcaacaggc ccggggtcta catcagcctc    900
tctgcgcacc gctcctgggt ggagaagatc gtgcaagggg tgcagctccg cgggcgcgct    960
```

```
caggggggtg gggccctcag ggcaccgagc cagggctctg gggccgccgc gcgctcctag   1020

ggcgcagcgg gacgcggggc tcggatctga aaggcggcca gatccacatc tggatctgga   1080

tctgcggcgg cctcgggcgg tttcccccgc cgtaaatagg ctcatctacc tctacctctg   1140

ggggcccgga cggctgctgc ggaaaggaaa ccccctcccc gacccgcccg acggcctcag   1200

gccccgcctc caaggcatca ggccccgccc aacggcctca tgtccccgcc cccacgactt   1260

ccggccccgc cccgggcccc agcgcttttg tgtatataaa tgttaatgat ttttataggt   1320

atttgtaacc ctgcccacat atcttattta ttcctccaat ttcaataaat tatttattct   1380

ccagtgaaaa a                                                         1391
```

<210> SEQ ID NO 13
<211> LENGTH: 4461
<212> TYPE: DNA
<213> ORGANISM: homo sapiens

<400> SEQUENCE: 13

```
agtccagaca accggcttcc agctggggct ggggaaaggg ggttggaggg gtgcgccccc     60

cccccacgcc ccttaggggt gggggacgcg ggctcagagt tccagggacc caggaatgcc    120

cccccgccag ccccctcggc aggcgggggg agggctcagc cgggagtttg gcaaactcct    180

ccccgcgttg agtcattcgc ctctgggagg tttaggaagc ggctccgggt cggtggcccc    240

aggacaggga agagcgggcg ctatggggag ccggacgcca gagtcccctc tccacgccgt    300

gcagctgcgc tggggccccc ggcgccgacc cccgctgctg ccgctgctgt tgctgctgct    360

gccgccgcca cccagggtcg ggggcttcaa cttagacgcg gaggccccag cagtactctc    420

ggggcccccg ggctccttct tcggattctc agtggagttt taccggccgg gaacagacgg    480

ggtcagtgtg ctggtgggag cacccaaggc taataccagc cagccaggag tgctgcaggg    540

tggtgctgtc tacctctgtc cttggggtgc cagccccaca cagtgcaccc ccattgaatt    600

tgacagcaaa ggctctcggc tcctggagtc ctcactgtcc agctcagagg gagaggagcc    660

tgtggagtac aagtccttgc agtggttcgg ggcaacagtt cgagcccatg gctcctccat    720

cttggcatgc gctccactgt acagctggcg cacagagaag gagccactga gcgaccccgt    780

gggcacctgc tacctctcca cagataactt cacccgaatt ctggagtatg caccctgccg    840

ctcagatttc agctgggcag caggacaggg ttactgccaa ggaggcttca gtgccgagtt    900

caccaagact ggccgtgtgg ttttaggtgg accaggaagc tatttctggc aaggccagat    960

cctgtctgcc actcaggagc agattgcaga atcttattac cccgagtacc tgatcaacct   1020

ggttcagggg cagctgcaga ctcgccaggc cagttccatc tatgatgaca gctacctagg   1080

atactctgtg gctgttggtg aattcagtgg tgatgacaca gaagactttg ttgctggtgt   1140

gcccaaaggg aacctcactt acggctatgt caccatcctt aatggctcag acattcgatc   1200

cctctacaac ttctcagggg aacagatggc ctcctacttt ggctatgcag tggccgccac   1260

agacgtcaat ggggacgggc tggatgactt gctggtgggg gcacccctgc tcatggatcg   1320

gacccctgac gggcggcctc aggaggtggg cagggtctac gtctacctgc agcacccagc   1380

cggcatagag cccacgccca cccttaccct cactggccat gatgagtttg gccgatttgg   1440

cagctccttg accccccctgg gggacctgga ccaggatggc tacaatgatg tggccatcgg   1500

ggctcccttt ggtggggaga cccagcaggg agtagtgttt gtatttcctg gggggcccagg   1560

agggctgggc tctaagcctt cccaggttct gcagcccctg tgggcagcca gccacacccc   1620
```

-continued

```
agacttcttt ggctctgccc ttcgaggagg ccgagacctg gatggcaatg gatatcctga   1680
tctgattgtg gggtcctttg gtgtggacaa ggctgtggta tacaggggcc gccccatcgt   1740
gtccgctagt gcctccctca ccatcttccc cgccatgttc aacccagagg agcggagctg   1800
cagcttagag gggaaccctg tggcctgcat caaccttagc ttctgcctca atgcttctgg   1860
aaaacacgtt gctgactcca ttggtttcac agtggaactt cagctggact ggcagaagca   1920
gaagggaggg gtacggcggg cactgttcct ggcctccagg caggcaaccc tgacccagac   1980
cctgctcatc cagaatgggg ctcgagagga ttgcagagag atgaagatct acctcaggaa   2040
cgagtcagaa tttcgagaca aactctcgcc gattcacatc gctctcaact tctccttgga   2100
cccccaagcc ccagtggaca gccacggcct caggccagcc ctacattatc agagcaagag   2160
ccggatagag gacaaggctc agatcttgct ggactgtgga gaagacaaca tctgtgtgcc   2220
tgacctgcag ctggaagtgt ttggggagca gaaccatgtg tacctgggtg acaagaatgc   2280
cctgaacctc actttccatg cccagaatgt gggtgagggt ggcgcctatg aggctgagct   2340
tcgggtcacc gcccctccag aggctgagta ctcaggactc gtcagacacc cagggaactt   2400
ctccagcctg agctgtgact actttgccgt gaaccagagc cgcctgctgg tgtgtgacct   2460
gggcaacccc atgaaggcag gagccagtct gtggggtggc cttcggttta cagtccctca   2520
tctccgggac actaagaaaa ccatccagtt tgacttccag atcctcagca agaatctcaa   2580
caactcgcaa agcgacgtgg tttcctttcg gctctccgtg gaggctcagg cccaggtcac   2640
cctgaacggt gtctccaagc ctgaggcagt gctattccca gtaagcgact ggcatccccg   2700
agaccagcct cagaaggagg aggacctggg acctgctgtc caccatgtct atgagctcat   2760
caaccaaggc cccagctcca ttagccaggg tgtgctggaa ctcagctgtc cccaggctct   2820
ggaaggtcag cagctcctat atgtgaccag agttacggga ctcaactgca ccaccaatca   2880
ccccattaac ccaaagggcc tggagttgga tcccgagggt tccctgcacc accagcaaaa   2940
acgggaagct ccaagccgca gctctgcttc ctcgggacct cagatcctga aatgcccgga   3000
ggctgagtgt ttcaggctgc gctgtgagct cgggcccctg caccaacaag agagccaaag   3060
tctgcagttg catttccgag tctgggccaa gactttcttg cagcgggagc accagccatt   3120
tagcctgcag tgtgaggctg tgtacaaagc cctgaagatg ccctaccgaa tcctgcctcg   3180
gcagctgccc caaaaagagc gtcaggtggc cacagctgtg caatggacca aggcagaagg   3240
cagctatggc gtcccactgt ggatcatcat cctagccatc ctgtttggcc tcctgctcct   3300
aggtctactc atctacatcc tctacaagct tggattcttc aaacgctccc tcccatatgg   3360
caccgccatg gaaaaagctc agctcaagcc tccagccacc tctgatgcct gagtcctccc   3420
aatttcagac tcccattcct gaagaaccag tcccccccacc ctcattctac tgaaaaggag   3480
gggtctgggt acttcttgaa ggtgctgacg gccagggaga agctcctctc cccagcccag   3540
agacatactt gaagggccag agccaggggg gtgaggagct ggggatccct cccccccatg   3600
cactgtgaag gacccttgtt tacacatacc ctcttcatgg atgggggaac tcagatccag   3660
ggacagaggc cccagcctcc ctgaagcctt tgcattttgg agagtttcct gaaacaactt   3720
ggaaagataa ctaggaaatc cattcacagt tctttgggcc agacatgcca caaggacttc   3780
ctgtccagct ccaacctgca aagatctgtc ctcagccttg ccagagatcc aaaagaagcc   3840
cccagctaag aacctggaac ttggggagtt aagacctggc agctctggac agccccaccc   3900
tggtgggcca acaaagaaca ctaactatgc atggtgcccc aggaccagct caggacagat   3960
gccacacaag gatagatgct ggcccagggc ccagagccca gctccaaggg gaatcagaac   4020
```

```
tcaaatgggg ccagatccag cctggggtct ggagttgatc tggaacccag actcagacat   4080

tggcacctaa tccaggcaga tccaggacta tatttgggcc tgctccagac ctgatcctgg   4140

aggcccagtt caccctgatt taggagaagc caggaatttc ccaggaccct gaaggggcca   4200

tgatggcaac agatctggaa cctcagcctg gccagacaca ggccctccct gttccccaga   4260

gaaaggggag cccactgtcc tgggcctgca gaatttgggt tctgcctgcc agctgcactg   4320

atgctgcccc tcatctctct gcccaaccct tccctcacct tggcaccaga cacccaggac   4380

ttatttaaac tctgttgcaa gtgcaataaa tctgacccag tgccccccact gaccagaact   4440

agaaaaaaaa aaaaaaaaaa a                                               4461
```

<210> SEQ ID NO 14
<211> LENGTH: 2073
<212> TYPE: DNA
<213> ORGANISM: homo sapiens

<400> SEQUENCE: 14

```
agatgccacg ccccatagct ccaccagtca ccgcggcaca gtggccctta agcgaggagc     60

ggcggcgccc gcagcaatca cagcagtgcc gacgtcgtgg gtgtttggtg tgaggctgcg    120

agccgccgcg agttctcacg gtcccgccgg cgccaccacc gcggtcactc accgccgccg    180

ccgccaccac tgccaccacg gtcgcctgcc acaggtgtct gcaattgaac tccaaggtgc    240

agaatggttt ggaaagtagc tgtattcctc agtgtggccc tgggcattgg tgccgttcct    300

atagatgatc ctgaagatgg aggcaagcac tgggtggtga tcgtggcagg ttcaaatggc    360

tggtataatt ataggcacca ggcagacgcg tgccatgcct accagatcat tcaccgcaat    420

gggattcctg acgaacagat cgttgtgatg atgtacgatg acattgctta ctctgaagac    480

aatcccactc caggaattgt gatcaacagg cccaatggca cagatgtcta tcagggagtc    540

ccgaaggact acactggaga ggatgttacc cccacaaaatt tccttgctgt gttgagaggc    600

gatgcagaag cagtgaaggg cataggatcc ggcaaagtcc tgaagagtgg cccccaggat    660

cacgtgttca tttacttcac tgaccatgga tctactggaa tactggtttt tcccaatgaa    720

gatcttcatg taaaggacct gaatgagacc atccattaca tgtacaaaca caaaatgtac    780

cgaaagatgg tgttctacat tgaagcctgt gagtctgggt ccatgatgaa ccacctgccg    840

gataacatca atgtttatgc aactactgct gccaacccca gagagtcgtc ctacgcctgt    900

tactatgatg agaagaggtc cacgtacctg gggactggt acagcgtcaa ctggatggaa    960

gattcggacg tggaagatct gactaaagag accctgcaca agcagtacca cctggtaaaa   1020

tcgcacacca acaccagcca cgtcatgcag tatggaaaca aaacaatctc caccatgaaa   1080

gtgatgcagt ttcagggtat gaaacgcaaa gccagttctc ccgtccccct acctccagtc   1140

acacaccttg acctcacccc cagccctgat gtgcctctca ccatcatgaa aaggaaactg   1200

atgaacacca atgatctgga ggagtccagg cagctcacgg aggagatcca gcggcatctg   1260

gatgccaggc acctcattga gaagtcagtg cgtaagatcg tctccttgct ggcagcgtcc   1320

gaggctgagg tggagcagct cctgtccgag agagccccgc tcacggggca cagctgctac   1380

ccagaggccc tgctgcactt ccggacccac tgcttcaact ggcactcccc cacgtacgag   1440

tatgcgttga gacatttgta cgtgctggtc aacctttgtg agaagccgta tccgcttcac   1500

aggataaaat tgtccatgga ccacgtgtgc cttggtcact actgaagagc tgcctcctgg   1560

aagcttttcc aagtgtgagc gccccaccga ctgtgtgctg atcagagact ggagaggtgg   1620
```

agtgagaagt ctccgctgct cgggccctcc tggggagccc ccgctccagg gctcgctcca 1680
ggaccttctt cacaagatga cttgctcgct gttacctgct tccccagtct tttctgaaaa 1740
actacaaatt agggtgggaa aagctctgta ttgagaaggg tcatatttgc tttctaggag 1800
gtttgttgtt ttgcctgtta gttttgagga gcaggaagct catgggggct tctgtagccc 1860
ctctcaaaag gagtctttat tctgagaatt tgaagctgaa acctctttaa atcttcagaa 1920
tgattttatt gaagagggcc gcaagcccca aatggaaaac tgtttttaga aaatatgatg 1980
atttttgatt gcttttgtat ttaattctgc aggtgttcaa gtcttaaaaa ataaagattt 2040
ataacagaac ccaaataaaa aaaaaaaaaa aaa 2073

<210> SEQ ID NO 15
<211> LENGTH: 3610
<212> TYPE: DNA
<213> ORGANISM: homo sapiens

<400> SEQUENCE: 15
gagaggctgt gggagaaggg agggaccaga ggagagagcg agagagggaa ccagacccca 60
gttcgccgac taagcagaag aaagatcaaa aaccggaaaa gaggagaaga gcaaacaggc 120
actttgagga acaatcccct ttaactccaa gccgacagcg gtctaggaat tcaagttcag 180
tgcctaccga agacaaaggc gccccgaggg agtggcggtg cgaccccagg gcgtgggccc 240
ggccgcggag cccacactgc ccggctgacc cggtggtctc ggaccatgtc tcccgcccca 300
agaccccccc gttgtctcct gctccccctg ctcacgctcg gcaccgcgct cgcctccctc 360
ggctcggccc aaagcagcag cttcagcccc gaagcctggc tacagcaata tggctacctg 420
cctcccgggg acctacgtac ccacacacag cgctcacccc agtcactctc agcggccatc 480
gctgccatgc agaagtttta cggcttgcaa gtaacaggca aagctgatgc agacaccatg 540
aaggccatga ggcgcccccg atgtggtgtt ccagacaagt ttggggctga gatcaaggcc 600
aatgttcgaa ggaagcgcta cgccatccag ggtctcaaat ggcaacataa tgaaatcact 660
ttctgcatcc agaattacac ccccaaggtg ggcgagtatg ccacatacga ggccattcgc 720
aaggcgttcc gcgtgtggga gagtgccaca ccactgcgct tccgcgaggt gccctatgcc 780
tacatccgtg agggccatga gaagcaggcc gacatcatga tcttctttgc cgagggcttc 840
catggcgaca gcacgccctt cgatggtgag ggcggcttcc tggcccatgc ctacttccca 900
ggccccaaca ttggaggaga cacccacttt gactctgccg agccttggac tgtcaggaat 960
gaggatctga atggaaatga catcttcctg gtggctgtgc acgagctggg ccatgccctg 1020
gggctcgagc attccagtga cccctcggcc atcatggcac ccttttacca gtggatggac 1080
acggagaatt ttgtgctgcc cgatgatgac cgccggggca tccagcaact ttatgggggt 1140
gagtcagggt tccccaccaa gatgcccccct caacccagga ctacctcccg gccttctgtt 1200
cctgataaac ccaaaaaccc cacctatggg cccaacatct gtgacgggaa ctttgacacc 1260
gtggccatgc tccgagggga gatgtttgtc ttcaaggagc gctggttctg gcgggtgagg 1320
aataaccaag tgatggatgg atacccaatg cccattggcc agttctggcg gggcctgcct 1380
gcgtccatca acactgccta cgagaggaag gatggcaaat tcgtcttctt caaaggagac 1440
aagcattggg tgtttgatga ggcgtccctg gaacctggct accccaagca cattaaggag 1500
ctgggccgag ggctgcctac cgacaagatt gatgctgctc tcttctggat gcccaatgga 1560
aagacctact tcttccgtgg aaacaagtac taccgtttca acgaagagct cagggcagtg 1620
gatagcgagt accccaagaa catcaaagtc tgggaaggga tccctgagtc tcccagaggg 1680

```
tcattcatgg gcagcgatga agtcttcact tacttctaca aggggaacaa atactggaaa   1740
ttcaacaacc agaagctgaa ggtagaaccg ggctacccca agtcagccct gagggactgg   1800
atgggctgcc catcgggagg ccggccggat gaggggactg aggaggagac ggaggtgatc   1860
atcattgagg tggacgagga gggcggcggg gcggtgagcg cggctgccgt ggtgctgccc   1920
gtgctgctgc tgctcctggt gctggcggtg ggccttgcag tcttcttctt cagacgccat   1980
gggaccccca ggcgactgct ctactgccag cgttccctgc tggacaaggt ctgacgccca   2040
ccgccggccc gcccactcct accacaagga ctttgcctct gaaggccagt ggcagcaggt   2100
ggtggtgggt gggctgttcc catcgtcccg agcccccctcc ccgcagcctc cttgcttctc   2160
tctgtcccct ggctggcctc cttcaccctg accgcctccc tccctcctgc cccggcattg   2220
catcttccct agataggtcc cctgagggct gagtgggagg gcggcccttt ccagcctctg   2280
cccctcaggg gaaccctgta gctttgtgtc tgtccagccc catctgaatg tgttgggggc   2340
tctgcacttg aaggcaggac cctcagacct cgctggtaaa ggtcaaatgg ggtcatctgc   2400
tccttttcca tcccctgaca taccttaacc tctgaactct gacctcagga ggctctgggc   2460
actccagccc tgaaagcccc aggtgtaccc aattggcagc ctctcactac tctttctggc   2520
taaaaggaat ctaatcttgt tgagggtaga gaccctgaga cagtgtgagg gggtggggac   2580
tgccaagcca ccctaagacc ttgggaggaa aactcagaga gggtcttcgt tgctcagtca   2640
gtcaagttcc tcggagatct gcctctgcct cacctacccc agggaacttc caaggaagga   2700
gcctgagcca ctggggacta agtgggcaga agaaaccctt ggcagccctg tgcctctcga   2760
atgttagcct tggatggggc tttcacagtt agaagagctg aaaccagggg tgcagctgtc   2820
aggtagggtg gggccggtgg gagaggcccg ggtcagagcc ctgggggtga gcctgaaggc   2880
cacagagaaa gaaccttgcc caaactcagg cagctggggc tgaggcccaa aggcagaaca   2940
gccagagggg gcaggagggg accaaaaagg aaaatgagga cgtgcagcag cattggaagg   3000
ctggggccgg gcaggccagg ccaagccaag caggggggcca cagggtgggc tgtggagctc   3060
tcaggaaggg ccctgaggaa ggcacacttg ctcctgttgg tccctgtcct tgctgcccag   3120
gcagcgtgga ggggaagggt agggcagcca gagaaaggag cagagaaggc acacaaacga   3180
ggaatgaggg gcttcacgag aggccacagg gcctggctgg ccacgctgtc ccggcctgct   3240
caccatctca gtgaggggca ggagctgggg ctcgcttagg ctgggtccac gcttccctgg   3300
tgccagcacc cctcaagcct gtctcaccag tggcctgccc tctcgctccc ccacccagcc   3360
cacccattga agtctccttg ggccaccaaa ggtggtggcc atggtaccgg ggacttggga   3420
gagtgagacc cagtggaggg agcaagagga gagggatgtc ggggggggtgg ggcacggggt   3480
aggggaaatg gggtgaacgg tgctggcagt tcggctagat ttctgtcttg tttgtttttt   3540
tgttttgttt aatgtatatt tttattataa ttattatata tgaattccat tcaaaaaaaa   3600
aaaaaaaaaa                                                        3610
```

<210> SEQ ID NO 16
<211> LENGTH: 941
<212> TYPE: DNA
<213> ORGANISM: homo sapiens

<400> SEQUENCE: 16

```
ccaagagcta aaagagagca aggaggaaac aacagcagct ccaaccaggg cagccttcct     60
gagaagatgc aaccaatcct gcttctgctg gccttcctcc tgctgcccag ggcagatgca    120
```

-continued

```
ggggagatca tcgggggaca tgaggccaag ccccactccc gcccctacat ggcttatctt    180

atgatctggg atcagaagtc tctgaagagg tgcggtggct tcctgatacg agacgacttc    240

gtgctgacag ctgctcactg ttggggaagc tccataaatg tcaccttggg ggcccacaat    300

atcaaagaac aggagccgac ccagcagttt atccctgtga aaagacccat cccccatcca    360

gcctataatc ctaagaactt ctccaacgac atcatgctac tgcagctgga gagaaaggcc    420

aagcggacca gagctgtgca gcccctcagg ctacctagca acaaggccca ggtgaagcca    480

gggcagacat gcagtgtggc cggctggggg cagacggccc ccctgggaaa acactcacac    540

acactacaag aggtgaagat gacagtgcag gaagatcgaa agtgcgaatc tgacttacgc    600

cattattacg acagtaccat tgagttgtgc gtgggggacc cagagattaa aaagacttcc    660

tttaaggggg actctggagg ccctcttgtg tgtaacaagg tggcccaggg cattgtctcc    720

tatggacgaa acaatggcat gcctccacga gcctgcacca aagtctcaag ctttgtacac    780

tggataaaga aaaccatgaa acgctactaa ctacaggaag caaactaagc ccccgctgta    840

atgaaacacc ttctctggag ccaagtccag atttacactg ggagaggtgc cagcaactga    900

ataaatacct cttagctgag tggaaaaaaa aaaaaaaaaa a                         941
```

```
<210> SEQ ID NO 17
<211> LENGTH: 2387
<212> TYPE: DNA
<213> ORGANISM: homo sapiens

<400> SEQUENCE: 17

agacacctct gccctcacca tgagcctctg gcagcccctg gtcctggtgc tcctggtgct     60

gggctgctgc tttgctgccc ccagacagcg ccagtccacc cttgtgctct tccctggaga    120

cctgagaacc aatctcaccg acaggcagct ggcagaggaa tacctgtacc gctatggtta    180

cactcgggtg gcagagatgc gtggagagtc gaaatctctg gggcctgcgc tgctgcttct    240

ccagaagcaa ctgtccctgc ccgagaccgg tgagctggat agcgccacgc tgaaggccat    300

gcgaacccca cggtgcgggg tcccagacct gggcagattc caaacctttg agggcgacct    360

caagtggcac caccacaaca tcacctattg gatccaaaac tactcggaag acttgccgcg    420

ggcggtgatt gacgacgcct ttgcccgcgc cttcgcactg tggagcgcgg tgacgccgct    480

caccttcact cgcgtgtaca gccgggacgc agacatcgtc atccagtttg gtgtcgcgga    540

gcacggagac gggtatccct tcgacgggaa ggacgggctc ctggcacacg cctttcctcc    600

tggccccggc attcagggag acgcccattt cgacgatgac gagttgtggt ccctgggcaa    660

gggcgtcgtg gttccaactc ggtttggaaa cgcagatggc gcggcctgcc acttcccctt    720

catcttcgag ggccgctcct actctgcctg caccaccgac ggtcgctccg acggcttgcc    780

ctggtgcagt accacggcca actacgacac cgacgaccgg tttggcttct gccccagcga    840

gagactctac acccaggacg gcaatgctga tgggaaaccc tgccagtttc cattcatctt    900

ccaaggccaa tcctactccg cctgcaccac ggacggtcgc tccgacggct accgctggtg    960

cgccaccacc gccaactacg accgggacaa gctcttcggc ttctgcccga cccgagctga   1020

ctcgacggtg atgggggggca actcggcggg ggagctgtgc gtcttcccct tcactttcct   1080

gggtaaggag tactcgacct gtaccagcga gggccgcgga gatgggcgcc tctggtgcgc   1140

taccacctcg aactttgaca gcgacaagaa gtggggcttc tgcccggacc aaggatacag   1200

tttgttcctc gtggcggcgc atgagttcgg ccacgcgctg ggcttagatc attcctcagt   1260

gccggaggcg ctcatgtacc ctatgtaccg cttcactgag ggcccccct tgcataagga    1320
```

```
cgacgtgaat ggcatccggc acctctatgg tcctcgccct gaacctgagc cacggcctcc   1380

aaccaccacc acaccgcagc ccacggctcc cccgacggtc tgccccaccg gaccccccac   1440

tgtccacccc tcagagcgcc ccacagctgg ccccacaggt caccccctcag ctggccccac   1500

aggtcccccc actgctggcc cttctacggc cactactgtg cctttgagtc cggtggacga   1560

tgcctgcaac gtgaacatct tcgacgccat cgcggagatt gggaaccagc tgtatttgtt   1620

caaggatggg aagtactggc gattctctga gggcaggggg agccggccgc agggcccctt   1680

ccttatcgcc gacaagtggc ccgcgctgcc ccgcaagctg gactcggtct ttgaggagcg   1740

gctctccaag aagcttttct tcttctctgg gcgccaggtg tgggtgtaca caggcgcgtc   1800

ggtgctgggc ccgaggcgtc tggacaagct gggcctggga gccgacgtgg cccaggtgac   1860

cggggccctc cggagtggca gggggaagat gctgctgttc agcgggcggc gcctctggag   1920

gttcgacgtg aaggcgcaga tggtggatcc ccggagcgcc agcgaggtgg accggatgtt   1980

ccccggggtg cctttggaca cgcacgacgt cttccagtac cgagagaaag cctatttctg   2040

ccaggaccgc ttctactggc gcgtgagttc ccggagtgag ttgaaccagg tggaccaagt   2100

gggctacgtg acctatgaca tcctgcagtg ccctgaggac tagggctccc gtcctgcttt   2160

ggcagtgcca tgtaaatccc cactgggacc aaccctgggg aaggagccag tttgccggat   2220

acaaactggt attctgttct ggaggaaagg gaggagtgga ggtgggctgg gccctctctt   2280

ctcacctttg tttttgttg gagtgtttct aataaacttg gattctctaa cctttaaaaa   2340

aaaaaaaaaa aaaaaaaaaa aaaaaaaaaa aaaaaaaaaa aaaaaaa                 2387
```

<210> SEQ ID NO 18
<211> LENGTH: 840
<212> TYPE: DNA
<213> ORGANISM: homo sapiens

<400> SEQUENCE: 18

```
actcgccacc tcctcttcca cccctgccag gcccagcagc caccacagcg cctgcttcct     60

cggccctgaa atcatgcccc taggtctcct gtggctgggc ctagccctgt tgggggctct    120

gcatgcccag gcccaggact ccacctcaga cctgatccca gccccacctc tgagcaaggt    180

ccctctgcag cagaacttcc aggacaacca attccagggg aagtggtatg tggtaggcct    240

ggcagggaat gcaattctca gagaagacaa agacccgcaa aagatgtatg ccaccatcta    300

tgagctgaaa gaagacaaga gctacaatgt cacctccgtc ctgtttagga aaaagaagtg    360

tgactactgg atcaggactt ttgttccagg ttgccagccc ggcgagttca cgctgggcaa    420

cattaagagt taccctggat taacgagtta cctcgtccga gtggtgagca ccaactacaa    480

ccagcatgct atggtgttct tcaagaaagt ttctcaaaac agggagtact tcaagatcac    540

cctctacggg agaaccaagg agctgacttc ggaactaaag gagaacttca tccgcttctc    600

caaatctctg ggcctccctg aaaaccacat cgtcttccct gtcccaatcg accagtgtat    660

cgacggctga gtgcacaggt gccgccagct gccgcaccag cccgaacacc attgagggag    720

ctgggagacc ctccccacag tgccacccat gcagctgctc cccaggccac cccgctgatg    780

gagccccacc ttgtctgcta aataaacatg tgccctcagg ccaaaaaaaa aaaaaaaaaa    840
```

<210> SEQ ID NO 19
<211> LENGTH: 3147
<212> TYPE: DNA
<213> ORGANISM: homo sapiens

<400> SEQUENCE: 19

```
gacacatgat gctgtgaacg tcagggtgct cgccagggaa gggccctacc cagagggaca     60
gaaagaaagc caggaggggt agagtttgaa gagaagatca tgttctccct gaagacgctt    120
ccatttctgc tcttactcca tgtgcagatt tccaaggcct ttcctgtatc ttctaaagag    180
aaaaatacaa aaactgttca gcagaataaa taagcctttt ctacagtagt gaagaggata    240
aaaaagagga actgcactga tgcaacaaat acctcaagag aagtcaatta atgactacct    300
ggaaaagttc taccaattac caagcaacca gtatcagtct acaaggaaga atggcactaa    360
tgtgatcgtt gaaaagctta aagaaatgca gcgatttttt gggttgaatg tgacggggaa    420
gccaaatgag gaaactctgg acatgatgaa aaagcctcgc tgtggagtgc ctgacagtgg    480
tggttttatg ttaaccccag gaaaccccaa gtgggaacgc actaacttga cctacaggat    540
tcgaaactat accccacagc tgtcagaggc tgaggtagaa agagctatca aggatgcctt    600
tgaactctgg agtgttgcat cacctctcat cttcaccagg atctcacagg gagaggcaga    660
tatcaacatt gctttttacc aaagagatca cggtgacaat tctccatttg atggacccaa    720
tggaatcctt gctcatgcct ttcagccagg ccaaggtatt ggaggagatg ctcattttga    780
tgccgaagaa acatggacca acacctccgc aaattacaac ttgtttcttg ttgctgctca    840
tgaatttggc cattctttgg ggctcgctca ctcctctgac cctggtgcct tgatgtatcc    900
caactatgct ttcagggaaa ccagcaacta ctcactccct caagatgaca tcgatggcat    960
tcaggccatc tatggacttt caagcaaccc tatccaacct actggaccaa gcacacccaa   1020
accctgtgac cccagtttga catttgatgc tatcaccaca ctccgtggag aaatactttt   1080
ctttaaagac aggtacttct ggagaaggca tcctcagcta caaagagtcg aaatgaattt   1140
tatttctcta ttctggccat cccttccaac tggtatacag gctgcttatg aagattttga   1200
cagagacctc attttcctat ttaaaggcaa ccaatactgg gctctgagtg gctatgatat   1260
tctgcaaggt tatcccaagg atatatcaaa ctatggcttc cccagcagcg tccaagcaat   1320
tgacgcagct gttttctaca gaagtaaaac atacttcttt gtaaatgacc aattctggag   1380
atatgataac caaagacaat tcatggagcc aggttatccc aaaagcatat caggtgcctt   1440
tccaggaata gagagtaaag ttgatgcagt tttccagcaa gaacatttct tccatgtctt   1500
cagtggacca agatattacg catttgatct tattgctcag agagttacca gagttgcaag   1560
aggcaataaa tggcttaact gtagatatgg ctgaagcaaa atcaaatgtg gctgtatcca   1620
ctttcagaat gttgaaggga agttcagcaa gcattttcgt tacattgtgt cctgcttata   1680
cttttctcaa tattaagtca ttgtttccca tcactgtatc cattctacct gtcctccgtg   1740
aaaatatgtt tggaatattc cactatttgc agaggcttat tcagttctta cacattccat   1800
cttacattag tgattccatc aaagagaagg aaagtaagcc tttttgtcac ctcaatattt   1860
actatttcaa tacttacata tctgacttct aggatttatt gttatattac ttgcctatct   1920
gacttcatac atccctcagt ttcttaaaat gtcctatgta tatcttctac atgcaattta   1980
gaactagatt ttggttagaa gtaaggatta taaacaacct agacagtacc cttggccttt   2040
acagaaaata tggtgctgtt ttctaccctt ggaaagaaat gtagatgata tgtttcgtgg   2100
gttgaattgt gtcccccata aaagatatgt tgaagttcta accccaggta cccatgaatg   2160
tgagcttacc agggtctttg cagatgtaat tagttaagtt aaggtgagat cacactgaat   2220
tagggtgggc tctaaatcca ttatgactgt tgttcttata agaagaagag aggcatagtc   2280
acctagggga ggaggccgta tgaagacaga ggcagagatt ggagtgacgc atctccaagc   2340
```

caaggaattc caaggactgt aagccaccag tagaagcttt gaagaggcaa ggaaggattc 2400
cctccaatag ccttcaagtg tgaccctgct gacacctgca gaattcggac ttctatcctc 2460
caaaaccgtg agggaataaa tttcctttgt tttaagccac caactttgca atactttgtt 2520
acagcaaccc tagacatgag gtactagaca cagtacatct acacatatga aaatgaatca 2580
acacagaatg cagaagtaga accettgcta aggactactg ggcatcttcc caggacagca 2640
gccaaaagag aaccaccact tcctctcctg cctcctcctt gctctctcct agagtccaaa 2700
cccaaatggg ccagttggat ctgatgttcg tcagttcttt acttctattt cctggggtac 2760
tcaggagggc acacactata gataacttgg gttagctgca taaaattcaa tgtctcatta 2820
agttgcatta aactgagctt agatgtgtaa gtttgctaac ggatgggttt ttttgttaag 2880
aactatagga tttatgggac caagtctagc gagtccagat atcaaaatca ttataatgtt 2940
atatttgctg ttattagaat ataatatagc ttattataca ataaatatgt agactgtaaa 3000
atatatttct cactagtacc tcctattttc tttctctgtt gaagttttta aatcccacag 3060
ataattaaat tggcaccttt atgcttgttc aaaaattaaa ataatctatt aaataagttc 3120
aaattaaaga tttttacttc aaatgac 3147

<210> SEQ ID NO 20
<211> LENGTH: 3276
<212> TYPE: DNA
<213> ORGANISM: homo sapiens

<400> SEQUENCE: 20
cgagcatttt tttttttttt tggaagtcct aggactgatc tccaggacca gcactcttct 60
cccagccctt agggtcctgc tcggccaagg ccttccctgc catgcgacct gtcagtgtct 120
ggcagtggag cccctggggg ctgctgctgt gcctgctgtg cagttcgtgc ttggggtctc 180
cgtccccttc cacgggccct gagaagaagg ccgggagcca ggggcttcgg ttccggctgg 240
ctggcttccc caggaagccc tacgagggcc gcgtggagat acagcgagct ggtgaatggg 300
gcaccatctg cgatgatgac ttcacgctgc aggctgccca catcctctgc cgggagctgg 360
gcttcacaga ggccacaggc tggacccaca gtgccaaata tggccctgga acaggccgca 420
tctggctgga caacttgagc tgcagtggga ccgagcagag tgtgactgaa tgtgcctccc 480
ggggctgggg gaacagtgac tgtacgcacg atgaggatgc tggggtcatc tgcaaagacc 540
agcgcctccc tggcttctcg gactccaatg tcattgaggc ccgtgtccgt ctaaagggcg 600
gcgcccaccc tggagagggc cgggtagaag tcctgaaggc cagcacatgg ggcacagtct 660
gtgaccgcaa gtgggacctg catgcagcca gcgtggtgtg tcgggagctg ggcttcggga 720
gtgctcgaga agctctgagt ggcgctcgca tggggcaggg catgggtgct atccacctga 780
gtgaagttcg ctgctctgga caggagctct ccctctggaa gtgcccccac aagaacatca 840
cagctgagga ttgttcacat agccaggatg ccggggtccg gtgcaaccta ccttacactg 900
gggcagagac caggatccga ctcagtgggg gccgcagcca acatgagggg cgagtcgagg 960
tgcaaatagg gggacctggg ccccttcgct ggggcctcat ctgtggggat gactggggga 1020
ccctggaggc catggtggcc tgtaggcaac tgggtctggg ctacgccaac cacggcctgc 1080
aggagacctg gtactgggac tctgggaata taacagaggt ggtgatgagt ggagtgcgct 1140
gcacagggac tgagctgtcc ctggatcagt gtgcccatca tggcacccac atcacctgca 1200
agaggacagg gacccgcttc actgctggag tcatctgttc tgagactgca tcagatctgt 1260

-continued

```
tgctgcactc agcactggtg caggagaccg cctacatcga agaccggccc ctgcatatgt   1320
tgtactgtgc tgcggaagag aactgcctgg ccagctcagc ccgctcagcc aactggccct   1380
atggtcaccg gcgtctgctc cgattctcct cccagatcca caacctggga cgagctgact   1440
tcaggcccaa ggctgggcgc cactcctggg tgtggcacga gtgccatggg cattaccaca   1500
gcatggacat cttcactcac tatgatatcc tcaccccaaa tggcaccaag gtggctgagg   1560
gccacaaagc tagtttctgt ctcgaagaca ctgagtgtca ggaggatgtc tccaagcggt   1620
atgagtgtgc caactttgga gagcaaggca tcactgtggg ttgctgggat ctctaccggc   1680
atgacattga ctgtcagtgg attgacatca cggatgtgaa gccaggaaac tacattctcc   1740
aggttgtcat caacccaaac tttgaagtag cagagagtga ctttaccaac aatgcaatga   1800
aatgtaactg caaatatgat ggacatagaa tctgggtgca caactgccac attggtgatg   1860
ccttcagtga agaggccaac aggaggtttg aacgctaccc tggccagacc agcaaccaga   1920
ttatctaagt gccactgccc tctgcaaacc accactggcc cctaatggca ggggtctgag   1980
gctgccatta cctcaggagc ttaccaagaa acccatgtca gcaaccgcac tcatcagacc   2040
atgcactatg gatgtggaac tgtcaagcag aagttttcac cctccttcag aggccagctg   2100
tcagtatctg tagccaagca tgggaatctt tgctcccagg cccagcaccg agcagaacag   2160
accagagccc accacaccac aaagagcagc acctgactaa ctgcccacaa aagatggcag   2220
cagctcattt tctttaatag gaggtcagga tggtcagctc cagtatctcc cctaagttta   2280
gggggataca gctttacctc tagccttttg gtgggggaaa agatccagcc ctcccacctc   2340
atttttact ataatatgtt gctaggtata attttatttt atataaaaag tgtttctgtg   2400
attcttcaga gcccaggagt cagtgctggt ggttggaggg acctgccccc actggttcat   2460
ttaaccctct gtctcggtgc cctcagaacc tcagccagaa aggcaaggag gaaatcagag   2520
caggagcctc atactcttgg tgatctattc attctgtgac ctcaggggtc acatataagg   2580
tcagtgtttc tcgtccccgc cggatctgca ctgccaactg ggattgggtt cgaacagctt   2640
cataaacatc ttcagcattt tgtaccatct gctccccaat ggccaaaatc acatcaccag   2700
gccgcagacc agccctatag agaaaaatgg acagagagaa aggaaggagt acaaagccta   2760
gttcaaggac acatgcacac cttgcccatc cccatatcac actgcagcct ctccctcacc   2820
ggtgtgcagg ggagcccagg atgactttat ggatgagtac accatgctga acatcgggaa   2880
agcttggttc tcgaagctgt agttcagcaa ggatgctgaa agtacacaga tcaccctatt   2940
agccaaaccc aggcattctc cccatcctga gttccacctc aagtctctca tcaacacatt   3000
gataaatata tggacaggac atgggctagg tactacaaaa tacaatggca actcactttc   3060
tgtcttctag caataaagtg caacatgtac ataaaagatg tacaccacat gagggcacca   3120
aatgacaaac agtgttaaat caatagcact aatgtcattc tagaatacta agagaagctt   3180
taaggggaaa gaacttaagt tgagcctaaa aggatggatc tgatattaac catataaaac   3240
aagaacagca taaataaaaa acatgggagt aggaaa                            3276
```

<210> SEQ ID NO 21
<211> LENGTH: 639
<212> TYPE: DNA
<213> ORGANISM: homo sapiens

<400> SEQUENCE: 21

```
gagagaagga gagcctgcag acagaggcct ccagcttggt ctgtctcccc acctctacca     60
gcatctgctg agctatgagc caaaccaggg atttacaggg aggaaaagct ttcggactgc    120
```

tgaaggccca gcaggaagag aggctggatg agatcaacaa gcaattccta gacgatccca 180
aatatagcag tgatgaggat ctgccctcca aactggaagg cttcaaagag aaatacatgg 240
agtttgacct taatggaaat ggcgatattg atatcatgtc cctgaaacga atgctggaga 300
aacttggagt ccccaagact cacctagagc taaagaaatt aattggagag gtgtccagtg 360
gctccgggga gacgttcagc taccctgact ttctcaggat gatgctgggc aagagatctg 420
ccatcctaaa aatgatcctg atgtatgagg aaaaagcgag agaaaaggaa aagccaacag 480 gcccccccagc caagaaagct atctctgagt tgccctgatt tgaagggaaa agggatgatg 540
ggattgaagg ggcttctaat gacccagata tggaaacaga agacaaaatt gtaagccaga 600
gtcaacaaat taaataaatt acccccctcct ccagatcaa 639

<210> SEQ ID NO 22
<211> LENGTH: 3810
<212> TYPE: DNA
<213> ORGANISM: homo sapiens

<400> SEQUENCE: 22
gcggcggccg ccttcgggga agggggtggg tccggggagg ggtttgccat cctcctctag 60
ttaaaagtaa gggggaaaag agtaaacgcg cgactccagc gcgcggctac ctacgcttgg 120
tgcttgcttt ctccagccat cggagaccag agccgccccc tctgctcgag aaaggggctc 180
agcggcggcg gaagcggagg gggaccaccg tggagagcgc ggtcccagcc cggccactgc 240
ggatccctga aaccaaaaag ctcctgctgc ttctgtaccc cgcctgtccc tcccagctgc 300
gcagggcccc ttcgtgggat catcagcccg aagacaggga tggagaggcc tctgtgctcc 360
cacctctgca gctgcctggc tatgctggcc ctcctgtccc ccctgagcct ggcacagtat 420
gacagctggc cccattaccc cgagtacttc cagcaaccgg ctcctgagta tcaccagccc 480
caggcccccg ccaacgtggc caagattcag ctgcgcctgg ctgggcagaa gaggaagcac 540
agcgagggcc gggtggaggt gtactatgat ggccagtggg gcaccgtgtg cgatgacgac 600
ttctccatcc acgctgccca cgtcgtctgc cgggagctgg gctacgtgga ggccaagtcc 660
tggactgcca gctcctccta cggcaaggga gaagggccca tctggttaga caatctccac 720
tgtactggca acgaggcgac ccttgcagca tgcacctcca atggctgggg cgtcactgac 780
tgcaagcaca cggaggatgt cggtgtggtg tgcagcgaca aaaggattcc tgggttcaaa 840
tttgacaatt cgttgatcaa ccagatagag aacctgaata tccaggtgga ggacattcgg 900
attcgagcca tcctctcaac ctaccgcaag cgcaccccag tgatggaggg ctacgtggag 960
gtgaaggagg gcaagacctg gaagcagatc tgtgacaagc actggacggc caagaattcc 1020
cgcgtggtct gcggcatgtt tggcttccct ggggagagga catacaatac caaagtgtac 1080
aaaatgtttg cctcacggag gaagcagcgc tactggccat tctccatgga ctgcaccggc 1140
acagaggccc acatctccag ctgcaagctg ggcccccagg tgtcactgga ccccatgaag 1200
aatgtcacct gcgagaatgg gctaccggcc gtggtgagtt gtgtgcctgg gcaggtcttc 1260
agccctgacg gaccctcaag attccggaaa gcgtacaagc cagagcaacc cctggtgcga 1320
ctgagaggcg gtgcctacat cggggagggc cgcgtggagg tgctcaaaaa tggagaatgg 1380
gggaccgtct gcgacgacaa gtgggacctg gtgtcggcca gtgtggtctg cagagagctg 1440
ggctttggga gtgccaaaga ggcagtcact ggctcccgac tggggcaagg gatcggaccc 1500
atccacctca acgagatcca gtgcacaggc aatgagaagt ccattataga ctgcaagttc 1560

-continued

```
aatgccgagt ctcagggctg caaccacgag gaggatgctg gtgtgagatg caacacccct   1620
gccatgggct tgcagaagaa gctgcgcctg aacggcggcc gcaatcccta cgagggccga   1680
gtggaggtgc tggtggagag aaacgggtcc cttgtgtggg ggatggtgtg tggccaaaac   1740
tggggcatcg tggaggccat ggtggtctgc cgccagctgg gcctgggatt cgccagcaac   1800
gccttccagg agacctggta ttggcacgga gatgtcaaca gcaacaaagt ggtcatgagt   1860
ggagtgaagt gctcgggaac ggagctgtcc ctggcgcact gccgccacga cggggaggac   1920
gtggcctgcc cccagggcgg agtgcagtac ggggccggag ttgcctgctc agaaaccgcc   1980
cctgacctgg tcctcaatgc ggagatggtg cagcagacca cctacctgga ggaccggccc   2040
atgttcatgc tgcagtgtgc catggaggag aactgcctct cggcctcagc cgcgcagacc   2100
gaccccacca cgggctaccg ccggctcctg cgcttctcct cccagatcca caacaatggc   2160
cagtccgact tccggcccaa gaacggccgc cacgcgtgga tctggcacga ctgtcacagg   2220
cactaccaca gcatggaggt gttcacccac tatgacctgc tgaacctcaa tggcaccaag   2280
gtggcagagg gccacaaggc cagcttctgc ttggaggaca cagaatgtga aggagacatc   2340
cagaagaatt acgagtgtgc caacttcggc gatcagggca tcaccatggg ctgctgggac   2400
atgtaccgcc atgacatcga ctgccagtgg gttgacatca ctgacgtgcc ccctggagac   2460
tacctgttcc aggttgttat taaccccaac ttcgaggttg cagaatccga ttactccaac   2520
aacatcatga aatgcaggag ccgctatgac ggccaccgca tctggatgta caactgccac   2580
ataggtggtt ccttcagcga agagacggaa aaaaagtttg agcacttcag cgggctctta   2640
aacaaccagc tgtccccgca gtaaagaagc ctgcgtggtc aactcctgtc ttcaggccac   2700
accacatctt ccatgggact tccccccaac aactgagtct gaacgaatgc cacgtgccct   2760
cacccagccc ggcccccacc ctgtccagac ccctacagct gtgtctaagc tcaggaggaa   2820
agggaccctc ccatcattca tggggggctg ctacctgacc cttggggcct gagaaggcct   2880
tgcggggggtg gggtttgtcc acagagctgc tggagcagca ccaagagcca gtcttgaccg   2940
ggatgaggcc cacagacagg ttgtcatcag cttgtcccat tcaagccacc gagctcacca   3000
cagacacagt ggagccgcgc tcttctccag tgacacgtgg acaaatgcgg gctcatcagc   3060
ccccccagag agggtcaggc cgaaccccat ttctcctcct cttaggtcat tttcagcaaa   3120
cttgaatatc tagacctctc ttccaatgaa accctccagt ctattatagt cacatagata   3180
atggtgccac gtgttttctg atttggtgag ctcagacttg gtgcttccct atccacagcc   3240
cccacccctt gtttttcaag atactattat tatattttca cagacttttg aagcacaaat   3300
ttattggcat ttaatattgg acatctgggc ccttggaagt acaaatctaa ggaaaaacca   3360
acccactgtg taagtgactc atcttcctgt tgttccaatt ctgtgggttt ttgattcaac   3420
ggtgctataa ccagggtcct gggtgacagg gcgctcactg agcaccatgt gtcatcacag   3480
acacttacac atacttgaaa cttggaataa aagaaagatt tatgaaacgt gtctgtgttt   3540
cctttgaccc acagcacctg ggccctgagc agcaggcttc ctatgttcag tggccagaag   3600
cagagcttca ggtacattcg tggttttctc cggtggacat gggtcctcag atcccctcca   3660
gcccagtgtg gccaccaggg cacctccttc aatagactcc aaaaggggca gctcctacca   3720
tctgggagaa gcaatctaag gagatcacaa aaagtaacgg aacaggagtc ataatctttc   3780
ttgaactcct gtggttttta ctgaaacttg                                    3810
```

<210> SEQ ID NO 23
<211> LENGTH: 5496

<212> TYPE: DNA
<213> ORGANISM: homo sapiens

<400> SEQUENCE: 23
ctgtggcttg ccccagagct gatccttgtc tttgtccact tctcagcgag gatggcactt 60
cagggagccc ttcccttact atcgcagaga gagcaggccc tccccagtca tgtccaaccc 120
agaactctgt tttgttttct tcatagccct agcatcacag aaaatcaccc tgtgcattca 180
tggatgtcca cgggggcaag ggctttgtgt tgcttaaccc agcatcctga accgtgtttg 240
ttgaatgaat acagaacccc gtttgctctg ggagagcaca gaaaacagtc ttctatcata 300
tatcatagcc agctgcaaac agcagatggc ttcccatatc ccagagagta agaaccagag 360
agagagagaa agagagagag tttgggtctt tctcctctgt gcctgctctc tccagagaaa 420
ctggaggggt agcagttagc attcccccgc tggttccacc aagcacagtc aaggtctcta 480
ggacatggcc acccctcacc tgtggaagcg gtcctgctgg ggtgggtggg tgttagttgg 540
ttctggtttg ggtcagagac acccagtggc ccaggtgggc gtggggccag ggcgcagacg 600
agaaggggca cgagggctcc gctccgagga cccagcggca agcaccggtc ccgggcgcgc 660
cccagcccac ccactcgcgt gcccacggcg gcattattcc ctataaggat ctgaacgatc 720
cgggggcggc cccgccccgt taccccttgc ccccggcccc gccccctttt tggagggccg 780
atgaggtaat gcggctctgc cattggtctg agggggcggg ccccaacagc ccgaggcggg 840
gtccccgggg gcccagcgct atatcactcg gccgcccagg cagcggcgca gagcgggcag 900
caggcaggcg gcgggcgctc agacggcttc tcctcctcct cttgctcctc cagctcctgc 960
tccttcgccg ggaggccgcc cgccgagtcc tgcgccagcg ccgaggcagc ctcgctgcgc 1020
cccatcccgt cccgccgggc actcggaggg cagcgcgccg gaggccaagg ttgccccgca 1080
cggcccggcg ggcgagcgag ctcgggctgc agcagccccg ccggcggcgc gcacggcaac 1140
tttggagagg cgagcagcag ccccggcagc ggcggcagca gcggcaatga ccccttggct 1200
cgggctcatc gtgctcctgg gcagctggag cctgggggac tggggcgccg aggcgtgcac 1260
atgctcgccc agccaccccc aggacgcctt ctgcaactcc gacatcgtga tccgggccaa 1320
ggtggtgggg aagaagctgg taaaggaggg gcccttcggc acgctggtct acaccatcaa 1380
gcagatgaag atgtaccgag gcttcaccaa gatgccccat gtgcagtaca tccatacgga 1440
agcttccgag agtctctgtg gccttaagct ggaggtcaac aagtaccagt acctgctgac 1500
aggtcgcgtc tatgatggca agatgtacac ggggctgtgc aacttcgtgg agaggtggga 1560
ccagctcacc ctctcccagc gcaaggggct gaactatcgg tatcacctgg gttgtaactg 1620
caagatcaag tcctgctact acctgccttg ctttgtgact tccaagaacg agtgtctctg 1680
gaccgacatg ctctccaatt tcggttaccc tggctaccag tccaaacact acgcctgcat 1740
ccggcagaag ggcggctact gcagctggta ccgaggatgg gcccccccgg ataaaagcat 1800
catcaatgcc acagacccct gagcgccaga ccctgcccca cctcacttcc ctcccttccc 1860
gctgagcttc ccttggacac taactcttcc cagatgatga caatgaaatt agtgcctgtt 1920
ttcttgcaaa tttagcactt ggaacattta aagaaaggtc tatgctgtca tatggggttt 1980
attgggaact atcctcctgg ccccaccctg ccccttcttt ttggttttga catcattcat 2040
ttccacctgg gaatttctgg tgccatgcca gaaagaatga ggaacctgta ttcctcttct 2100
tcgtgataat ataatctcta tttttttagg aaaacaaaaa tgaaaaacta ctccatttga 2160
ggattgtaat tcccacccct cttgcttctt ccccacctca ccatctccca gaccctcttc 2220

```
cctttgccct tctcctccaa tacataaagg acacagacaa ggaacttgct gaaaggccaa   2280
ccatttcagg atcagtcaaa ggcagcaagc agatagactc aaggtgtgtg aaagatgtta   2340
tacaccagga gctgccactg catgtcccaa ccagactgtg tctgtctgtg tctgcatgta   2400
agagtgaggg agggaaggaa ggaactacaa gagagtcgga gatgatgcag cacacacaca   2460
attccccagc ccagtgatgc ttgtgttgac cagatgttcc tgagtctgga gcaagcaccc   2520
aggccagaat aacagagctt tcttagttgg tgaagactta aacatctgcc tgaggtcagg   2580
aggcaatttg cctgccttgt acaaaagctc aggtgaaaga ctgagatgaa tgtctttcct   2640
ctccctgcct cccaccagac ttcctcctgg aaaacgcttt ggtagatttg gccaggagct   2700
ttcttttatg taaattggat aaatacacac accatacact atccacagat atagccaagt   2760
agatttgggt agaggatact atttccagaa tagtgtttag ctcacctagg gggatatgtt   2820
tgtatacaca tttgcatata cccacatggg gacataagct aattttttta caggacacag   2880
aattctgttc aatgctgtta aatatgccaa tagtttaatc tcttctattt tgttgtcgtt   2940
gcttgtttga agaaaatcat gacattccaa gttgacattt tttttcatt ttaattaaaa   3000
tttgaaattc tgaacaccgt cagcaccctc tcttccctat catgggtcat ctgacccctg   3060
tccgtctcct tgtccctgct tcatgtttgg gggcctttct ttaactgcct tcctggctta   3120
gctcagatgg cagatgagag tgtagtcaag ggcctgggca caggagggag agctgcagag   3180
tgtcctgcct gccttggctg gagggacacc tctcctgggt gtggagacag cttggttccc   3240
tttccctagc tccctggtgg gtgaatgcca cctcctgaga tcctcacctc ttggaattaa   3300
aattgttggt cactggggaa agcctgagtt tgcaaccagt tgtagggttt ctgttgtgtt   3360
ttttttttt tttttgaaat aaaactataa tataaattct cctattaaat aaaattattt   3420
taagttttag tgtcaaaagt gagatgctga gagtaggtga taatgtatat tttacagagt   3480
gggggttggc aggatggtga cattgaacat gattgctctc tgtctctttt ttcagcttat   3540
gggtatttat cttctattag tatttgtatc ttcagttcat tccactttag gaaacagagc   3600
tgccaattga aacagaagaa gaaaaaaaaa aaaagcagca gacaacacac tgtagagtct   3660
tgcacacaca caagtgccca ggcaaggtgc ttggcagaac cgcagagtgg gaagagagta   3720
ccggcatcgg gtttccttgg gatcaatttc attaccgtgt acctttccca ttgtggtcat   3780
gccatttggc agggggagaa tgggaggctt ggccttcttt gtgaggcagt gtgagcagaa   3840
gctgatgcca gcatgtcact ggttttgaag ggatgagccc agacttgatg ttttgggatt   3900
gtccttattt taacctcaag gtctcgcatg gtggggcccc tgaccaacct acacaagttc   3960
cctcccacaa gtggacatca gtgtcttctc tgtgaggcat ctggccattc gcactccctg   4020
gtgtggtcag cctctctcac acaaggagga acttgggtga aggctgagtg tgaggcacct   4080
gaagtttccc tgcggagtcg ataaattagc agaaccacat ccccatctgt taggccttgg   4140
tgaggaggcc ctgggcaaag aagggtcttt cgcaaagcga tgtcagaggg cggttttgag   4200
ctttctataa gctatagctt tgtttatttc acccgttcac ttactgtata atttaaaatc   4260
atttatgtag ctgagacact tctgtatttc aatcatatca tgaacatttt attttgctaa   4320
atcttgtgtc atgtgtaggc tgtaatatgt gtacattgtg tttaagagaa aaatgaaacc   4380
cacatgccgc cattttcctg aatcaaattc tgcagtggaa tggagaggaa aatacttcta   4440
ggcaagcagc tagactggtg aattggggga aatagaagga actagtaact gagactcctc   4500
cagcctcctc cctattggaa tcccaatggc tcctggagta ggaaaaaagt ttaaactaca   4560
ttcatgttct tgttctgtgt cactcggccc tgggtagtct accatttact tcaccccaag   4620
```

```
tcctgctgcc catccagttg ggaagccatg attttcctaa gaatccaggg ccatgggaga   4680

tacaattcca agttctcgct tcctcctttg ggcatctctt ctgcctccca atcaaggaag   4740

ctccatgctc aggctctcag ctctcgggcc agtgctctgc tctgtccagg gtaggtaata   4800

ctgggagact cctgtctttt accctcccct cgttccagac ctgcctcatg gtggcaacat   4860

ggttcttgaa caattaaaga aacaaatgac tttttggaat agccctgtct agggcaaact   4920

gtggccccca ggagacacta cccttccatg ccccagacct ctgtcttgca tgtgacaatt   4980

gacaatctgg actaccccaa gatggcaccc aagtgtttgg cttctggcta cctaaggtta   5040

acatgtcact agagtatttt tatgagagac aaacattata aaaatctgat ggcaaaagca   5100

aaacaaaatg gaaagtaggg gaggtggatg tgacaacaac ttccaaattg gctctttgga   5160

ggcgagagga aggggagaac ttggagaata gtttttgctt tgggggtaga ggcttcttag   5220

attctcccag catccgcctt tccctttagc cagtctgctg tcctgaaacc cagaagtgat   5280

ggagagaaac caacaagaga tctcgaaccc tgtctagaag gaatgtattt gttgctaaat   5340

ttcgtagcac tgtttacagt tttcctccat gttatttatg aattttatat tccgtgaatg   5400

tatattgtct tgtaatgttg cataatgttc actttttata gtgtgtcctt tattctaaac   5460

agtaaagtgg ttttatttct atcacaaaaa aaaaaa                             5496
```

<210> SEQ ID NO 24
<211> LENGTH: 2371
<212> TYPE: DNA
<213> ORGANISM: homo sapiens

<400> SEQUENCE: 24

```
attcattcag agtgggaaag cgccagccga gcggccagcc agtgcggggc tggccatgta     60

aggcccacag gcggtcctgc ccgcccggtg ccctgcggag agcctcgtgc agccctgggc    120

accgcccctg ccctgccctg accccttggc cttgaaatgc tgtcatcgga ggagccgtcc    180

cgctcgggac aaggccagca tggacaaagc tagagctggg gcaagcaagg agccttcctg    240

tcctcgaggc cgtgggaaga gaagcacgcc caggggggcca ctcctgagag cctctctgtc   300

caccaggcct ctgcagaggg gtcaccatgg ctctggcccg aggcagccgg cagctggggg    360

ccctggtgtg gggcgcctgc ctgtgcgtgc tggtgcacgg gcagcaggcg cagcccgggc    420

agggctcgga ccccgcccgc tggcggcagc tgatccagtg ggagaacaac gggcaggtgt    480

acagcttgct caactcgggc tcagagtacg tgccggccgg acctcagcgc tccgagagta    540

gctcccgggt gctgctggcc ggcgcgcccc aggcccagca gcggcgcagc cacgggagcc    600

cccggcgtcg gcaggcgccg tccctgcccc tgccggggcg cgtgggctcg gacaccgtgc    660

gcggccaggc gcggcaccca ttcggctttg gccaggtgcc cgacaactgg cgcgaggtgg    720

ccgtcgggga cagcacgggc atggcccggg cccgcacctc cgtctcccag caacggcacg    780

ggggctccgc ctcctcggtc tcggcttcgg ccttcgccag cacctaccgc cagcagccct    840

cctacccgca gcagttcccc tacccgcagg cgcccttcgt cagccagtac gagaactacg    900

accccgcgtc gcggacctac gaccagggtt tcgtgtacta ccggcccgcg ggcggcggcg    960

tgggcgcggg ggcggcggcc gtggcctcgg cgggggtcat ctacccctac cagccccggg   1020

cgcgctacga ggagtacggc ggcggcgaag agctgcccga gtacccgcct cagggcttct   1080

acccggcccc cgagaggccc tacgtgccgc cgccgccgcc gccccccgac ggcctggacc   1140

gccgctactc gcacagtctg tacagcgagg gcacccccgg cttcgagcag gcctaccctg   1200
```

accccggtcc cgaggcggcg caggcccatg gcggagaccc acgcctgggc tggtacccgc 1260
cctacgccaa cccgccgccc gaggcgtacg ggccgccgcg cgcgctggag ccgccctacc 1320
tgccggtgcg cagctccgac acgcccccgc cgggtgggga gcggaacggc gcgcagcagg 1380
gccgcctcag cgtgggcagc gtgtaccggc ccaaccagaa cggccgcggt ctccctgact 1440
tggtcccaga ccccaactat gtgcaagcat ccacttatgt gcagagagcc cacctgtact 1500
ccctgcgctg tgctgcggag gagaagtgtc tggccagcac agcctatgcc cctgaggcca 1560
ccgactacga tgtgcgggtg ctactgcgct tcccccagcg cgtgaagaac cagggcacag 1620
cagacttcct ccccaaccgg ccacggcaca cctgggagtg gcacagctgc caccagcatt 1680
accacagcat ggacgagttc agccactacg acctactgga tgcagccaca ggcaagaagg 1740
tggccgaggg ccacaaggcc agtttctgcc tggaggacag cacctgtgac ttcggcaacc 1800
tcaagcgcta tgcatgcacc tctcataccc agggcctgag cccaggctgc tatgacacct 1860
acaatgcgga catcgactgc cagtggatcg acataaccga cgtgcagcct gggaactaca 1920
tcctcaaggt gcacgtgaac ccaaagtata ttgttttgga gtctgacttc accaacaacg 1980
tggtgagatg caacattcac tacacaggtc gctacgtttc tgcaacaaac tgcaaaattg 2040
tccaatcctg atctccggga gggacagatg gccaatctct cccctccaa agcaggccct 2100 gctccccggg cagcctcccg ccgaggggcc cagcccccaa cccacaggca cggaggggca 2160
tccctccctg ccggcctcag ggagcgaacg tggatgaaaa ccacagggat tccggacgcc 2220
agaccccatt ttatacttca cttttctcta cagtgttgtt ttgttgttgt tggtttttat 2280
tttttatact ttggccatac cacagagcta gattgcccag gtctgggctg aataaaacaa 2340
ggtttttcta ctctgaaaaa aaaaaaaaaa a 2371

<210> SEQ ID NO 25
<211> LENGTH: 3316
<212> TYPE: DNA
<213> ORGANISM: homo sapiens

<400> SEQUENCE: 25
gcggaaaaga gcctcgggcc aggagcgcag gaaccagacc gtgtcccgcg gggctgtcac 60
ctccgcctct gctccccgac ccggccatgc gcggcctcgg gctctggctg ctgggcgcga 120
tgatgctgcc tgcgattgcc cccagccggc cctgggccct catggagcag tatgaggtcg 180
tgttgccgtg gcgtctgcca ggcccccgag tccgccgagc tctgccctcc cacttgggcc 240
tgcacccaga gagggtgagc tacgtccttg gggccacagg gcacaacttc accctccacc 300
tgcggaagaa cagggacctg ctgggctccg gctacacaga gacctatacg gctgccaatg 360
gctccgaggt gacggagcag cctcgcgggc aggaccactg cttctaccag ggccacgtag 420
aggggtaccc ggactcagcc gccagcctca gcacctgtgc cggcctcagg ggtttcttcc 480
aggtggggtc agacctgcac ctgatcgagc ccctggatga aggtggcgag ggcggacggc 540
acgccgtgta ccaggctgag cacctgctgc agacggccgg gacctgcggg gtcagcgacg 600
acagcctggg cagcctcctg ggaccccgga cggcagccgt cttcaggcct cggcccgggg 660
actctctgcc atcccgagag acccgctacg tggagctgta tgtggtcgtg gacaatgcag 720
agttccagat gctggggagc gaagcagccg tgcgtcatcg ggtgctggag gtggtgaatc 780
acgtggacaa gctatatcag aaactcaact tccgtgtggt cctggtgggc ctggagattt 840
ggaatagtca ggacaggttc cacgtcagcc ccgaccccag tgtcacactg gagaacctcc 900
tgacctggca ggcacggcaa cggacacggc ggcacctgca tgacaacgta cagctcatca 960

```
cgggtgtcga cttcaccggg actaccgtgg ggtttgccag ggtgtccgcc atgtgctccc   1020
acagctcagg ggctgtgaac caggaccaca gcaagaaccc cgtgggcgtg gcctgtacca   1080
tggcccatga gatgggccac aacctgggca tggaccatga tgagaacgtc cagggctgcc   1140
gctgccagga acgcttcgag gccggccgct gcatcatggc gggcagcatt ggctccagtt   1200
tccccaggat gttcagtgac tgcagccagg cctacctgga gagctttttg gagcggccgc   1260
agtcggtgtg cctcgccaac gcccctgacc tcagccacct ggtgggcggc cccgtgtgtg   1320
ggaacctgtt tgtggagcgt ggggagcagt gcgactgcgg ccccccgag gactgccgga    1380
accgctgctg caactctacc acctgccagc tggctgaggg ggcccagtgt gcgcacggta   1440
cctgctgcca ggagtgcaag gtgaagccgg ctggtgagct gtgccgtccc aagaaggaca   1500
tgtgtgacct cgaggagttc tgtgacggcc ggcaccctga gtgcccggaa gacgccttcc   1560
aggagaacgg cacgccctgc tccgggggct actgctacaa cggggcctgt cccacactgg   1620
cccagcagtg ccaggccttc tgggggccag gtgggcaggc tgccgaggag tcctgcttct   1680
cctatgacat cctaccaggc tgcaaggcca gccggtacag ggctgacatg tgtggcgttc   1740
tgcagtgcaa gggtgggcag cagcccctgg ggcgtgccat ctgcatcgtg gatgtgtgcc   1800
acgcgctcac cacagaggat ggcactgcgt atgaaccagt gcccgagggc acccggtgtg   1860
gaccagagaa ggtttgctgg aaaggacgtt gccaggactt acacgtttac agatccagca   1920
actgctctgc ccagtgccac aaccatgggg tgtgcaacca caagcaggag tgccactgcc   1980
acgcgggctg ggccccgccc cactgcgcga agctgctgac tgaggtgcac gcagcgtccg   2040
ggagcctccc cgtcttcgtg gtggtggttc tggtgctcct ggcagttgtg ctggtcaccc   2100
tggcaggcat catcgtctac cgcaaagccc ggagccgcat cctgagcagg aacgtggctc   2160
ccaagaccac aatggggcgc tccaaccccc tgttccacca ggctgccagc cgcgtgccgg   2220
ccaagggcgg ggctccagcc ccatccaggg gcccccaaga gctggtcccc accacccacc   2280
cgggccagcc cgcccgacac ccggcctcct cggtggctct gaagaggccg cccccctgctc  2340
ctccggtcac tgtgtccagc ccacccttcc cagttcctgt ctacacccgg caggcaccaa   2400
agcaggtcat caagccaacg ttcgcacccc cagtgccccc agtcaaaccc ggggctggtg   2460
cggccaaccc tggtccagct gagggtgctg ttggcccaaa ggttgccctg aagcccccca   2520
tccagaggaa gcaaggagcc ggagctccca cagcacccta gggggcacc tgcgcctgtg    2580
tggaaatttg gagaagttgc ggcagagaag ccatgcgttc cagcattcca cggtccagct   2640
agtgccgctc agccctagac cctgactttg caggctcagc tgctgttcta acctcaggaa   2700
tgcatctacc tgagaggctc ctgctgtcca cgccctcagc caattccttc tccccgcctt   2760
ggccacgtgt agccccagct gtctgcaggc accaggctgg gatgagctgt gtgcttgcgg   2820
gtgcgtgtgt gtgtacgtgt ctccaggtgg ccgctggtct cccgctgtgt tcaggaggcc   2880
acatatacag cccctcccag ccacacctgc ccctgctctg ggcctgctg agccggctgc    2940
cctgggcacc cggttccagg cagcacagac gtggggcatc cccagaaaga ctccatccca   3000
ggaccaggtt cccctgcgtg ctcttcgaga gggtgtcagt gagcagactg caccccaagc   3060
tcccgactcc aggtcccctg atcttggggc ctgtttccca tgggattcaa gagggacagc   3120
cccagctttg tgtgtgttta agcttaggaa tcgcctttat ggaaagggct atgtgggaga   3180
gtcagctatc ttgtctggtt ttcttgagac ctcagatgtg tgttcagcag ggctgaaagc   3240
ttttattctt taataatgag aaatgtatat tttactaata aattattgac cgagttctgt   3300
```

-continued

```
aaaaaaaaaa aaaaaa                                                 3316


<210> SEQ ID NO 26
<211> LENGTH: 1984
<212> TYPE: DNA
<213> ORGANISM: homo sapiens

<400> SEQUENCE: 26

ctgatttaca ggaactcaca ccagcgatca atcttcctta atttgtaact gggcagtgtc     60

ccgggccagc caatagctaa gactgccccc cccgcacccc accctccctg accctggggg    120

actctctact cagtctgcac tggagctgcc tggtgaccag aagtttggag tccgctgacg    180

tcgccgccca gatggcctcc aggctgaccc tgctgaccct cctgctgctg ctgctggctg    240

gggatagagc ctcctcaaat ccaaatgcta ccagctccag ctcccaggat ccagagagtt    300

tgcaagacag aggcgaaggg aaggtcgcaa caacagttat ctccaagatg ctattcgttg    360

aacccatcct ggaggtttcc agcttgccga caaccaactc aacaaccaat tcagccacca    420

aaataacagc taataccact gatgaaccca ccacacaacc caccacagag cccaccaccc    480

aacccaccat ccaacccacc caaccaacta cccagctccc aacagattct cctacccagc    540

ccactactgg gtccttctgc ccaggacctg ttactctctg ctctgacttg gagagtcatt    600

caacagaggc cgtgttgggg gatgctttgg tagatttctc cctgaagctc taccacgcct    660

tctcagcaat gaagaaggtg gagaccaaca tggccttttc cccattcagc atcgccagcc    720

tccttaccca ggtcctgctc ggggctgggg agaacaccaa aacaaacctg gagagcatcc    780

tctcttaccc caaggacttc acctgtgtcc accaggccct gaagggcttc acgaccaaag    840

gtgtcacctc agtctctcag atcttccaca gcccagacct ggccataagg gacacctttg    900

tgaatgcctc tcggaccctg tacagcagca gccccagagt cctaagcaac aacagtgacg    960

ccaacttgga gctcatcaac acctgggtgg ccaagaacac caacaacaag atcagccggc   1020

tgctagacag tctgccctcc gatacccgcc ttgtcctcct caatgctatc tacctgagtg   1080

ccaagtggaa gacaacattt gatcccaaga aaaccagaat ggaacccttt cacttcaaaa   1140

actcagttat aaaagtgccc atgatgaata gcaagaagta ccctgtggcc catttcattg   1200

accaaacttt gaaagccaag gtggggcagc tgcagctctc ccacaatctg agtttggtga   1260

tcctggtacc ccagaacctg aaacatcgtc ttgaagacat ggaacaggct ctcagccctt   1320

ctgttttcaa ggccatcatg gagaaactgg agatgtccaa gttccagccc actctcctaa   1380

cactaccccg catcaaagtg acgaccagcc aggatatgct ctcaatcatg gagaaattgg   1440

aattcttcga tttttcttat gaccttaacc tgtgtgggct gacagaggac ccagatcttc   1500

aggtttctgc gatgcagcac cagacagtgc tggaactgac agagactggg gtggaggcgg   1560

ctgcagcctc cgccatctct gtggcccgca ccctgctggt ctttgaagtg cagcagccct   1620

tcctcttcgt gctctgggac cagcagcaca agttccctgt cttcatgggg cgagtatatg   1680

accccagggc ctgagacctg caggatcagg ttagggcgag cgctacctct ccagcctcag   1740

ctctcagttg cagccctgct gctgcctgcc tggacttggc ccctgccacc tcctgcctca   1800

ggtgtccgct atccaccaaa agggctccct gagggtctgg gcaagggacc tgcttctatt   1860

agcccttctc catggccctg ccatgctctc caaaccactt tttgcagctt tctctagttc   1920

aagttcacca gactctataa ataaaacctg acagaccatg actttcaaaa aaaaaaaaaa   1980

aaaa                                                              1984
```

<210> SEQ ID NO 27
<211> LENGTH: 2592
<212> TYPE: DNA
<213> ORGANISM: homo sapiens

<400> SEQUENCE: 27
catccgtgcg tctgtggaag gctgcgtttc cggcctgaga aaccgtcatg tttctgggga 60
gtcacctcag ctggcagtta ccaccgtgtt agaaagcagc ctcaggaccg gccacctcca 120
tcactggcgt caccatgggg gctgtgctgg gtgtcttctc cctcgccagc tgggttccat 180
gcctctgcag cggtgcctca tgtttgctgt gtagttgctg tcctaacagt aagaattcca 240
cggtgactcg cctcatttat gctttcattc tcctcctgag cactgtcgta tcctatatca 300
tgcagagaaa agagatggaa acttacttga agaagattcc tggattttgt gaagggggat 360
ttaaaatcca tgaggctgat ataaatgcag ataaagattg tgatgtgctg gttggttata 420
aagctgtgta tcggatcagc tttgccatgg ccatcttttt ctttgtcttt tctctgctca 480
tgttcaaagt aaaaacaagt aaagatctcc gagcggcagt acacaatggg ttttggttct 540
tcaaaattgc tgcccttatt ggaatcatgg ttggctcttt ctacatccct gggggctatt 600
tcagctcagt ctggtttgtt gttggcatga taggggccgc cctcttcatc ctcattcagc 660
tggtgctgct ggtagatttt gctcattctt ggaatgaatc atgggtaaat cgaatggaag 720
aaggaaaccc aaggttgtgg tatgctgctt tactgtcttt cacaagcgcc ttttatatcc 780
tgtcaatcat ctgtgtcggg ctgctctata catattacac caaaccagat ggctgcacag 840
aaaacaagtt cttcatcagt attaacctga tcctttgcgt tgtggcttct attatatcga 900
tccacccaaa aattcaggaa caccagcctc gctccggcct cttgcagtcc tccctcatca 960
ccctctacac tatgtacctc acctggtcag ccatgtccaa tgaacctgat cgttcctgca 1020
atcccaacct gatgagcttt attacacgca taactgcacc aaccctggct cctggaaatt 1080
caactgctgt ggtccctacc cctactccac catcaaagag tgggtcttta ctggattcag 1140
ataattttat tggactgttt gtctttgttc tctgcctctt gtattctagc atccgcactt 1200
ccactaatag ccaagtagac aagctgaccc tgtcagggag tgacagcgtc atccttggtg 1260
atacaactac cagtggtgcc agtgatgaag aagatggaca gcctcggcgg gctgtggaca 1320
acgagaaaga gggagtgcag tatagctact ccttattcca cctcatgctc tgcttggctt 1380
ccttgtacat catgatgacc ctgaccagct ggtacagccc tgatgcaaag tttcagagca 1440
tgaccagcaa gtggccagct gtgtgggtca agatcagctc cagctgggtc tgcctcctgc 1500
tttacgtctg gacccttgtg gctccacttg tcctcaccag tcgggacttc agctgaacct 1560
ctgagtgcca aggacaccac tggaactcac aaaggtctcc ttcaccgaaa acccatatac 1620
cttttaagtt tgtttcaact aaaatattaa gtgaatgctt tgcaagtttg actgtatgca 1680
ggtttatatc agaaggtgag attgaataat gcttgatgca gaatcgaaac ttctcattta 1740
tctgtatatt atgtttactt ctaaggatat agcacaaagg gaacattttt tgtttaaagt 1800
gaactacagc tgtgctgtga agagagttct ttataaagcc tgtaggttct tttaactttg 1860
gtttaaaatg taagatagga aaatgttgga tatttgaggc catgcttaat atatttatat 1920
tgcagtatcc tttaaaagca aaaaaaaaaa aatgcattta tattacagtt ttcctctatg 1980
aaagtcctta cttatatgat acaagcactg tgttttgtgc ttaaactctt cagcggggta 2040
gcatcaaagt tcttggggaa ggatcgtata tgtgggtccc ttccctagaa gaatggttgc 2100
tgatatggct actgcttcta catcttgagt tttttaattt actttttta cactgtagca 2160

-continued

```
ttgagactgc ttgattcaag tctggtgctt tgccagatgt attaatttcc ataaatgctt   2220

tgtgagtttg gttaaaatga agattcactt gggaaaacac tgcagcttta gtctgtgtta   2280

ctatcttgtt atgagtatgt aaaagtaaaa tgcatgtgaa tttatcatat ttgcactatg   2340

aaggtatttg gttaaaatac aaagactttt aagattttaa ggccctttct tccaacagct   2400

tttatagtta gcagccattc tttattttct ggatagccag gttttatcac gcttctagtc   2460

aggatgctcc tattccttct aaaaattacg gtctgactag tgagcaaagt cttgaattta   2520

ttcaaaagtc ctaaatacct tctctaggta agacacttgg tagatgagag acggaaggca   2580

ttgtcaagaa cc                                                        2592


<210> SEQ ID NO 28
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 28

agcactgggt gtttgacg                                                    18


<210> SEQ ID NO 29
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 29

gtcttcccat tgggcatc                                                    18


<210> SEQ ID NO 30
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 30

cagacgtggg tcgattcc                                                    18


<210> SEQ ID NO 31
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 31

tcatcgatca tgtctcgc                                                    18


<210> SEQ ID NO 32
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 32

gcagcgcttc ttcagctt                                                    18


<210> SEQ ID NO 33
<211> LENGTH: 18
```

<212> TYPE: DNA
<213> ORGANISM: Artificial sequence
<220> FEATURE:
<223> OTHER INFORMATION: Single strand DNA oligonucleotide

<400> SEQUENCE: 33
gtgtgtgtcc acttggga 18

<210> SEQ ID NO 34
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 34
acgatgatga ccggaagt 18

<210> SEQ ID NO 35
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 35
gtgtagatcg gggccatc 18

<210> SEQ ID NO 36
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 36
gcagtgattt ccccgcca 18

<210> SEQ ID NO 37
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 37
gggggccatc atggtatc 18

<210> SEQ ID NO 38
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 38
aaggaggcag cagagaac 18

<210> SEQ ID NO 39
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 39
gcactgtcat gcaatggg 18

<210> SEQ ID NO 40
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 40
gcctaccaga tcatccac 18

<210> SEQ ID NO 41
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 41
acatctgtgc cgttaggt 18

<210> SEQ ID NO 42
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 42
acaacactct tgacgctg 18

<210> SEQ ID NO 43
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 43
cgagagtggg gcttgact 18

<210> SEQ ID NO 44
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 44
acaaccagtt cgccatgg 18

<210> SEQ ID NO 45
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 45
aagcggggtg aaacgttcc 19

<210> SEQ ID NO 46
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 46
gaccratcct gtcactgac 19

<210> SEQ ID NO 47
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 47
tgcagtcctc gctcactggg cacg 24

<210> SEQ ID NO 48
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 48
ggtgagtaac gcgtaggtaa 20

<210> SEQ ID NO 49
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 49
acgatccgaa aaccttcttc 20

<210> SEQ ID NO 50
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 50
tctaggagtc ccagtcagcc 20

<210> SEQ ID NO 51
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 51
caacaaggac tgccaagcac 20

<210> SEQ ID NO 52
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 52
gcccttgagc taggactgga 20

<210> SEQ ID NO 53
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 53
tacggccaaa tccgttcaca 20

<210> SEQ ID NO 54
<211> LENGTH: 117
<212> TYPE: PRT
<213> ORGANISM: Artificial Sequence
<220> FEATURE:
<223> OTHER INFORMATION: LEM-2/15.8 antibody VL amino acid sequence

<400> SEQUENCE: 54

```
Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Ile Phe Ser Asn Tyr
            20                  25                  30

Ala Met Ser Trp Val Arg Gln Thr Pro Glu Lys Arg Leu Glu Trp Val
        35                  40                  45

Ala Thr Ile Ser Gly Gly Gly Arg Asn Ile Tyr Ser Leu Asp Ser Val
    50                  55                  60

Lys Gly Arg Phe Thr Phe Phe Arg Asp Asn Ala Arg Asn Thr Leu Tyr
65                  70                  75                  80

Leu Gln Met Ser Ser Leu Arg Ser Glu Asp Thr Ala Met Tyr Phe Cys
                85                  90                  95

Ser Arg Glu Asn Tyr Gly Ser Ser Phe Thr Tyr Trp Gly Gln Gly Thr
            100                 105                 110

Leu Val Thr Val Ser
        115
```

<210> SEQ ID NO 55
<211> LENGTH: 116
<212> TYPE: PRT
<213> ORGANISM: Artificial Sequence
<220> FEATURE:
<223> OTHER INFORMATION: LEM-2/15.8 antibody VH amino acid sequence

<400> SEQUENCE: 55

```
Leu Val Ile Asp Val Leu Met Thr Gln Thr Pro Leu Ser Leu Pro Val
1               5                   10                  15

Gly Leu Gly Asp Gln Ala Ser Ile Ser Cys Arg Ser Ser Gln Ser Ile
            20                  25                  30

Val His Ser Asn Gly Asn Thr Tyr Leu Glu Trp Tyr Leu Gln Lys Pro
        35                  40                  45

Gly Gln Ser Pro Lys Leu Leu Ile Tyr Lys Val Ser Asn Arg Phe Ser
    50                  55                  60

Gly Val Pro Asp Arg Phe Ser Gly Ser Gly Ser Gly Thr Asp Phe Thr
65                  70                  75                  80

Leu Lys Ile Ser Arg Val Glu Ala Glu Asp Leu Gly Val Tyr Tyr Cys
                85                  90                  95
```

-continued

```
Phe Gln Gly Ser His Ala Pro Tyr Thr Phe Gly Gly Gly Thr Lys Leu
            100                 105                 110

Glu Ile Lys Arg
        115
```

METHODS OF PREVENTING SECONDARY INFECTIONS

RELATED APPLICATIONS

This application is a continuation of U.S. patent application Ser. No. 15/549,161 filed on Aug. 6, 2017, which is a National Phase of PCT Patent Application No. PCT/IL2016/050156 having International Filing Date of Feb. 9, 2016, which claims the benefit of priority under 35 USC § 119(e) of U.S. Provisional Patent Application No. 62/113,551 filed on Feb. 9, 2015. The contents of the above applications are all incorporated by reference as if fully set forth herein in their entirety.

SEQUENCE LISTING STATEMENT

The ASCII file, entitled 82225SequenceListing.txt, created on Mar. 26, 2020, comprising 121,355 bytes, submitted concurrently with the filing of this application is incorporated herein by reference. The sequence listing submitted herewith is identical to the sequence listing forming part of the international application.

FIELD AND BACKGROUND OF THE INVENTION

The present invention, in some embodiments thereof, relates to a method of preventing secondary infections in subjects infected with a pathogen using agents that down-regulate extracellular matrix remodeling.

Viral pandemics, such as influenza have caused millions of deaths worldwide. An extreme example is the 1918 pandemic which spread to six continents and infected ~500 million people reaching death toll of 50 million. Investigation of clinical cases and autopsy samples indicated that more than 95% of case fatalities were complicated by secondary bacterial infections, most commonly *Streptococcus pneumoniae* (*S. pneumoniae*). Immune cells recruited to the site of infection are critical for influenza clearance. However, growing evidence shows that infiltrating immune cells can also generate excessive inflammatory responses resulting in collateral tissue damage and disruption of the blood-air-barrier.

Tissue tolerance to pathogens is an important evolutionary trade-off, balancing the host immune response to pathogens while maintaining tissue function. However, tolerance capacity differs between various organs; lungs have a relatively low tissue tolerance capacity, and are more vulnerable to tissue damage. Accordingly, it has been argued that during respiratory viral infections uncontrolled host-derived immune responses, rather than viral titers, may be the leading cause of death. These responses are primarily associated with inflammatory monocytes, granulocytes, macrophages and dendritic cells. Accordingly, influenza-infected lungs are diffusely hemorrhagic, potentially linking the host response with tissue destruction. Tissue breaching may prime secondary bacterial invasion coupled with tissue disruption and, in extreme cases, may result in death. The interaction between influenza and secondary bacterial infections has long been studied, yet the molecular mechanisms by which influenza infection primes the tissue to secondary infections are not fully understood.

One of the host's tolerance components is the integrity of respiratory epithelial barriers anchored to the extracellular matrix (ECM). The ECM scaffold is produced by the cells in the tissue and is composed of two layers: I) the interstitial matrix, a three-dimensional gel of polysaccharides and fibrous proteins, and II) the basement membrane, a mesh-like sheet formed at the base of epithelial tissues. ECM turnover is regulated by multiple proteolytic enzymes including matrix metalloproteinases (MMPs) that are responsible for the irreversible cleavage of a plethora of ECM molecules under normal and pathological conditions. Dysregulated proteolytic activity is often associated with inflammation, cancer, and infectious diseases. Accordingly, studies in pathological conditions have shown that dysregulated proteolysis of ECM molecules and related protein fibers have significant effects on tissue function. Specifically, MMPs were shown to play critical roles in lung organogenesis and many MMPs are involved in the acute and chronic phases of lung inflammatory diseases (Greenlee et al., 2007, Physiological reviews 87, 69-98). Several substrates of MMPs have been identified during lung development, including ECM scaffold proteins, cell adhesion molecules, growth factors, cytokines, and chemokines (Greenlee et al., 2007, Physiological reviews 87, 69-98).

Membrane type-I matrix metalloproteinase (MT1-MMP/MMP-14), a membrane tethered collagenase, is a key regulator in development and homeostasis of the lung as well as mediating wound healing, airway remodeling, and cell trafficking. Accordingly, it is expressed by multiple cell populations in the respiratory tract, including fibroblasts, endothelial cells and macrophages (Greenlee et al., 2007, Physiological reviews 87, 69-98). The functions of macrophage-derived proteases during inflammation are typically associated with tissue invasion or degradative events. In macrophages MT1-MMP serves not only as a protease acting on the ECM, but also regulates macrophage immune response. Recruited monocytes and macrophages up-regulate a broad spectrum of ECM remodelers including various MMPs. Depending on the conditions, macrophages express a spectrum of MMPs and their inhibitors: these have been associated with both physiological and pathological lung remodeling events. MMP-9 (gelatinase B) was shown to be beneficial for recovery from influenza infection by promoting migration of neutrophils to the infection site (Bradley et al., 2012, PLoS pathogens 8, e1002641). Despite these important findings, a systematic analysis of ECM proteolytic pathways during respiratory infections, including the trade-off between ECM integrity and immune protection, has never been completed.

Background art includes Cheung et al., Cardiovasc Pathol. 2006 March-April; 15(2):63-74, Elkington et al., 2005 British Society for Immunology, Clinical and Experimental Immunology, 142:12-20; Devy et al., Biochemistry Research International, Volume 2011, Article ID 191670, doi:10.1155/2011/191670; Renckens et al., J Immunol 2006; 176:3735-3741; Vanlaere et al., Clinical Microbiology Reviews, April 2009, Vol 22, p. 224-239 and Udi et al., 2015, Structure 23, 1-12, Jan. 6, 2015.

SUMMARY OF THE INVENTION

According to an aspect of some embodiments of the present invention there is provided a method of treating or preventing a disease associated with a secondary infection in a subject infected with a pathogen comprising administering to the subject a therapeutically effective amount of an anti-pathogenic agent directed towards the pathogen and a therapeutically effective amount of an agent which down-regulates at least one extracellular matrix-associated polypeptide, thereby treating or preventing the disease associated with a secondary infection in the subject.

According to an aspect of some embodiments of the present invention there is provided a method of treating a subject infected with a pathogen comprising administering to the subject a therapeutically effective amount of an anti-pathogenic agent directed towards the pathogen and a therapeutically effective amount of an agent which down-regulates at least one extracellular matrix-associated polypeptide, thereby treating the subject.

According to an aspect of some embodiments of the present invention there is provided an article of manufacture comprising an anti-pathogenic agent and an agent which down-regulates at least one extracellular matrix-associated polypeptide.

According to an aspect of some embodiments of the present invention there is provided a pharmaceutical composition comprising an anti-pathogenic agent as a first active agent, an agent which down-regulates at least one extracellular matrix-associated polypeptide as a second active agent and a pharmaceutically acceptable carrier.

According to an aspect of some embodiments of the present invention there is provided a method of treating influenza in a subject in need thereof comprising administering to the subject a therapeutically effective amount of an agent which down-regulates an extracellular matrix-associated polypeptide, thereby treating the influenza.

According to some embodiments of the invention, the extracellular matrix-associated polypeptide is set forth in Table 1.

According to some embodiments of the invention, the secondary infection is a bacterial infection, a viral infection or a fungal infection.

According to some embodiments of the invention, the secondary infection is a blood infection.

According to some embodiments of the invention, the disease is sepsis.

According to some embodiments of the invention, the administering comprises co-administering.

According to some embodiments of the invention, the pathogen is selected from the group consisting of a virus, a bacteria and a fungus.

According to some embodiments of the invention, the at least one polypeptide is a matrix metalloproteinase (MMP).

According to some embodiments of the invention, the matrix metalloproteinase is selected from the group consisting of membrane type 1-matrix metalloproteinase 1 (MT1-MMP1), MMP-9, MMP-8 and MMP-3.

According to some embodiments of the invention, the at least one polypeptide is membrane type 1-matrix metalloproteinase 1 (MT1-MMP1).

According to some embodiments of the invention, the infection is a respiratory infection.

According to some embodiments of the invention, the pathogen is a virus.

According to some embodiments of the invention, the virus is a respiratory virus.

According to some embodiments of the invention, the respiratory virus is influenza.

According to some embodiments of the invention, the anti-pathogenic agent is a neuraminidase inhibitor (NAI).

According to some embodiments of the invention, the neuraminidase inhibitor is selected from the group consisting of Laninamivir, Oseltamivir, Peramivir and Zanamivir.

According to some embodiments of the invention, the neuraminidase inhibitor is Oseltamivir.

According to some embodiments of the invention, the secondary infection is a bacterial infection.

According to some embodiments of the invention, the bacterial infection is *S. pneumoniae.*

According to some embodiments of the invention, the agent which down-regulates the at least one polypeptide is an antibody.

According to some embodiments of the invention, the agent which down-regulates the at least one polypeptide is a polynucleotide agent.

According to some embodiments of the invention, the extracellular matrix-associated polypeptide is set forth in Table 1.

According to some embodiments of the invention, the at least one polypeptide is a matrix metalloproteinase (MMP).

According to some embodiments of the invention, the matrix metalloproteinase is selected from the group consisting of membrane type 1-matrix metalloproteinase 1 (MT1-MMP1), MMP-9, MMP-8 and MMP-3.

According to some embodiments of the invention, the at least one polypeptide is membrane type 1-matrix metalloproteinase 1 (MT1-MMP1).

According to some embodiments of the invention, the anti-pathogenic agent is an antiviral agent.

According to some embodiments of the invention, the anti-viral agent is a neuraminidase inhibitor (NAI).

According to some embodiments of the invention, the neuraminidase inhibitor is selected from the group consisting of Laninamivir, Oseltamivir, Peramivir and Zanamivir.

According to some embodiments of the invention, the neuraminidase inhibitor is Oseltamivir.

According to some embodiments of the invention, the extracellular matrix-associated polypeptide is set forth in Table 1.

According to some embodiments of the invention, the extracellular matrix associated polypeptide is MT1-MMP1.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-1D. Global analysis of extra cellular matrix gene circuits during influenza viral infection (A) K-means clustering (k=20) of 3530 differentially expressed genes (Experimental Procedures) in lungs following influenza infections at 10 time points (n=4 for each time point).

Dynamic range is scaled between −2 to 2 fold changes and color coded. 13.5% (479) of the elevated genes are annotated as involved in ECM remodeling. Functional annotation was done using (cbl-gorilladotcsdottechniondotacdotil) clusters are annotated accordingly and colored. (B) Shown are a subset of gene ontologies (GO) enriched (p<10-4) in infected lungs. (C) Submatrix of gene expression dynamics following influenza infection of ECM remodeling genes. (D) Bar graph showing fold changes relative to T0 using qPCR measurement of MT1-MMP expression following influenza infection. Each sample was run in triplicates from 4 mice (2 biological repeats). Error bars represent standard deviation (SD) of the average number. The target genes were normalized to the endogenous reference gene GAPDH and relative to a non-infected control sample using ΔΔ CT normalization method.

Figure 2A:
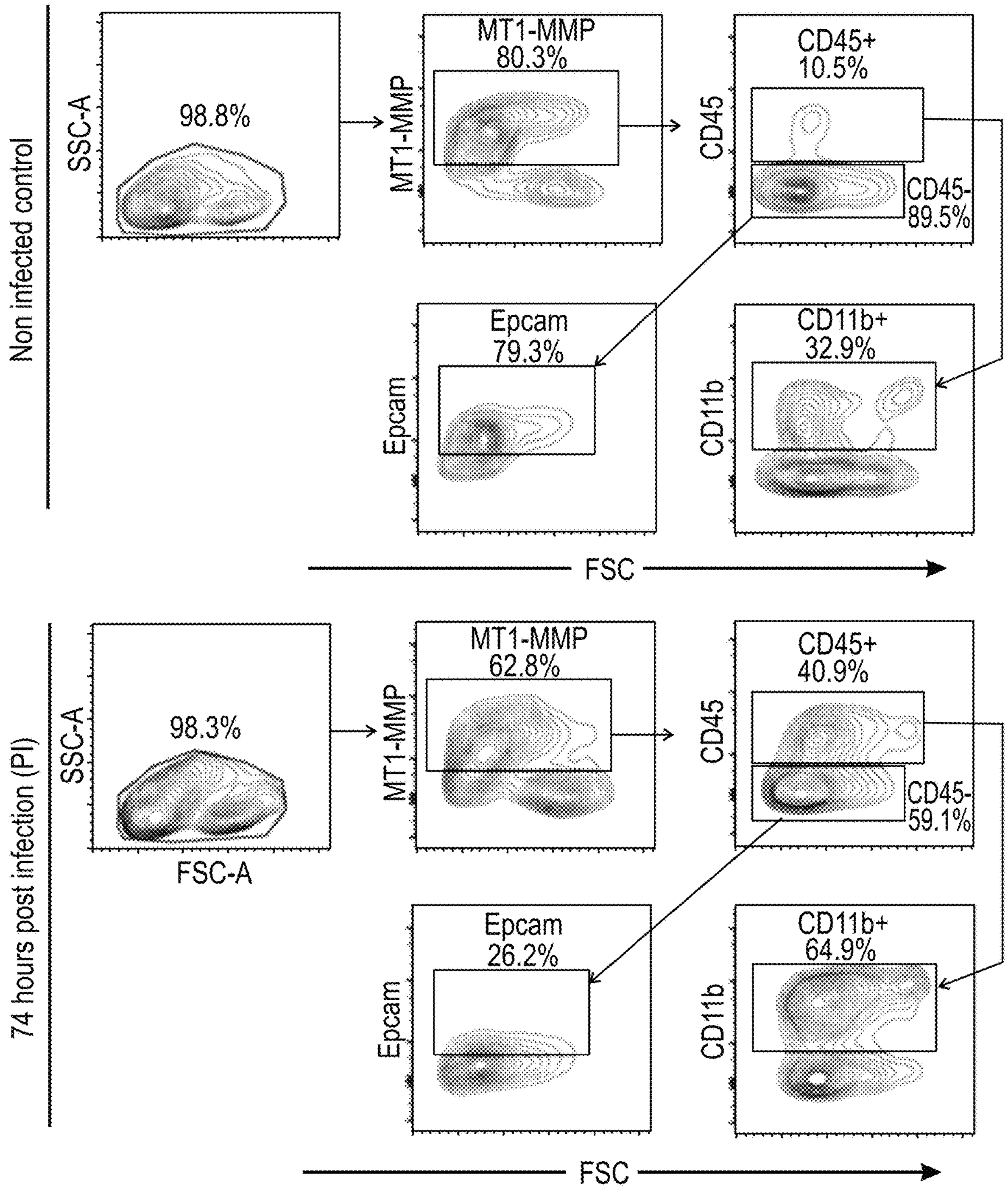
Figure 2B:
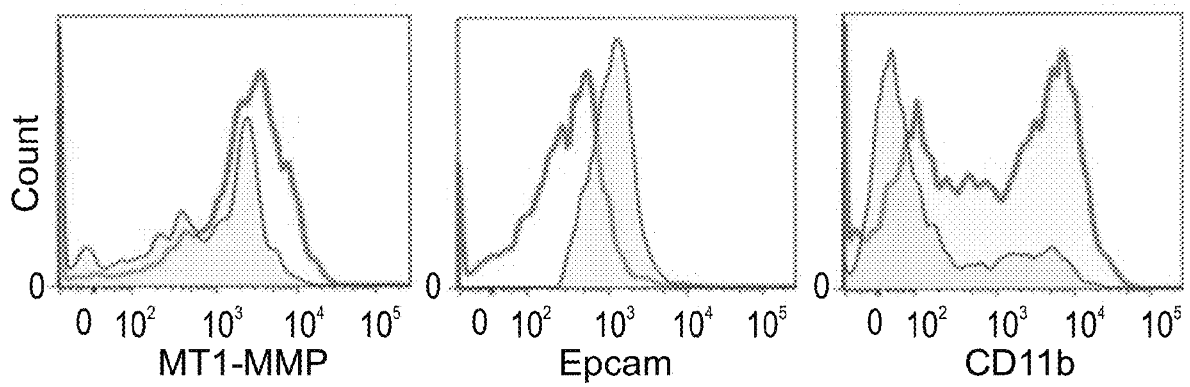
Figure 2C:
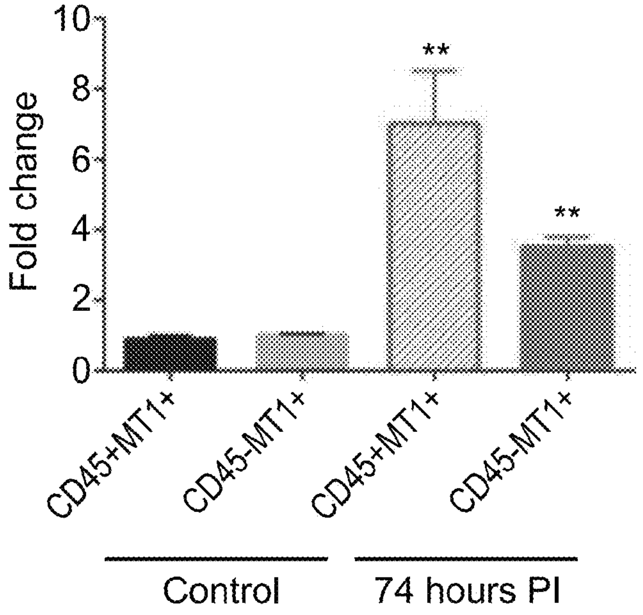

FIGS. 2A-2C. MT1-MMP expression is mostly induced in myeloid cells following influenza infection. (A) FACS analysis from lung of influenza infected mice 74 hours post viral infection (Experimental procedures; n=25) compared to non-infected controls (n=25). Gated are MT1-MMP expressing cells stained using anti-MT1-MMP antibody as well as CD45, CD11b and Epcam (Experimental procedures). (B) Histogram plots showing MT1-MMP, Epcam and CD11b mean fluorescence intensity before (grey) and 74 hours post influenza viral infection (red). (C) Bar graph showing qPCR measurement of MT1-MMP expression in sorted cell populations. Error bars represent SD of the average number. T-test**p<0.001.

FIGS. 3A-3I. Influenza infection induces changes in ECM morphology (A) Global mass spectrometry analysis of cell free ECM scaffolds (see experimental procedures). Quantitative protein abundance is presented by relative measurement (with reference to control uninfected tissue) using gray scale color code ranging from −1 to 1 white to black. Proteins depleted from the ECM post infection are annotated and colored white. Heatmap showing significant changes in protein quantification (p<0.01, t-test) in de-cellularized infected lung tissue as compared to non-infected control. Samples were analyzed in duplicates for 2 time points post infection (74, 122 hours post infection) with lethal dose of influenza infection using Mascot software (B) Representative scanning electron microscope imaging of infected versus control lungs. Arrows and arrow-heads point to orientation changes in collagen fibrils with D-banding patterns as quantified in sub figure (C) Directionality of fibers on the boundaries of alveoli are analyzed using Fiji package (Experimental procedures). (D-H) Representative immuno-staining images of ECM components during infection taken from (n=20) animals and screened in multiple tissue sections and slides imaged under the same exposure conditions. (E-I) Quantification of immunostaining using imageJ package (Experimental procedures), Error bars represent SD of the average number.

FIGS. 4A-4K. Blocking MT1-MMP activity protects lung ECM components. (A) Cartoon showing experimental setup for influenza infection with various treatments. Mice were infected with sub-lethal dose of PR8 influenza strain (Experimental Procedures) (B-E) AirSEM imaging of alveolar and bronchial compartments 74 hours post infection using fixed tissue sections from whole lung, cut 300 μm thick and stained for AirSEM (Experimental Procedures). Alveolar wall thickness and bronchial cell numbers were measured at different areas in multiple sections. Scale of main image-50 μm, inset scale—20 μm. Bar graph quantifies wall thickness and cell numbers in alveoli and bronchi, respectively. Error bars represent SD of the average number; field of view (FOV). (F-G) Representative second harmonic generation (SHG) images originating from an unstained 50 μm thick lung tissue sections. The detected SHG signal representing collagen is shown in red after reproduction of the z-stack using Imaris software package version 7.7.1. Bar graph is showing collagen volumes analyzed and quantified using Imaris package and tested for significance using t-test. Error bars represent SD of the average number (H-I) Lung immuno-staining for laminin. Bar graph shows laminin intensity analyzed using ImageJ package. (J-K) Collagen type I in situ zymography in lung tissue using fluorogenic substrate to detect collagenolytic activity in lung section with high sensitivity. Green signal and arrows point to active collagenase localization among bronchial epithelial lining cells or infiltrating immune cells. Scale—50 μm; Error bars represent SD of the average number; field of view (FOV).

FIGS. 5A-5H. Combining anti-viral treatment with ECM protection supports survival and prevents systemic bacterial sepsis. (A, D) Cartoon showing experimental setup for influenza and S. pneumoniae co-infections in preventative and therapeutic modes. Mice were infected with sub-lethal doses of influenza followed by infection with Strep. pneumoniae (Experimental procedures). Treatment groups included: Tamiflu, anti-MT1-MMP Fab, or the combinations of both. Administration was done using preventive mode, one day before infection (A-C) or as therapeutic mode one-day post infection (D-E). Vehicle-treated mice served as controls (Data are combined from three independent experiments with 7-10 mice in each group). (B, E) Survival curves (Kaplan-Meier) of co-infected mice receiving different treatments a day before (−1) or a day after (+1) the infections. Data is collected from 3 independent experiments of 5 mice in each group. * P<0.01; **p<0.001 using Log-rank (Mantel-Cox) test. (C, F) Relative weight loss of co-infected mice at several time points post viral infection. Error bars represent SD from the mean. (G-H) S. pneumonia bacterial loads from spleen lysates of infected mice 6 days post viral infection (Experimental procedures).

FIGS. 6A-6D. Gene and protein expression levels of ECM modulators during the course of influenza infection. (A) Bar graph showing qPCR measurements of ECM representative genes during different time points post infection in whole lung tissue (fold change relative to expression levels in T0) infection with lethal dose of influenza infection (experimental procedures). Each sample was run in triplicates from 4 mice (2 biological repeats). Error bars represent standard deviation (SD) (B) Western blot analysis of several representative proteases during different time points of influenza infection using a reducing SDS-PAGE gel. (n=10). (C) Quantification of western blot results using ImageJ software. Average relative density of the protein of interest is relative to GAPDH internal control (D) Mean values of body weight (blue; left y axis) and viral titers (red; right y axis) during the course of influenza infection. Error bars represent standard deviations of body weight, calculated on 2-4 animals in each time point from 3 independent experiments. Viral burdens of whole lung homogenates in the lungs of mice using qPCR for genome copies of Matrix protein 2 (M2) followed by conversion into viral particle numbers using a calibration curve.

FIGS. 7A-7D. Immune cells express active MT1-MMP during infection. (A) Immunostaining and bar graph quantification of MT1-MMP and F4/80 marker co-localization in infected lungs (74 hours PI) versus healthy controls. Arrows point to MT1-MMP stained cells. Representative images from multiple sections. (B) Bar graph quantifying panel A. Error bar represent SD, *P≤0.01, t-test. (C) Collagen type I in situ zymography combined with CD45 staining. Arrows point to cells expressing either marker at both control and infected sections (74 hours PI). Scale bar-50 μm (D) Bar graph quantifying panel C. Error bar represent SD, *P≤0.01, t-test.

Figure 8:
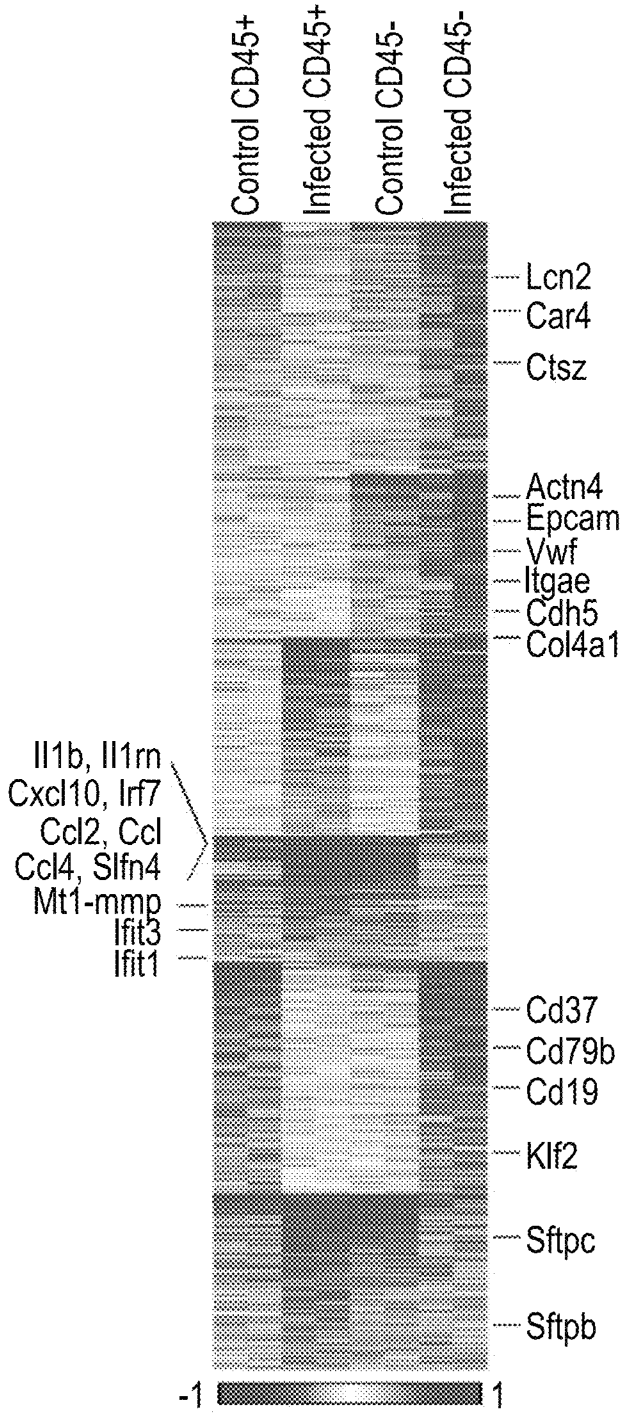

FIG. 8. Global expression analysis of MT1-MMP expressing cells. (A) K-means clustering (k=6) of 2169 differentially expressed genes in $CD45^{pos}$ and $CD45^{neg}$ populations of cells sorted 74 hours post infection (n≥5 mice included in each group-infected and non-infected control). Mice were infected with lethal dose of $4\times10^3$ PFU of PR8 influenza (experimental procedures).

FIGS. 9A-9D. Lung destructive phenotypes demonstrated using AirSEM imaging of whole lung or de-cellularized tissue. (A) Imaging of whole lung tissue. Arrows point to boundaries of alveolar openings with cells (non-infected control) or depleted of cells (infected) (B) Imaging of ECM scaffolds (after de-cellularization) of infected lungs compared to healthy controls. Arrows point to alveolar duct boundaries containing thick organized collagen bundles (non-infected control) or distorted fibrils (infected). (C) Lung cell counts in control and infected lungs scanning multiple lung sections, n=5. (D) Directionality imaging analysis was done by Fiji package. Graphs were plotted using GraphPad Prism 6. The relative frequency of fiber spatial orientation was measured using the "Directionality" plugin analysis tool in Fiji package version 6.1.1.

Figures 10A, 10B, 10C:
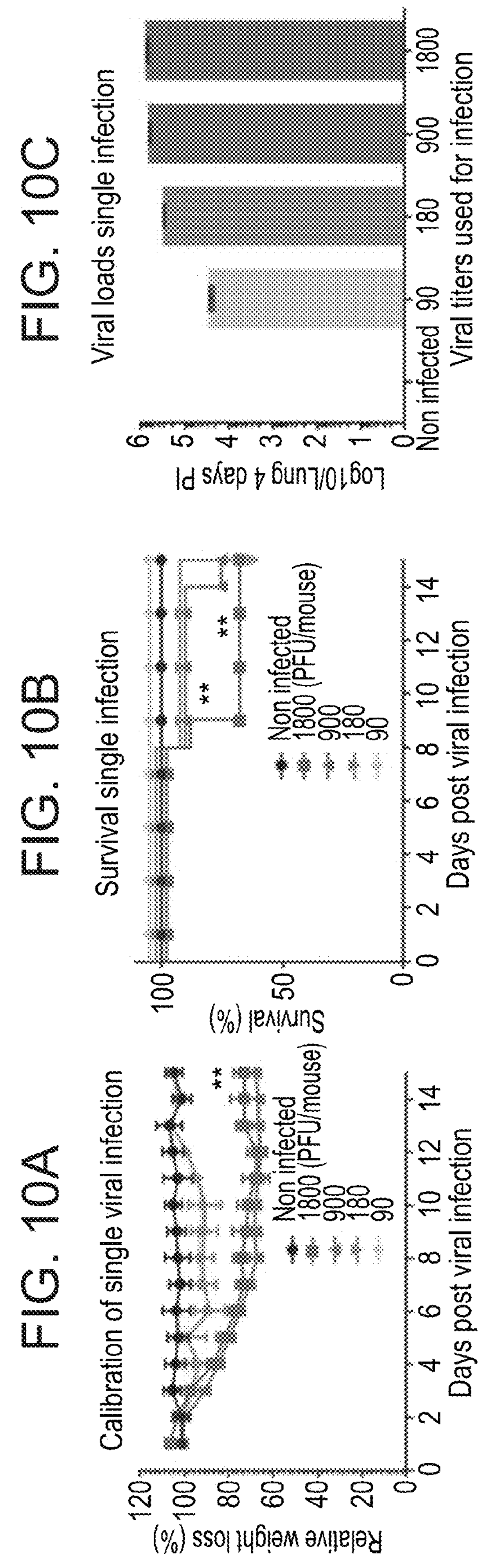

FIGS. 10A-10C. Calibration of single viral infection. (A) Weight loss of mice subjected to single viral infection at different dosages. Data set was analyzed from 5 mice at each time point. Error bar represent SD and analyzed using t-test. (B) Survival of mice exposed to single viral infection at different dosages. Error bar represent SD and analyzed using t-test**P≤0.001. (C) Viral burdens of whole lung homogenates in the lungs 4 days post infection using standard PFU assay. Samples were run with 2 biological repeats 3 animals at each time point. X-axis represents the viral amounts used for the infection.

FIGS. 11A-11F. MT1-MMP inhibition does not interfere with immune cell recruitment or cytokine induction. (A) FACS analysis of whole lung tissue subjected to influenza infection 74 hours post infection and treated either with anti-MT1-MMP inhibitor antibody or non-relevant GST control Ab. Mice were infected at sub-lethal influenza dose (experimental procedures). Data is gated on MT1-MMP expressing cells stained with MT1-MMP antibody as well as CD45, Ly6G, Ly6C, CD11b, NK46, TCRβ (Experimental procedures). Experiments were done twice using 3 mice per group. (B) Representative sections of lung tissue stained for macrophages using F4/80 marker taken at 74 hours post infection. Scale bars=50 μm. FOV indicates the entire field of view at magnification of ×20. (C) Quantification of figure B using multiple tissue sections from at least 3 mice per group. Error bar represent SD, ***P≤0.0001, t-test. (D) Infiltrating immune cells in BALF from mice subjected to single viral infection and taken at 24, 48, 72, 122 hours PI. Mice were infected with sub-lethal dose of influenza. Samples were run with 2 biological repeats. Tested significant over non-infected mice using t-test*P≤0.01. (E-F) TNF-α and IL-1β levels in BALF of mice subjected to single viral infection and taken at 24, 48, 72, 96, 122 hours PI. Samples were run with 2 biological repeats. Error bar represent SD and analyzed using t-test*P≤0.01.

FIGS. 12A-12F. Viral loads in the lung following Anti-MT1-MMP Ab treatment 74 Hours PI (A) Representative lung tissue sections stained for influenza virus using Tamiflu, control Ab and anti-MT1-MMP Ab. Mice were infected sub-lethal dose of influenza (experimental procedures). (B-C) Bar graph quantification of influenza virus 24 and 48 hours PI. Error bar represent SD, **P≤0.001, t-test. FOV indicates the entire field of view at magnification of ×20. Number of infected cells was normalized to DAPI using ImageJ. (D) PFU values of whole lung tissue 4 days and 7 days post viral infection (experimental procedures). Samples were run in triplicates of 2 biological repeats. Error bar represent SD. LEM −1; Tami-1; Tami+LEM-1 designate the different treatments, single or combined agents, given one day before the infection (Day-1). LEM+1; Tami+1; Tami+LEM+1 designate the different treatments, single or combined agents, given one day after the infection (Day+1). LEM refers to anti-MT1-MMP Ab (LEM2/15), GST refers to non-relevant Ab. (E) Viral burdens in the lungs 24, 48 and 96 hours post infection. Whole lung homogenates were used for PFU assay, testing 2 animals at each time point and running 2 biological replicates. Error bar represent SD, *P≤0.01 using 2-way ANOVA. (F) CFU values in the lungs of co-infected mice 2 days post bacterial infection. Error bars represent SD from the mean. Data are combined from two independent experiments with five mice in each group.

FIGS. 13A-13D. ECM destruction is not perturbed by low viral titers. (A) AirSEM images of lungs 74 hours post infection from either Tamiflu-treated, vehicle-treated or control mice. (B) Alveolar wall thickness measured using ImageJ (Experimental procedures), each mark represents a mean of measurements from a section-based region for an individual animal. (C) Bar graph represents viral counts in vehicle-treated and Tamiflu-treated mice lungs using qPCR. Each column represents the mean of 3 mice. Bars indicate mean and SD from the average. X-axis represents hours post viral infection. (D) MT1-MMP expression levels in mice lungs infected with 90 PFU of PR8 influenza strain undergoing different treatments. Error bar represent SD and analyzed using t-test**P≤0.001.

Figure 14A:
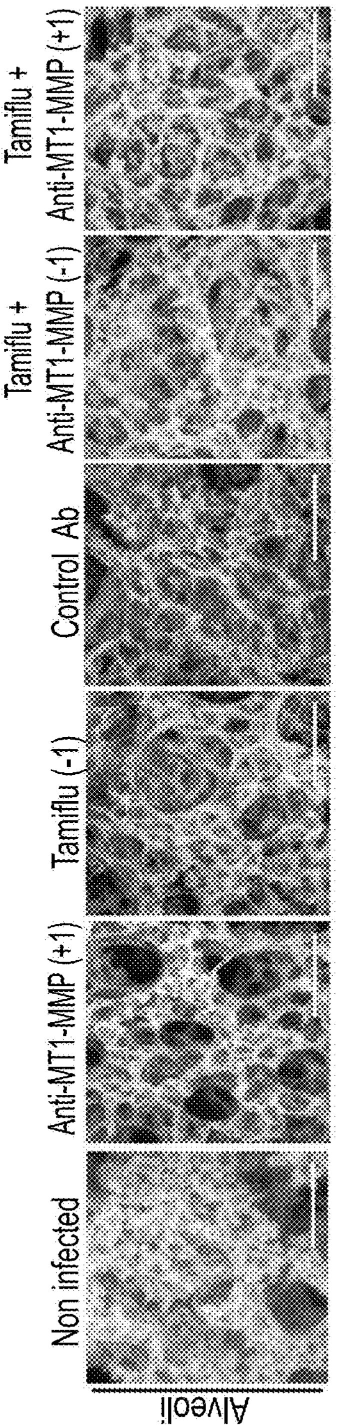
Figure 14B:
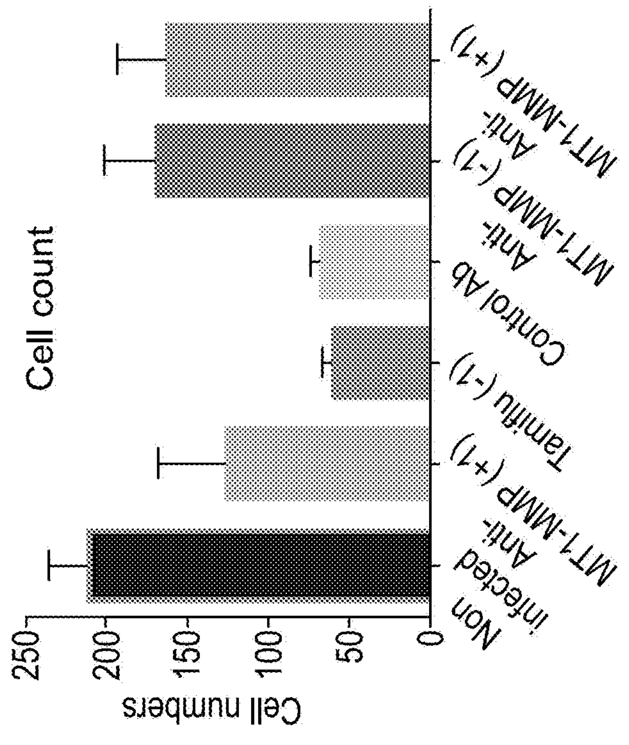

FIGS. 14A-14B. Combined anti-viral and tissue protection therapy maintains lung structural features. (A) AirSEM imaging of lung sections representing changes in lung bronchi and alveoli during infection under several treatment modalities. Scale bar −20 μm. (B) Bar graph quantifying cell numbers in the different treatments taken from multiple sections.

Figure 15:
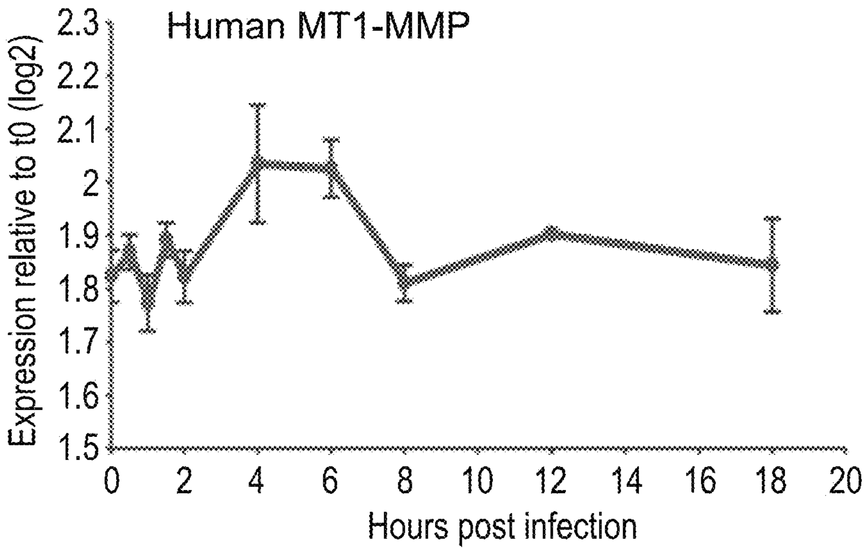

FIG. 15. MT1-MMP expression in human respiratory epithelial cells upon influenza infection. Log2 relative expression levels of MT1-MMP correlating with the infection course (hours post infection) of human bronchial epithelial cells infected with H1N1 strain A/PR/8/34 (PR8). Error bars represent SD. Data analyzed from (Shapira S D, 2009).

DESCRIPTION OF SPECIFIC EMBODIMENTS OF THE INVENTION

The present invention, in some embodiments thereof, relates to a method of preventing secondary infections in subjects infected with a pathogen using agents that downregulate extracellular matrix remodeling.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Infectious disease treatments have conventionally focused on pathogen elimination, either by administering antimicrobial drugs or by stimulating host immune responses using vaccination. The present inventors performed global genomics and proteomics analyses of an influenza mouse model and revealed an unexpected plethora of extracellular matrix (ECM)-related genes and proteins responsible for dysregulated ECM remodeling events during the course of infection (FIGS. 1A-1D and 6A-6D). MT1-MMP was the main collagenase leading to destruction of ECM scaffolds of alveoli and bronchi of infected mouse lungs. Electron microscopy of intact lungs, global mass spectrometry, two-photon and immune staining, and tissue zymography, revealed a multi-faceted destruction of basement membrane components (FIGS. 3A-3I and 9A-9D). This unprecedented damage to lungs contributed to loss of blood-air barrier and resulted in systemic spread of secondary bacterial infection through leakage from lungs to internal organs causing sepsis and mortality. These devastating phenotypes and resulting deadly outcome were reversed by blocking the activity of MT1-MMP (FIGS. 4A-4K), thus offering a new mode of therapeutic intervention through tissue support. As shown in FIGS. 5A-5H, combining anti-viral treatment with ECM protection supports survival and prevents systemic bacterial sepsis.

The present inventors suggest this novel treatment opportunity for infection, designed to support tissue morphology and homeostasis while mitigating inappropriate host responses and collateral tissue damage.

Thus, according to a first aspect of the present invention there is provided a method of treating a subject infected with a pathogen comprising administering to the subject a therapeutically effective amount of an anti-pathogenic agent directed towards the pathogen and a therapeutically effective amount of an agent which down-regulates at least one extracellular matrix-associated polypeptide, herein below, thereby treating the subject.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

As used herein, the term "subject" refers to a mammalian subject—for example a human subject.

The subjects who are treated have pathogens which cause an infection.

As used herein, the term "pathogen" refers to a microbe or microorganism such as a virus, bacterium, prion or fungus that causes a disease (e.g. a respiratory disease).

According to a particular embodiment, the pathogen is a human pathogen.

Exemplary pathogenic viruses may belong to the following families: Adenoviridae, Picornaviridae, Herpesviridae, Hepadnaviridae, Flaviviridae, Retroviridae, Orthomyxoviridae, Paramyxoviridae, Papovaviridae, Polyomavirus, Rhabdoviridae, Togaviridae. Particular pathogenic viruses contemplated by the present invention are those that cause smallpox, influenza, mumps, measles, chickenpox, ebola, or rubella.

According to a particular embodiment, the virus is one which brings about a respiratory infection (e.g. an upper respiratory tract infection and/or a lower respiratory tract infection).

Thus, according to a particular embodiment, the pathogenic virus is an influenza virus (e.g. influenza virus A—(e.g. H1N1, H2N2, H3N2, H5N1, H7N7, H1N2, H9N2, H7N2, H7N3, H10N7 and H7N9), influenza virus B or influenza virus C).

In another embodiment, the pathogenic virus is a parainfluenza virus (hPIV) including the human parainfluenza virus type 1 (hPIV-1) (causes croup); the human parainfluenza virus type 2 (hPIV-2) (causes croup and other upper and lower respiratory tract illnesses), the human parainfluenza virus type 3 (hPIV-3) (associated with bronchiolitis and pneumonia) and the human parainfluenza virus type 4 (hPIV-4).

In yet another embodiment, the pathogenic virus is a respiratory syncytial virus (RSV).

Exemplary pathogenic bacteria include *Mycobacterium tuberculosis* which causes tuberculosis, *Streptococcus* and *Pseudomonas* which cause pneumonia, and *Shigella, Campylobacter* and *Salmonella* which cause foodborne illnesses. Other exemplary pathogenic bacteria contemplated by the present invention are those that cause infections such as tetanus, typhoid fever, diphtheria, syphilis and Hansen's disease.

According to one embodiment, the pathogen causes an acute infection in the subject.

According to another embodiment, the pathogen causes a chronic infection in the subject.

The term "anti-pathogenic agent" refers to an antimicrobial agent and includes, but is not limited to antiviral agents, antibacterial agents, antiviral agents, anti-prion agents.

I. Antiviral Agents

Antiviral agents which can be used for combination therapy according to aspects of the present invention include CRX4 and CCR5 receptor inhibitors such as amantadine and rimantadine and pleconaril. Further antiviral agents that can be used in the combination therapy of this aspect of the present invention include agents which interfere with viral processes that synthesize virus components after a virus invades a cell. Representative agents include nucleotide and nucleoside analogues that look like the building blocks of RNA or DNA, but deactivate the enzymes that synthesize the RNA or DNA once the analogue is incorporated. Acyclovir is a nucleoside analogue, and is effective against herpes virus infections. Zidovudine (AZT), 3TC, FTC, and other nucleoside reverse transcriptase inhibitors (NRTI), as well as non-nucleoside reverse transcriptase inhibitors (NNRTI), can also be used. Integrase inhibitors can also be used. Other antiviral agents include antisense oligonucleotides and ribozymes (directed against viral RNA or DNA at selected sites).

Some viruses, such as HIV, include protease enzymes, which cleave viral protein chains apart so they can be assembled into their final configuration. Protease inhibitors are another type of antiviral agent that can be used in the combination therapy described herein.

The final stage in the life cycle of a virus is the release of completed viruses from the host cell. Some active agents, such as zanamivir (Relenza) and oseltamivir (Tamiflu) treat influenza by preventing the release of viral particles by blocking a molecule named neuraminidase that is found on the surface of flu viruses.

Still other antiviral agents function by stimulating the patient's immune system. Interferons, including pegylated interferons, are representative compounds of this class. Interferon alpha is used, for example, to treat hepatitis B and C. Various antibodies, including monoclonal antibodies, can also be used to target viruses.

Anti-Bacterial Agents:

The antibacterial agent which can be used for combination therapy according to aspects of the present invention may be bactericidal or bacteriostatic.

In one embodiment, the antibacterial agent is an antibiotic.

As used herein, the term "antibiotic agent" refers to a group of chemical substances, isolated from natural sources or derived from antibiotic agents isolated from natural sources, having a capacity to inhibit growth of, or to destroy bacteria. Examples of antibiotic agents include, but are not limited to; Amikacin; Amoxicillin; Ampicillin; Azithromycin; Azlocillin; Aztreonam; Aztreonam; Carbenicillin; Cefaclor; Cefepime; Cefetamet; Cefinetazole; Cefixime; Cefonicid; Cefoperazone; Cefotaxime; Cefotetan; Cefoxitin; Cefpodoxime; Cefprozil; Cefsulodin; Ceftazidime; Ceftizoxime; Ceftriaxone; Cefuroxime; Cephalexin; Cephalothin; Cethromycin; Chloramphenicol; Cinoxacin; Ciprofloxacin; Clarithromycin; Clindamycin; Cloxacillin; Co-amoxiclavuanate; Dalbavancin; Daptomycin; Dicloxacillin; Doxycycline; Enoxacin; Erythromycin estolate; Erythromycin ethyl succinate; Erythromycin glucoheptonate; Erythromycin lactobionate; Erythromycin stearate; Erythromycin; Fidaxomicin; Fleroxacin; Gentamicin; Imipenem; Kanamycin; Lomefloxacin; Loracarbef; Methicillin; Metronidazole; Mezlocillin; Minocycline; Mupirocin; Nafcillin; Nalidixic acid; Netilmicin; Nitrofurantoin; Norfloxacin; Ofloxacin; Oxacillin; Penicillin G; Piperacillin; Retapamulin; Rifaxamin, Rifampin; Roxithromycin; Streptomycin; Sulfamethoxazole; Teicoplanin; Tetracycline; Ticarcillin; Tigecycline; Tobramycin; Trimethoprim; Vancomycin; combinations of Piperacillin and Tazobactam; and their various salts, acids, bases, and other derivatives. Anti-bacterial antibiotic agents include, but are not limited to, aminoglycosides, carbacephems, carbapenems, cephalosporins, cephamycins, fluoroquinolones, glycopeptides, lincosamides, macrolides, monobactams, penicillins, quinolones, sulfonamides, and tetracyclines.

Antibacterial agents also include antibacterial peptides. Examples include but are not limited to abaecin; andropin; apidaecins; bombinin; brevinins; buforin II; CAP18; cecropins; ceratotoxin; defensins; dermaseptin; dermcidin; drosomycin; esculentins; indolicidin; LL37; magainin; maximum H5; melittin; moricin; prophenin; protegrin; and or tachyplesins.

Anti-Fungal Agents:

The term "anti-fungal agent" refers to an agent or chemical that interferes with fungal infection through blocking spore germination, adhesion to substrates, or interfering with any metabolic process or step that is required for growth and development of the fungus or its spores.

Anti-Protozoal Agent:

The term "anti-protozoal" as used herein refers to any chemical or agent that interferes with the parasitic or other life cycle features of a broad range of eukaryotic microbes and invertebrate worms. The agent or chemical might block protein synthesis, essential lipid production, respiratory processes or other metabolic events or growth control steps.

As mentioned herein above, the present invention contemplates administering both an agent directed against the pathogen (as detailed herein above) and an agent which down-regulates at least one extracellular matrix-associated polypeptide.

The term one extracellular matrix-associated polypeptide refers to a polypeptide that reduces the formation or enhances the degradation of the extracellular matrix or is comprised in the extracellular matrix.

According to a particular embodiment, the extracellular matrix-associated polypeptide is a fibrous protein such as collagen, elastin, fibronectin, and laminin.

According to another embodiment, the extracellular matrix-associated polypeptide is a protease such as a matrix metalloproteinase, an enzyme belonging to the class A Disintegrin And Metalloproteinase with Thrombospondin Motifs (ADAMTS) including ADAMTS 1-17 and those belonging to the lysyl oxidase family such as Lysyl oxidase homolog 2 (LOXL).

In one embodiment, the extracellular matrix-associated polypeptide is set forth in Table 2B of the Examples section herein below.

Preferably, the extracellular matrix-associated polypeptide is set forth in Table 1, herein below. Exemplary cDNA sequences of each of the genes are provided therein.

TABLE 1

| Symbol | Gene (Human) | SEQ ID | Gene (mouse) |
|---|---|---|---|
| TIMP1 | NM_003254.2 | 1 | NM_001044384 |
| ADAMTS4 | NM_005099.4 | 2 | NM_172845 |
| TNC | NM_002160.3 | 3 | NM_011607 |
| VCAN | NM_001126336.2 | 4 | NM_001134475 |
| THBS1 | NM_003246.3 | 5 | NM_011580 |
| PLAU | NM_001145031.1 | 6 | NM_008873 |
| HAS1 | NM_001297436.1 | 7 | NM_008215 |
| SERPINA3 | NM_001085.4 | 8 | NM_001033335 (3F), NM_009253 (3M), NM_009251 (3G) NM_009252 (3N) |
| SERPINE1 | NM_000602 | 9 | NM_008871 |
| MMP3 | NM_002422.3 | 10 | NM_010809 |
| ADAMTS15 | NM_139055.2 | 11 | NM_001024139 |
| PRSS22 | NM_022119.3 | 12 | NM_133731 |
| ITGA5 | NM_002205.2 | 13 | NM_010577 |
| LGMN | NM_005606.6 | 14 | NM_011175 |
| MMP14 | NM_004995.3 | 15 | NM_008608 |
| GZMB | NM_00413L4 | 16 | NM_013542 |
| MMP9 | NM_004994.2 | 17 | NM_013599 |
| LCN2 | NM_005564.3 | 18 | NM_008491 |
| MMP8 | NM_001304441.1 | 19 | NM_008611 |
| LOXL3 | NM_001289164.1 | 20 | NM_013586 |
| AIF1 | NM_001623.3 | 21 | NM_019467 |
| LOXL2 | NM_002318.2 | 22 | NM_033325 |
| TIMP3 | NM_000362.4 | 23 | NM_011595 |
| LOXL1 | NM_005576.3 | 24 | NM_010729 |
| ADAM8 | NM_001109.4 | 25 | NM_007403 |
| SERPING1 | NM_000062.2 | 26 | NM_009776 |
| SERINC3 | NM_006811.2 | 27 | NM_012032 |

Downregulation of ECM-associated polypeptides can be effected on the genomic and/or the transcript level using a variety of molecules which interfere with transcription and/or translation [e.g., RNA silencing agents (e.g., antisense, siRNA, shRNA, microRNA), Ribozyme and DNAzyme], or on the protein level using e.g., antagonists, enzymes that cleave the polypeptide and the like.

Following is a list of agents capable of downregulating expression level and/or activity of ECM-associated polypeptides.

One example, of an agent capable of ECM-associated polypeptides is an antibody or antibody fragment capable of specifically binding thereto and down-regulating activity thereof.

Preferably, the antibody binds with a Ki of less than 1000 nm, more preferably less than 100 nm and even more preferably less than 10 nm to its target polypeptide.

Preferably, the antibody specifically binds at least one epitope of the polypeptide. As used herein, the term "epitope" refers to any antigenic determinant on an antigen to which the paratope of an antibody binds.

Epitopic determinants usually consist of chemically active surface groupings of molecules such as amino acids or carbohydrate side chains and usually have specific three dimensional structural characteristics, as well as specific charge characteristics.

According to one embodiment, the epitopic determinant is on the surface of the polypeptide.

According to another embodiment, when the polypeptide is a matrix metalloproteinase (MMP) such as MT1-MMP1, MMP-9, MMP-8 and MMP-3 the antibody binds to (and may optionally be generated by immunizing with) a hapten compound, [2-(2-minoethylcarbomoyl)-ethoxymethyl]-tris-[2-(N-(3-imidazol-1-yl-propyl))-ethoxymethyl]methane. This hapten molecule closely mimics the local structure and conformation of the reactive zinc site in MMPs (see WO 2008/102359, the contents of which are incorporated herein by reference).

In one embodiment, the antibody is capable of specifically binding to the active form of the antibody and not to the proenzyme form.

Preferably, the antibody is specific to the particular matrix metalloproteinase (MMP) and binds with at least 5 times higher affinity to that particular MMP than a non relevant MMP.

According to a specific embodiment, the polypeptide is MT1-MMP1, also known as MMP-14.

Examples of antibodies that bind and down-regulate MMP-14 include those produced by the LEM-2/15 hybridoma cells as detailed in Udi et al., Structure 23, 1-12, Jan. 6, 2015, the contents of which are incorporated herein by reference.

According to another embodiment, the antibody targets a surface epitope of MMP -14. Thus, for example the antibody may bind to the VB loop of MMP-14 (for example residues 160-173 and/or residues 218-233 of MMP-14). In another embodiment, the antibody is one which causes a conformational swiveling motion of the V-B loop of MMP -14.

An exemplary amino acid sequence of the $V_H$ of a MMP-14 downregulating antibody is presented in SEQ ID NO: 54. An exemplary amino acid sequence of the $V_L$ of a MMP-14 downregulating antibody is presented in SEQ ID NO: 55.

In yet another embodiment, the antibody is such that it down-regulates the collagenase activity of MMP-14, but does not affect the activation of pro-MMP-2.

Additional antibodies which down-regulate MMP-14 are disclosed in U.S. Pat. No. 8,501,181 and Devy et al., Biochemistry Research International, Volume 2011, Article ID 191670, 11 pages, doi:10.1155/2011/191670.

The term "antibody" as used in this invention includes intact molecules as well as functional fragments thereof, such as Fab, F(ab')2, and Fv that are capable of binding to macrophages. These functional antibody fragments are defined as follows: (1) Fab, the fragment which contains a monovalent antigen-binding fragment of an antibody molecule, can be produced by digestion of whole antibody with the enzyme papain to yield an intact light chain and a portion of one heavy chain; (2) Fab', the fragment of an antibody molecule that can be obtained by treating whole antibody with pepsin, followed by reduction, to yield an intact light chain and a portion of the heavy chain; two Fab' fragments are obtained per antibody molecule; (3) (Fab')2, the fragment of the antibody that can be obtained by treating whole antibody with the enzyme pepsin without subsequent reduction; F(ab')2 is a dimer of two Fab' fragments held together by two disulfide bonds; (4) Fv, defined as a genetically engineered fragment containing the variable region of the light chain and the variable region of the heavy chain expressed as two chains; and (5) Single chain antibody ("SCA"), a genetically engineered molecule containing the variable region of the light chain and the variable region of the heavy chain, linked by a suitable polypeptide linker as a genetically fused single chain molecule.

Methods of producing polyclonal and monoclonal antibodies as well as fragments thereof are well known in the art (See for example, Harlow and Lane, Antibodies: A Laboratory Manual, Cold Spring Harbor Laboratory, New York, 1988, incorporated herein by reference).

Antibody fragments according to some embodiments of the invention can be prepared by proteolytic hydrolysis of the antibody or by expression in *E. coli* or mammalian cells (e.g. Chinese hamster ovary cell culture or other protein expression systems) of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')2. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, which patents are hereby incorporated by reference in their entirety. See also Porter, R. R. [Biochem. J. 73: 119-126 (1959)]. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments comprise an association of VH and VL chains. This association may be noncovalent, as described in Inbar et al. [Proc. Nat'l Acad. Sci. USA 69:2659-62 (19720]. Alternatively, the variable chains can be linked by an intermolecular disulfide bond or cross-linked by chemicals such as glutaraldehyde. Preferably, the Fv fragments comprise VH and VL chains connected by a peptide linker. These single-chain antigen binding proteins (sFv) are prepared by constructing a structural gene comprising DNA sequences encoding the VH and VL domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are described, for example, by [Whitlow and Filpula, Methods 2: 97-105 (1991); Bird et al., Science 242:423-426 (1988); Pack et al., Bio/Technology 11:1271-77 (1993); and U.S. Pat. No. 4,946,778, which is hereby incorporated by reference in its entirety.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick and Fry [Methods, 2: 106-10 (1991)].

Humanized forms of non-human (e.g., murine) antibodies are chimeric molecules of immunoglobulins, immunoglobulin chains or fragments thereof (such as Fv, Fab, Fab', F(ab').sub.2 or other antigen-binding subsequences of antibodies) which contain minimal sequence derived from non-human immunoglobulin. Humanized antibodies include human immunoglobulins (recipient antibody) in which residues form a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321:522-525 (1986); Riechmann et al., Nature, 332:323-329 (1988); and Presta, Curr. Op. Struct. Biol., 2:593-596 (1992)].

Methods for humanizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers [Jones et al., Nature, 321:522-525 (1986); Riechmann et al., Nature 332:323-327 (1988); Verhoeyen et al., Science, 239:1534-1536 (1988)], by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991)]. Similarly, human antibodies can be made by introduction of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10: 779-783 (1992); Lonberg et al., Nature 368: 856-859 (1994); Morrison, Nature 368 812-13 (1994); Fishwild et al., Nature Biotechnology 14, 845-51 (1996); Neuberger, Nature Biotechnology 14: 826 (1996); and Lonberg and Huszar, Intern. Rev. Immunol. 13, 65-93 (1995).

Down-regulation of ECM-associated polypeptides can be also achieved by RNA silencing. As used herein, the phrase "RNA silencing" refers to a group of regulatory mechanisms [e.g. RNA interference (RNAi), transcriptional gene silencing (TGS), post-transcriptional gene silencing (PTGS), quelling, co-suppression, and translational repression] mediated by RNA molecules which result in the inhibition or "silencing" of the expression of a corresponding protein-coding gene. RNA silencing has been observed in many types of organisms, including plants, animals, and fungi.

As used herein, the term "RNA silencing agent" refers to an RNA which is capable of specifically inhibiting or "silencing" the expression of a target gene. In certain embodiments, the RNA silencing agent is capable of preventing complete processing (e.g, the full translation and/or expression) of an mRNA molecule through a post-transcriptional silencing mechanism. RNA silencing agents include noncoding RNA molecules, for example RNA duplexes comprising paired strands, as well as precursor RNAs from which such small non-coding RNAs can be generated. Exemplary RNA silencing agents include dsRNAs such as siRNAs, miRNAs and shRNAs. In one embodiment, the RNA silencing agent is capable of inducing RNA interference. In another embodiment, the RNA silencing agent is capable of mediating translational repression.

According to an embodiment of the invention, the RNA silencing agent is specific to the target RNA (e.g., MMP-14) and does not cross inhibit or silence a gene or a splice variant which exhibits 99% or less global homology to the target gene, e.g., less than 98%, 97%, 96%, 95%, 94%, 93%, 92%, 91%, 90%, 89%, 88%, 87%, 86%, 85%, 84%, 83%, 82%, 81% global homology to the target gene.

RNA interference refers to the process of sequence-specific post-transcriptional gene silencing in animals mediated by short interfering RNAs (siRNAs). The corresponding process in plants is commonly referred to as post-transcriptional gene silencing or RNA silencing and is also referred to as quelling in fungi. The process of post-transcriptional gene silencing is thought to be an evolutionarily-conserved cellular defense mechanism used to prevent the expression of foreign genes and is commonly shared by diverse flora and phyla. Such protection from foreign gene expression may have evolved in response to the production of double-stranded RNAs (dsRNAs) derived from viral infection or from the random integration of transposon elements into a host genome via a cellular response that specifically destroys homologous single-stranded RNA or viral genomic RNA.

The presence of long dsRNAs in cells stimulates the activity of a ribonuclease III enzyme referred to as dicer. Dicer is involved in the processing of the dsRNA into short pieces of dsRNA known as short interfering RNAs (siRNAs). Short interfering RNAs derived from dicer activity are typically about 21 to about 23 nucleotides in length and comprise about 19 base pair duplexes. The RNAi response also features an endonuclease complex, commonly referred to as an RNA-induced silencing complex (RISC), which mediates cleavage of single-stranded RNA having sequence complementary to the antisense strand of the siRNA duplex. Cleavage of the target RNA takes place in the middle of the region complementary to the antisense strand of the siRNA duplex.

Accordingly, some embodiments of the invention contemplate use of dsRNA to down-regulate protein expression from mRNA.

According to one embodiment, the dsRNA is greater than 30 bp. The use of long dsRNAs (i.e. dsRNA greater than 30 bp) has been very limited owing to the belief that these longer regions of double stranded RNA will result in the induction of the interferon and PKR response. However, the use of long dsRNAs can provide numerous advantages in that the cell can select the optimal silencing sequence alleviating the need to test numerous siRNAs; long dsRNAs will allow for silencing libraries to have less complexity than would be necessary for siRNAs; and, perhaps most importantly, long dsRNA could prevent viral escape mutations when used as therapeutics.

Various studies demonstrate that long dsRNAs can be used to silence gene expression without inducing the stress response or causing significant off-target effects—see for example [Strat et al., Nucleic Acids Research, 2006, Vol. 34, No. 13 3803-3810; Bhargava A et al. Brain Res. Protoc. 2004; 13:115-125; Diallo M., et al., Oligonucleotides. 2003; 13:381-392; Paddison P. J., et al., Proc. Natl Acad. Sci. USA. 2002; 99:1443-1448; Tran N., et al., FEBS Lett. 2004; 573:127-134].

In particular, the invention according to some embodiments thereof contemplates introduction of long dsRNA (over 30 base transcripts) for gene silencing in cells where the interferon pathway is not activated (e.g. embryonic cells and oocytes) see for example Billy et al., PNAS 2001, Vol 98, pages 14428-14433. and Diallo et al, Oligonucleotides, Oct. 1, 2003, 13(5): 381-392. doi:10.1089/154545703322617069.

The invention according to some embodiments thereof also contemplates introduction of long dsRNA specifically designed not to induce the interferon and PKR pathways for down-regulating gene expression. For example, Shinagwa and Ishii [*Genes & Dev.* 17 (11): 1340-1345, 2003] have developed a vector, named pDECAP, to express long double-strand RNA from an RNA polymerase II (Pol II) promoter. Because the transcripts from pDECAP lack both the 5'-cap structure and the 3'-poly(A) tail that facilitate ds-RNA export to the cytoplasm, long ds-RNA from pDECAP does not induce the interferon response.

Another method of evading the interferon and PKR pathways in mammalian systems is by introduction of small inhibitory RNAs (siRNAs) either via transfection or endogenous expression.

The term "siRNA" refers to small inhibitory RNA duplexes (generally between 18-30 basepairs) that induce the RNA interference (RNAi) pathway. Typically, siRNAs are chemically synthesized as 21mers with a central 19 bp duplex region and symmetric 2-base 3'-overhangs on the termini, although it has been recently described that chemically synthesized RNA duplexes of 25-30 base length can have as much as a 100-fold increase in potency compared with 21mers at the same location. The observed increased potency obtained using longer RNAs in triggering RNAi is theorized to result from providing Dicer with a substrate (27mer) instead of a product (21mer) and that this improves the rate or efficiency of entry of the siRNA duplex into RISC.

It has been found that position of the 3'-overhang influences potency of an siRNA and asymmetric duplexes having a 3'-overhang on the antisense strand are generally more potent than those with the 3'-overhang on the sense strand (Rose et al., 2005). This can be attributed to asymmetrical strand loading into RISC, as the opposite efficacy patterns are observed when targeting the antisense transcript.

The strands of a double-stranded interfering RNA (e.g., an siRNA) may be connected to form a hairpin or stem-loop structure (e.g., an shRNA). Thus, as mentioned the RNA silencing agent of some embodiments of the invention may also be a short hairpin RNA (shRNA).

The term "shRNA", as used herein, refers to an RNA agent having a stem-loop structure, comprising a first and second region of complementary sequence, the degree of complementarity and orientation of the regions being sufficient such that base pairing occurs between the regions, the first and second regions being joined by a loop region, the loop resulting from a lack of base pairing between nucleotides (or nucleotide analogs) within the loop region. The number of nucleotides in the loop is a number between and including 3 to 23, or 5 to 15, or 7 to 13, or 4 to 9, or 9 to 11. Some of the nucleotides in the loop can be involved in base-pair interactions with other nucleotides in the loop. It will be recognized by one of skill in the art that the resulting single chain oligonucleotide forms a stem-loop or hairpin structure comprising a double-stranded region capable of interacting with the RNAi machinery.

It will be appreciated that the RNA silencing agent of some embodiments of the invention need not be limited to those molecules containing only RNA, but further encompasses chemically-modified nucleotides and non-nucleotides.

In some embodiments, the RNA silencing agent provided herein can be functionally associated with a cell-penetrating peptide." As used herein, a "cell-penetrating peptide" is a peptide that comprises a short (about 12-30 residues) amino acid sequence or functional motif that confers the energy-independent (i.e., non-endocytotic) translocation properties associated with transport of the membrane-permeable complex across the plasma and/or nuclear membranes of a cell. The cell-penetrating peptide used in the membrane-permeable complex of some embodiments of the invention preferably comprises at least one non-functional cysteine residue, which is either free or derivatized to form a disulfide link with a double-stranded ribonucleic acid that has been modified for such linkage. Representative amino acid motifs conferring such properties are listed in U.S. Pat. No. 6,348,185, the contents of which are expressly incorporated herein by reference. The cell-penetrating peptides of some embodiments of the invention preferably include, but are not limited to, penetratin, transportan, pIsl, TAT (48-60), pVEC, MTS, and MAP.

mRNAs to be targeted using RNA silencing agents include, but are not limited to, those whose expression is correlated with an undesired phenotypic trait. Exemplary mRNAs that may be targeted are those that encode truncated proteins i.e. comprise deletions. Accordingly the RNA silencing agent of some embodiments of the invention may be targeted to a bridging region on either side of the deletion. Introduction of such RNA silencing agents into a cell would cause a down-regulation of the mutated protein while leaving the non-mutated protein unaffected.

According to another embodiment the RNA silencing agent may be a miRNA or miRNA mimic.

The term "microRNA", "miRNA", and "miR" are synonymous and refer to a collection of non-coding single-stranded RNA molecules of about 19-28 nucleotides in length, which regulate gene expression. miRNAs are found in a wide range of organisms (viruses.fwdarw.humans) and have been shown to play a role in development, homeostasis, and disease etiology.

The term "microRNA mimic" refers to synthetic non-coding RNAs that are capable of entering the RNAi pathway and regulating gene expression. miRNA mimics imitate the function of endogenous microRNAs (miRNAs) and can be designed as mature, double stranded molecules or mimic precursors (e.g., or pre-miRNAs). miRNA mimics can be comprised of modified or unmodified RNA, DNA, RNA-DNA hybrids, or alternative nucleic acid chemistries (e.g., LNAs or 2'-O,4'-C-ethylene-bridged nucleic acids (ENA)). For mature, double stranded miRNA mimics, the length of the duplex region can vary between 13-33, 18-24 or 21-23 nucleotides. The miRNA may also comprise a total of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides. The sequence of the miRNA may be the first 13-33 nucleotides of the pre-miRNA. The sequence of the miRNA may also be the last 13-33 nucleotides of the pre-miRNA.

Another agent capable of downregulating ECM-associated polypeptides is a DNAzyme molecule capable of specifically cleaving an mRNA transcript or DNA sequence of the polypeptide.

Downregulation ECM-associated polypeptides can also be effected by using an antisense polynucleotide capable of specifically hybridizing with an mRNA transcript encoding same.

Another agent capable of downregulating ECM-associated polypeptides is a ribozyme molecule capable of specifically cleaving an mRNA transcript encoding same.

Another agent capable of downregulating ECM-associated polypeptides would be any molecule which binds to and/or cleaves the polypeptide. Such molecules can be antagonists, or inhibitory peptide.

For example, Zarrabi et al (J Biol Chem. 2011 Sep. 23; 286(38): 33167-33177) discloses peptides that inhibit MMP-14.

It will be appreciated that a non-functional analogue of at least a catalytic or binding portion of any of the disclosed polypeptides can be also used as an agent which down-regulates ECM-associated polypeptides.

Another agent which can be used along with some embodiments of the invention to down-regulate the ECM-associated polypeptides is a molecule which prevents activation or substrate binding thereto.

Additional exemplary inhibitors of matrix metalloproteinases include the hydroxamate inhibitors, small peptide analogs of fibrillar collagens, which specifically interact in a bidentate manner via the hydroxyl and carbonyl oxygens of the hydroxamic group with the zinc ion in the catalytic site [Grams et al., (1995), Biochem. 34: 14012-14020; Bode et al., (1994), EMBO J., 13: 1263-1269].

Hydroxamate-based MMP inhibitors are usually composed of either a carbon back-bone (WO 95/29892, WO 97/24117, WO 97/49679 and EP 0780386), a peptidyl back-bone (WO 90/05719, WO 93/20047, WO 95/09841 and WO 96/06074) or a peptidomimetic back-bone [Schwartz et al., Progr. Med. Chem., 29: 271-334(1992); Rasmussen et al., Pharmacol. Ther., 75: 69-75 (1997); Denis et al., Invest. New Drugs, 15: 175-185 (1997)]. Alternatively, they contain a sulfonamido sulfonyl group which is bonded on one side to a phenyl ring and a sulfonamido nitrogen which is bonded to an hydroxamate group via a chain of one to four carbon atoms (EP 0757984 A1).

Other peptide-based MMP inhibitors are thiol amides which exhibit collagenase inhibition activity (U.S. Pat. No. 4,595,700), N-carboxyalkyl derivatives containing a biphenylethylglycine which inhibit MMP-3, MMP-2 and collagenase (Durette, et al., WO-9529689), lactam derivatives which inhibit MMPs, TNF-alpha and aggrecanase (see U.S. Pat. No. 6,495,699) and Tricyclic sulfonamide compounds (see U.S. Pat. No. 6,492,422).

Other MMP inhibitors are the chemically modified non-microbial tetracyclines (CMTs) that were shown to block expression of several MMPs in vitro. (Axisa et al., 2002, Stroke 33: 2858-2864).

Recently, a mechanism-based MMP inhibitor, SB-3CT, was designed according to the X-ray crystallographic information of the MMP active site (Brown et al., 2000). X-ray absorption studies revealed that binding of this molecule to the catalytic zinc reconstructs the conformational environment around the active site metal ion back to that of the pro-enzyme [Kleifeld et al., 2001, J Biol. Chem. 276: 17125-31].

In the context of a combination therapy, combination therapy compounds may be administered by the same route of administration (e.g. intrapulmonary, oral, enteral, etc.) that the described compounds are administered. In the alternative, the agents for use in combination therapy with the herein described agents may be administered by a different route of administration.

The agent which down-regulates ECM-associated polypeptides can be administered immediately prior to (or after) the anti-pathogenic agent, on the same day as, one day before (or after), one week before (or after), one month before (or after), or two months before (or after) the anti-pathogenic agent, and the like.

The agents which down-regulate ECM-associated polypeptides and the anti-pathogenic agent can be administered concomitantly, that is, where the administering for each of these agents can occur at time intervals that partially or fully overlap each other. The agents described herein can be administered during time intervals that do not overlap each other. For example, the first agent can be administered within the time frame of t=0 to 1 hours, while the second agent can be administered within the time frame of t=1 to 2 hours. Also, the first agent can be administered within the time frame of t=0 to 1 hours, while the second agent can be administered somewhere within the time frame of t=2-3 hours, t=3-4 hours, t=4-5 hours, t=5-6 hours, t=6-7 hours, t=7-8 hours, t=8-9 hours, t=9-10 hours, and the like. Moreover, the second agent can be administered somewhere in the time frame of t=minus 2-3 hours, t=minus 3-4 hours, t=minus 4-5 hours, t=5-6 minus hours, t=minus 6-7 hours, t=minus 7-8 hours, t=minus 8-9 hours, t=minus 9-10 hours.

The agents of the present invention are typically provided in combined amounts to treat the infection and/or to reduce symptoms or disease associated with a secondary infection. This amount will evidently depend upon the particular agent selected for use, the nature and number of the other treatment modality, the condition(s) to be treated, prevented and/or palliated, the species, age, sex, weight, health and prognosis of the subject, the mode of administration, effectiveness of targeting, residence time, mode of clearance, type and severity of side effects of the agents and upon many other factors which will be evident to those of skill in the art.

The present inventors have shown that administration of an antibody which binds to and down-regulates MMP-14 prevents complications of a secondary infection. More specifically, the present inventors showed that administration of an MMP-14 antibody together with an antiviral agent reduced the symptoms in animals infected with the influenza virus (as the primary infection) and *S. pneumoniae* (as the secondary infection).

Thus, the present inventors propose that administration of agents which specifically down-regulate ECM-associated polypeptides and an antipathogenic agent may prevent (or reduce the symptoms of) a secondary infection.

Thus, according to another aspect of the present invention there is provided a method of treating or preventing a disease associated with a secondary infection in a subject infected with a pathogen comprising administering to the subject a therapeutically effective amount of an anti-pathogenic agent directed towards the pathogen and a therapeutically effective amount of an agent which down-regulates an ECM-associated polypeptide, thereby treating or preventing the disease associated with the secondary infection in the subject.

As used herein, the phrase "secondary infection" refers to an infection that occurs during or after treatment of another pre-existing infection. It may result from the treatment itself or from changes in the immune system.

The term "preventing" refers to inhibiting or arresting the development of the secondary infection and/or causing the prevention, reduction, remission, or regression of symptoms of the secondary infection.

According to a particular embodiment, the combination therapy proposed by the present invention reduces the complications or treats a disease (e.g. sepsis) associated with the secondary infection.

The secondary infection may be a bacterial infection, a viral infection or a fungal infection.

The primary and the secondary infections are typically infections of the same organ (e.g. lungs and/or respiratory tract).

In one embodiment, the primary infection is viral infection (e.g. influenza) and the secondary infection is a bacterial infection (e.g. *S. pneumoniae*).

In another embodiment, the primary infection is a bacterial infection and the secondary infection is a viral infection.

In yet another embodiment, the primary infection is viral infection and the secondary infection is a fungal infection.

In yet another embodiment, the primary infection is a bacterial infection and the secondary infection is a fungal infection.

According to yet another aspect of the present invention there is provided a method of treating influenza in a subject in need thereof comprising administering to the subject a therapeutically effective amount of an agent which down-regulates at least one ECM-associated polypeptide, thereby treating the influenza.

ECM-associated polypeptides have been described herein above. According to a particular embodiment, the ECM-associated polypeptide is set forth in Table 1—for example MT1-MMP1.

According to a particular embodiment, treatment of influenza is effected by administering an antibody which down-regulates an amount of MT1-MMP1, such as those described herein above.

In order to prevent the collapse of the ECM, preferably, the agent is provided no more than 5 days after the start of symptoms of the influenza virus, no more than 4 days after the start of symptoms of the influenza virus, no more than 3 days after the start of symptoms of the influenza virus, no more than 2 days after the start of symptoms of the influenza virus, and even no more than 1 day after the start of symptoms of the influenza virus.

In any of the method and uses described herein, the agents can be used per se or in a pharmaceutical composition which further comprises a pharmaceutically (or cosmetically) acceptable carrier.

In one embodiment, the agents are co-formulated in the same pharmaceutical composition.

In another embodiment, the agents are formulated in separate pharmaceutical compositions. The separate pharmaceutical compositions may be comprised in a single article of manufacture, e.g. a kit.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to any of the agents described herein. It will be appreciated that the pharmaceutical compositions may comprise additional active agents known to be useful in treating a particular disease.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, intraperitoneal, intranasal, or intraocular injections.

According to a particular embodiment, the route of administration is via topical delivery.

Alternately, one may administer the pharmaceutical composition in a local rather than systemic manner, for example, via injection of the pharmaceutical composition directly into a tissue region of a patient.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum Arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients (e.g. the compounds described herein) effective to prevent, alleviate or ameliorate symptoms of a disorder (e.g., fibrotic or inflammatory disease) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated from animal models to achieve a desired concentration or titer. Such information can be used to more accurately determine useful doses in humans.

Toxicity and therapeutic efficacy of the active ingredients described herein can be determined by standard pharmaceutical procedures in experimental animals. The data obtained from these animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p.1).

Dosage amount and interval may be adjusted individually to provide cell numbers sufficient to induce normoglycemia (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as if further detailed above.

It is expected that during the life of a patent maturing from this application many relevant antiviral/antibacterial agents will be developed and the scope of the term antiviral/antibacterial is intended to include all such new technologies a priori.

As used herein the term "about" refers to ±10%

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W.H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Materials and Methods

Influenza Virus and *Streptococcus pneumoniae* Bacterial Agent:

Mouse-adapted PR8 virus, influenza A/Puerto Rico/8/34 (A/PR/8/34, H1N1) was persistently grown in hen egg amnion and influenza effective titers were quantified as previously described (Achdout et al., 2003). *Streptococcus pneumoniae* (*S. pneumoniae*) D39 type 2 encapsulated strain was grown in Todd-Hewitt broth (Difco Laboratories) For isolation and infection of mice, bacteria were grown overnight on tryptic soy agar (Hylab Laboratories) supplemented with 3% (vol/vol) sheep erythrocyte at 37° C. and were then harvested by centrifugation at 4000 g for 20 min to pellet the bacteria and dilute it to the desired concentration.

Infection Procedures:

Female C57BL/6J mice (4-5 weeks of age) were anesthetized with ketamine-xylazine and were intra-nasally inoculated with 50 μl of diluted virus. The same stock was used for all the experiments containing influenza A/Puerto Rico/8/34 (A/PR/8/34, H1N1) strain, $9\times10^7$ PFU/ml, HA 1:1,024. To study pathogenesis of Influenza infection, C57BL/6 mice were intra-nasally infected with $4\times10^3$ PFU of influenza PR8 virus equivalent to lethal dose. Mice were sacrificed on 3, 7, 11, 26, 32, 49, 74, 98, 122, 148 hours post infection and the lungs were harvested and homogenized for RNA isolation. To study the effectivity of anti-MT1-MMP inhibitor, both in the single viral infection model and in the double infection model combining *S. pneumoniae*, a sub-lethal dose of 800 PFU was used, which was diluted accordingly and administered along the same route. *S. pneumoniae* was grown on tryptic soy agar (Hylab Laboratories) supplemented with 3% (vol/vol) sheep erythrocytes. The bacterium was diluted in sterile PBS and administered intra-nasally 4 days post viral infection at a dose of 30 CFU, in a volume of 50 μl. The mice were anesthetized and held in an upright position while inoculated. Mice were weighted and monitored at least daily for illness and mortality. All animal procedures were performed according to IACUC guidelines and were approved by the committee of the Weizmann Institute of Science.

Treatment of Animals:

Mice were treated in the single infection experiments as well as in the co-infection experiments with 3 mg/kg of LEM 2/15 Fab fragment at a total volume of 100 μl per injection, given intra-peritoneally every day. GST-Fab, designated in text as control Fab, served as non-relevant control and was given the same dose as the LEM 2/15 treated group. PBS used as a vehicle control.

LEM 2/15 (Anti-MTI-MMP Ab) Purification:

Hybridoma cells of LEM-2/15 were grown in DCCM (serum-free medium designed for hybridoma cell growth and monoclonal antibody production, purchased from Biological Industries). Cells were precipitated by centrifugation at 193 g, and the supernatant was collected. The supernatant was dialyzed against 20 mM phosphate buffer (pH 8). A 1 ml HiTrap protein A high-performance column was equilibrated with 100 mM phosphate buffer (pH 8), and the supernatant was loaded at 1 ml/min. The antibody was eluted with 100 mM citrate buffer (pH 6) and dialyzed against 50 mM Tris-HCl (pH 7.5) and 150 mM NaCl.

Antibody Digestion with Papain:

Papain was activated in 0.5 M Tris-HCl (pH 8), 10 mM EDTA, and 5 mM dithiothreitol for 15 min at 370 C. Active papain was added to a solution of intact LEM-2/15 at a ratio of 1:1,000, and the digestion process was carried out for 3 h at 370 C. The digestion reaction was terminated with the addition of 20 mM iodoacetamide in the dark at room temperature for 30 min. The Fab fragment was isolated from the Fc by a protein A column, and the Fab fragment was collected from the flow through and dialyzed against 50 mM Tris-HCl (pH 7.5) and 150 mM NaCl. The purity of the Fab fragment was estimated by 12% SDS-PAGE gel. Pure Fab fragment was filtered to assure sterility and kept at −80° C. conditions until use.

Glutathione S-transferases (GST)-Fab Fragment:

Fab fragment from the whole GST antibody were produced as described in the upper section (Antibody Digestion with Papain).

Quantification of Viral and Bacterial Loads:

Viral titers in the lungs were determined by titration of organ homogenate on MDCK cells and plaque forming units (PFUs) were quantified as described in (Okuda et al., 2001). Strep. *pneumoniae* levels were determined by plating titrated amounts of organ homogenate on tryptic soy agar plates supplemented with 3% sheep erythrocytes (Hylab Laboratories). Organs were homogenized using the GentleMACS 1 ml of appropriate buffer for PFUs or 10 ml of sterile water for Strep. *pneumoniae* for CFUs. Viral burdens were also quantified using qPCR, as described before for the detection of virus in patients (Hindiyeh et al., 2005). *S. pneumoniae* identification was done using qPCR as previously described (Ogunniyi et al., 2002). Serial dilutions of Influenza A (A/PR/8/34) virus titrated on Madin-Darby Canine Kidney (MDCK) cells were used as standards to determine the quantity of the influenza virus by quantitative real-time PCR (qRT-PCR) and convert the qPCR results into viral load numbers.

RNA Isolation:

Lungs were removed and immediately transferred into RNA Latter solution (Invitrogen). For RNA isolation, the lung was cut into small pieces in the presence of QIAzol, homogenized using SPEX CertiPrep homogenizer, and total RNA was extracted with a miRNeasy Mini Kit (Qiagen). RNA integrity was determined (Tapestation, Agilent Technologies) and concentration measured with a Qubit Fluorometric Quantitation device (LifeTechnologies).

Preparation of RNA Sequencing Libraries:

For RNA-seq a derivation of MARS-seq technique was used as described in (Jaitin et al., 2014). In brief, total RNA was fragmented into fragments having an average size of 300 nucleotides by chemical heat (95° C.) treatment for 4:30 min (NEBNext Magnesium RNA Fragmentation Module). The 3' polyadenylated fragments were enriched by selection on poly dT beads (Dynabeads Invitrogen). Strand-specific cDNA was synthesized using a poly T-VN oligo (18 T) and Affinity Script RT enzyme (Agilent). Double-strand DNA was obtained using Second strand synthesis kit (NEB). DNA ends were repaired using T4 polynucleotide kinase and T4 polymerase (NEB-Next). After the addition of an adenine base residue to the 5' end using Klenow enzyme (NEB-Next), a barcode Illumina compatible adaptor (IDT) was ligated to each fragment. The washed DNA fragment was amplified by PCR (12 cycles) using specific primers (IDT) to the ligated adaptors. The quality of each library was analyzed by TapeStation (Agilent).

Pre Processing of RNASeq Data:

RNA-seq was performed as described in Lavin et al., 2014. In brief, all reads, both from whole lung (FIGS. 1A-1D) and cell populations (FIG. 8) were aligned to the mouse reference genome (NCBI 37, MM9) using the TopHat aligner. Normalized expression table was created using ESAT garberlabdotumassmeddotedu/software/esat/ based on the negative binomial distribution and a local regression model. Data manipulation-Discard genes from table that have values>0 only once; Calculate 75 percentile of data result is 33 (set noise to 32); Find max of raw and discard if max<32; log 2 values as x+32; Average replicates; keep rows where max−min>0.8 (notice not 2 fold but 1.75); K-Means in matlab for 20 clusters; manually ordered the clusters for visual purpose picture was done in GeneE.

qPCR:

Total RNA was reverse transcribed to cDNA using high capacity cDNA reverse transcription kit (Applied Biosystems). RT-PCR was performed with LightCycler480 SYBR green I master mix (Roche) in triplicate, using GAPDH and β-actin for normalization. Primer list is provided in Table 2A, herein below.

TABLE 2A

| Gene | Direction | sequence | SEQ ID |
|---|---|---|---|
| MT1-MMP | Forward | 5-AGCACTGGGTGTTTGACG-3 | 28 |
| MT1-MMP | Reverse | 5-GTCTTCCCATTGGGCATC-3 | 29 |
| MMP-9 | Forward | 5-CAGACGTGGGTCGATTCC-3 | 30 |
| MMP-9 | Reverse | 5-TCATCGATCATGTCTCGC-3 | 31 |
| MMP-8 | Forward | 5-GCAGCGCTTCTTCAGCTT-3 | 32 |
| MMP-8 | Reverse | 5-GTGTGTGTCCACTTGGGA-3 | 33 |
| MMP-2 | Forward | 5-ACGATGATGACCGGAAGT-3 | 34 |
| MMP-2 | Reverse | 5-GTGTAGATCGGGGCCATC-3 | 35 |
| TIMP1-var2 | Forward | 5-GCAGTGATTTCCCCGCCA-3 | 36 |
| TIMP1-var2 | Reverse | 5-GGGGGCCATCATGGTATC-3 | 37 |
| MMP-3 | Forward | 5-AAGGAGGCAGCAGAGAAC-3 | 38 |
| MMP-3 | Reverse | 5-GCACTGTCATGCAATGGG-3 | 39 |
| LGMN | Forward | 5-GCCTACCAGATCATCCAC-3 | 40 |
| LGMN | Reverse | 5-ACATCTGTGCCGTTAGGT-3 | 41 |
| GZMB | Forward | 5-ACAACACTCTTGACGCTG-3 | 42 |
| GZMB | Reverse | 5-CGAGAGTGGGGCTTGACT-3 | 43 |
| LCN2 | Forward | 5-ACAACCAGTTCGCCATGG-3 | 44 |
| LCN2 | Reverse | 5-AAGCGGGGTGAAACGTTCC-3 | 45 |
| PR8 MATRIX A INF A-CDC | Forward | 5-GACCRATCCTGTCACTGAC-3 | 46 |
| PR8 MATRIX A INF A-CDC | Reverse | 5-TGCAGTCCTCGCTCACTGG GCACG-3 | 47 |

TABLE 2A-continued

| Gene | Direction | sequence | SEQ ID |
|---|---|---|---|
| 16S rRNA | Forward | 5-GGTGAGTAACGCGTAGGTAA-3 | 48 |
| 16S Rrna | Reverse | 5-ACGATCCGAAAACCTTCTTC-3 | 49 |
| TIMP-2 | Forward | TCTAGGAGTCCCAGTCAGCC | 50 |
| TIMP-2 | Reverse | CAACAAGGACTGCCAAGCAC | 51 |
| GAPDH | Forward | GCCCTTGAGCTAGGACTGGA | 52 |
| GAPDH | Reverse | TACGGCCAAATCCGTTCACA | 53 |

In Gel Proteolysis and Mass Spectrometry Analysis:

Lung samples were de-cellularized using 0.5% EDTA supplemented with 2% triton, shaking for 24 hours. Samples were then dehydrated using a Speedvac and weighted. Samples were then subjected to in-solution digestion using activated MMP-13, 500 nM in TNC buffer in (50 mM Tris-HCl, 150 mM NaCl, 5 mM MgCl2, 5 mM CaCl2, pH 7.4) a volume of 120μl, for 24 hours shaking at 30° C. The volume and concentration of activated MMP-13 were adjusted according to the weight of each sample, and each sample was run in duplicates. Protein extract was loaded on SDS-PAGE for a short run. The proteins in the gel were reduced with 2.8 mM DTT (60° C. for 30 min), modified with 8.8 mM iodoacetamide in 100 mM ammonium bicarbonate (in the dark, room temperature for 30 min) and digested in 10% acetonitrile and 10 mM ammonium bicarbonate with modified tryp sin (Promega) at a 1:10 enzyme-to-substrate ratio, overnight at 37° C. An additional second trypsinization was done for 4 hours. The resulting tryptic peptides were resolved by reverse-phase chromatography on 0.075×200-mm fused silica capillaries (J&W) packed with Reprosil reversed phase material (Dr Maisch GmbH, Germany). The peptides were eluted with linear 95 minutes gradients of 7 to 40% and 8 minutes at 95% acetonitrile with 0.1% formic acid in water at flow rates of 0.25 μl/min. Mass spectrometry was performed by an ion-trap mass spectrometer (Orbitrap XP, Thermo) in a positive mode using repetitively full MS scan followed by collision induces dissociation (CID) of the 7 most dominant ion selected from the first MS scan.

The mass spectrometry data was analyzed using the MaxQuant 1.3.0.5 software searching against the mouse section of the Uniprot database with mass tolerance of 20 ppm for the precursor masses. Peptide- and protein-level false discovery rates (FDRs) were filtered to 1% using the target-decoy strategy. Protein table were filtered to eliminate the identifications from the reverse database, and common contaminants and single peptide identifications. The data was quantified by label free analysis using the same software, based on extracted ion currents (XICs) of peptides enabling quantitation from each LC/MS run for each peptide identified in any of experiments. To search for ECM related proteins, annotations were determined using the GORILLA Bioinformatics Resources.

Western Blot:

Lung samples were homogenized using gentleMACS (Miltenyi Biotec) according to manufacturer instructions using 500μl rippa buffer containing protease inhibitor cocktail (Roche). Protein levels were then measured using BCA kit (Pierce Biotechnology) and run in duplicates on SDS-PAGE gel using a mini-electrophoresis apparatus (Bio-Rad Laboratories, Inc.). The resolved polypeptides were transferred onto a nitrocellulose membrane in Tris-glycine buffer containing 25% methanol. The membranes were blocked with 5% dried milk, and then incubated with goat anti-MMP-8 (SantaCruz), rabbit anti-MMP-9 (Abcam) or rabbit anti-MT1MMP (Abcam) antibodies. Rabbit anti-GAPDH (SantaCruz) was included in each procedure to avoid inter-assay variations. Nitrocellulose membranes were incubated with goat anti-rabbit HRP conjugated antibody (Abcam), or bovine anti-goat HRP (Sigma). Membranes were developed using EZ-ECL chemiluminescence detection kit (Biological industries). A molecular mass protein standard (PageRuler Prestained Protein ladder, Fermentas) was included in each assay.

Lung Preparation for Imaging:

Lungs were inflated by using PBS for in situ zymography or 4% PFA for other imaging purposes. This was done by exposing the trachea, inserting a cannula 22G, 0.8×25 mm, (Cathy IV cannula, HMD Healthcare LTD) and injecting 5 ml fluid. The cannula was ligated to the trachea to avoid spillage. Mouse lungs were harvested at different time points post infection, embedded in OCT and frozen in −80° C. until analyzed.

Two-Photon Microscopy and Second Harmonics Generation:

Before imaging, lungs were cut 300 μm and immediately visualized using a two-photon microscope in the in-vivo imaging unit in the Weizmann institute (2 PM:Zeiss LSM 510 META NLO; equipped with a broadband Mai Tai-HP-femtosecond single box tunable Ti-sapphire oscillator, with automated broadband wavelength tuning 700-1,020 nm from Spectraphysics, for two-photon excitation). For collagen second harmonic imaging a wavelength of 800 nm was used (detection at 400 nm).

AirSEM and SEM Imaging of Intact Lung Tissues and Lung ECM Scaffolds:

Fixed lungs were sectioned into 300 μm sections. Sections were washed three times in a large volume of PBS to remove OCT remnants, followed by three DDW washes. For tissue imaging, the slices were gently placed on a SuperFrost Plus glass slides and stained as previously described. Briefly, sections were washed with DDW and stained with 0.1% ruthenium red (EM grade, Sigma-Aldrich) in a 0.1 M sodium cacodylate buffer pH 7.4 (analytical standard, Sigma-Aldrich) for 15 min. The sections were then thoroughly washed with DDW and stained with a 2% uranyl acetate solution for 10 min. The samples were then washed with DDW and allowed to dry in the air at room temperature for 5-7 min before airSEM™. ECM scaffolds were first de-cellularized using 0.5% EDTA supplemented with 2% triton for 24 hours. Staining was done as previously described. For conventional scanning electron microscopy (SEM) samples were further dehydrated through an ethanol series increasing in concentration to 100% ethanol, were dried in a critical point dryer and coated by Au/Palladium according to standard sample preparation procedure for SEM imaging with an Ultra 55 Feg Zeiss SEM operating at 2 kV.

Immunohistochemistry:

Immunohistochemistry was performed using standard techniques on 10 μm cryo-sections. Sections were fixed with 4% PFA, blocked with 3% BSA, incubated overnight with primary rabbit anti-laminin (Sigma), or rabbit anti-lumican (abcam), or rabbit anti-collagen IV or rat antibody for F4/80 and CD45 cell surface protein (abcam). LEM2/15 was conjugated to Alexa Fluor 555 Protein by Labeling Kit (Molecular Probes), according to manufacturer's instructions. Sections were then washed with PBS, incubated with a goat anti-rabbit HRP conjugated (Jackson). Fluorescein or Cy3 conjugated anti-HRP kit was used (Perkin Ehlmer) respectively, followed by DAPI staining (Sigma) and mounting with immune-mount (Thermo Scientific). Samples were imaged using Nikon 80i eclipse microscope.

Collagen Type I in Situ Zymography:

Non-fixed lungs samples were cut into 10 μm sections, gently washed to remove OCT. After washing a 1 mg/ml DQ collagen type I (Molecular Probes) was diluted to 40 mg/ml with developing buffer (50 mM Tris (pH 7.5), 100 mM NaCl, 5 mM $CaCl_2$). Samples were incubated for 4 hours at 37° C. the reaction was stopped with 4% paraformaldehyde and followed by the desired immune-staining, mounted with immune-mount (Thermo Scientific) and imaged using Nikon 80i eclipse microscope.

Relative Frequency of Fiber Orientation Analysis:

Imaging analysis was done by Fiji package, Directionality analysis. Graphs were plotted using GraphPad Prism 6. The relative frequency of fiber spatial orientation was measured using the "Directionality" plugin analysis tool in Fiji package version 6.1.1.

Flow Cytometry:

Lungs from infected and control uninfected C57BL/6J mice were immersed in cold PBS, cut into small pieces in 5 ml DMEM containing 10% bovine fetal serum (FACS buffer). Cell suspensions were grinded using 1-ml syringe cup on a 70-lm cell strainers (BD Falcon). Cells were washed with ice-cold PBS. Remaining red blood cells were lysed using ammonium chloride solution (Sigma). Cells were harvested and immersed 1 ml FACS buffer [PBS+2% FCS, 1 mM EDTA]. Lung cells were stained with antibodies against multiple surface antigens: PE-conjugated LEM 2/15 (anti-mouse MT1-MMP ab), PerCP/cy5.5-conjugated anti-mouse CD45 (clone—F11) or Pacific blue-anti-mouse CD45, APC-Cy7-conjugated EPCAM, APC-conjugated anti-CD11b, PerCP/cy5.5-anti-mouse Ly6C, FITC-anti-mouse Ly6G (clone 1A8), FITC-anti-mouse NKp46, FITC-anti-mouse-TCR-β. Flow cytometry was performed using FACSAriaIII Flow Cytometer (BD biosciences), and data was analyzed using FlowjoV 10.0.8 software. Sorted cells from non-infected control and infected mice treated with PBS were further subjected to RNA extraction, as previously mentioned in RNA extraction section, and were sequenced using RNA-Seq profiling and qPCR.

Example 1

Extra Cellular Matrix Genes are Induced During Influenza Infection

Figure 1A:
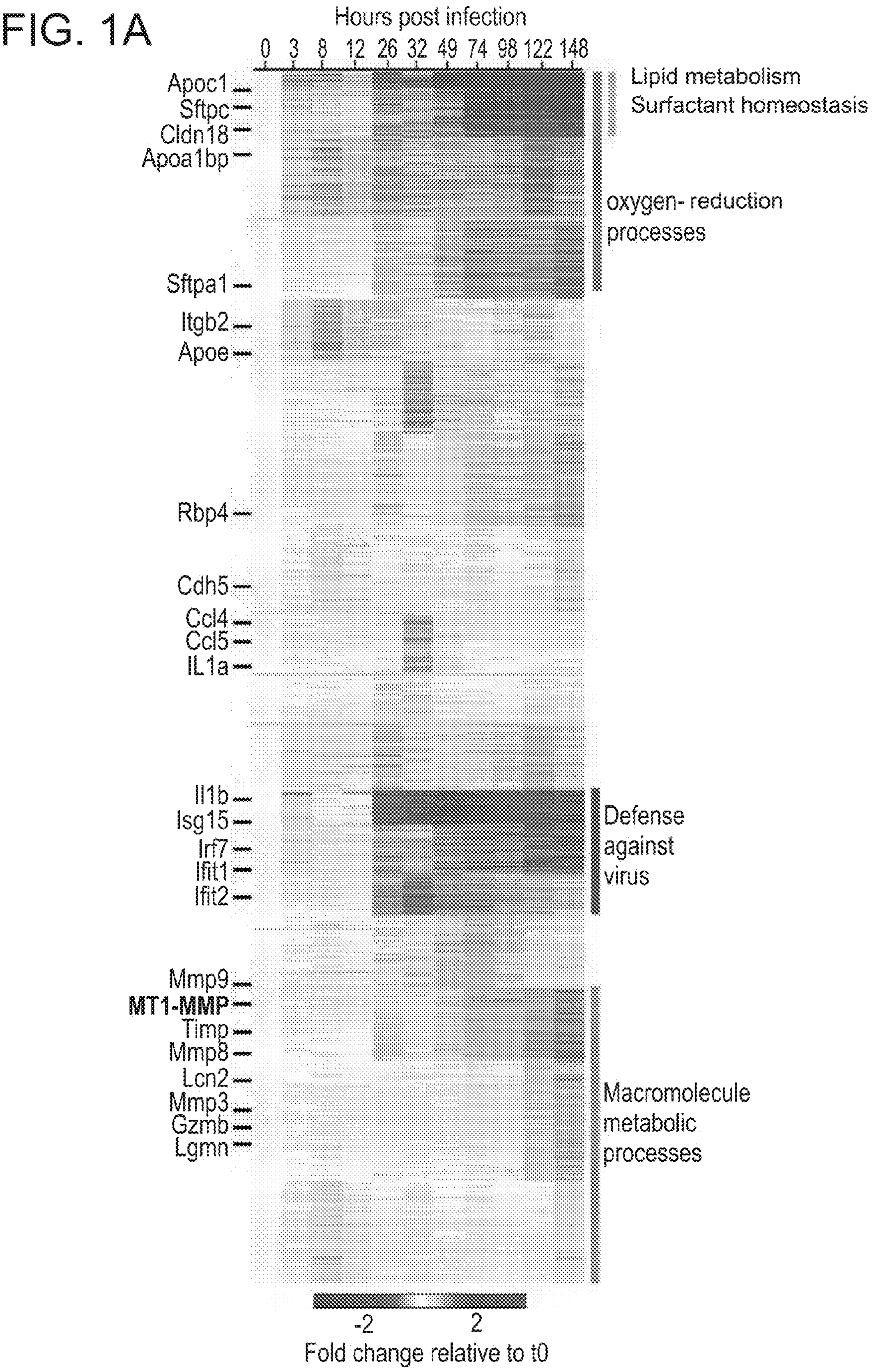
Figure 6A:
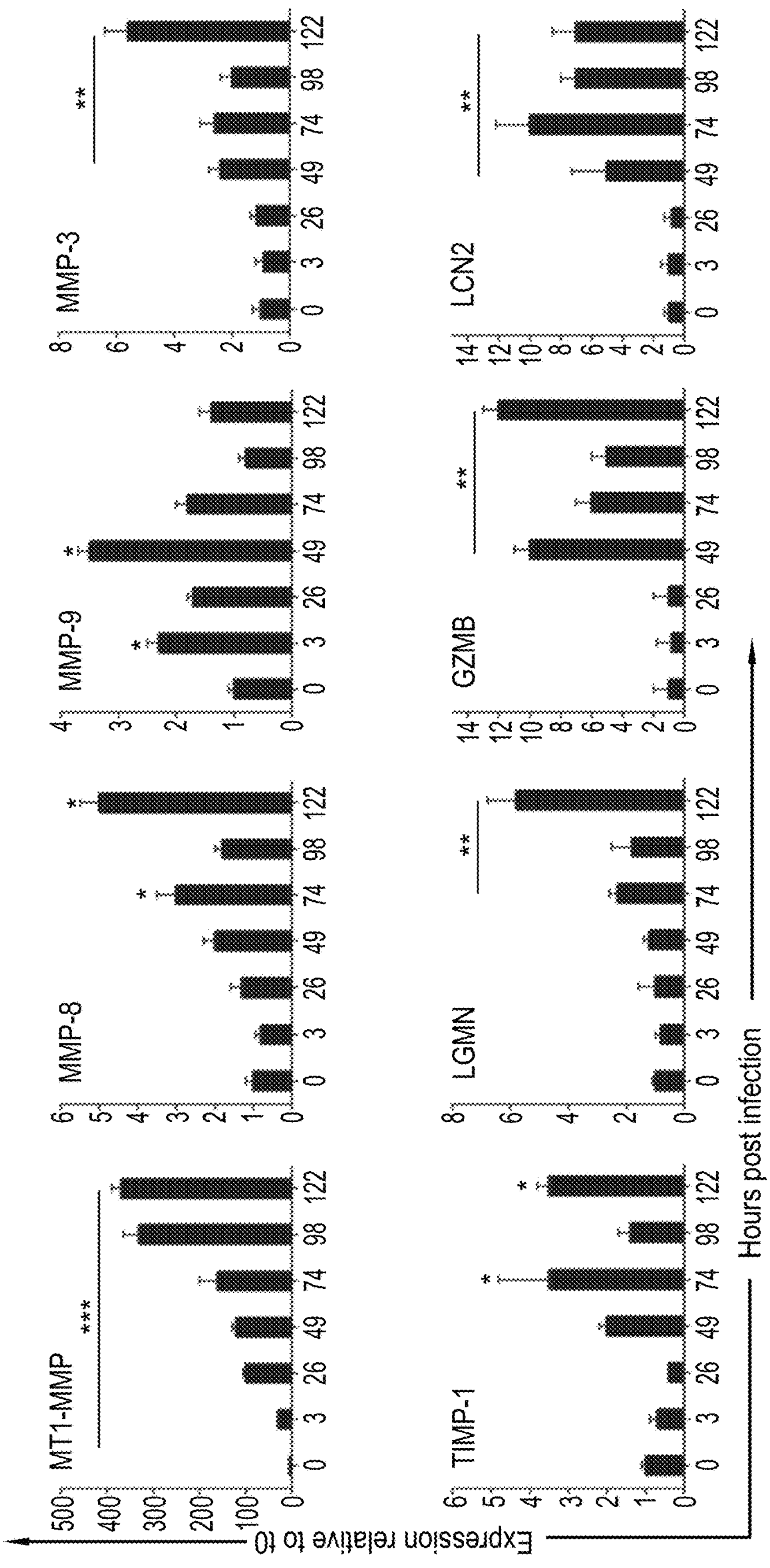
Figure 6B:
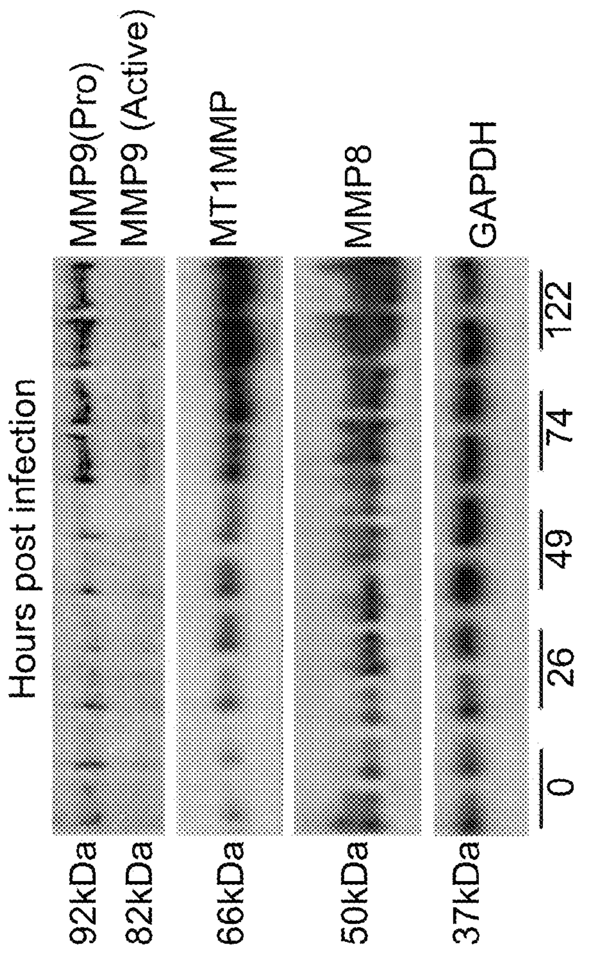
Figure 6C:
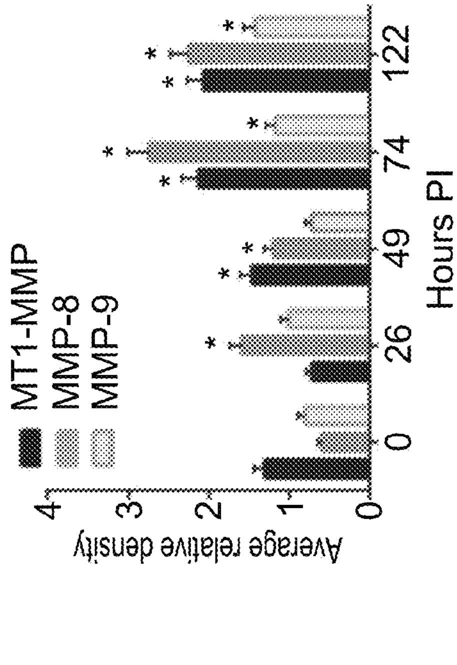
Figure 6D:
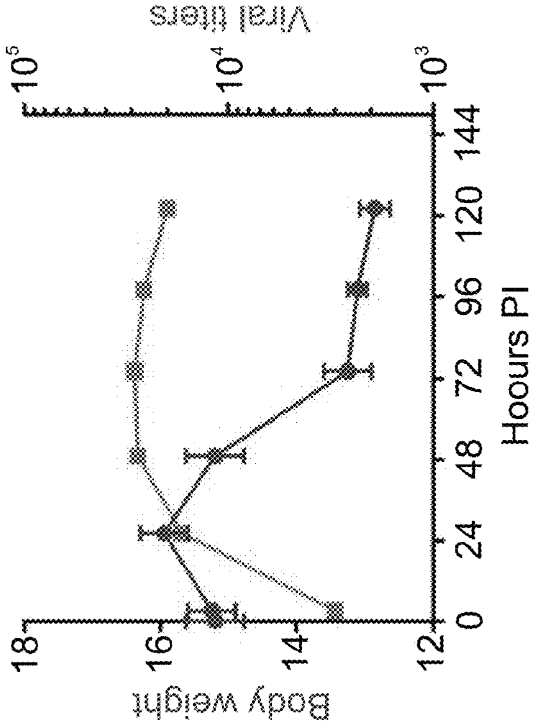

In order to systematically describe the effect of influenza inflection on host ECM circuits, genome-wide RNA-seq was used to measure the temporal transcriptional response of whole lung tissue during a seven-day course of influenza (Altbourn et al., 2014). Gene expression was measured at ten time points following infection. C57BL/6 mice were infected by intranasal inoculation of mouse-adapted PR8 influenza A H1N1 virus using either lethal or sub-lethal dosages. PR8 infection is widely used as a influenza infection model (Morens et al., 2008; Tate et al., 2011; Taubenberger and Morens, 2006; Watanabe et al., 2013) consisting of rigorous alveolar spread, acute pulmonary hemorrhage and intensive host responses. Along with the disease progression, the symptoms and loss of body weight are initiated 24-48 hours post infection with an increase in viral load in the lungs (FIG. 6D). As expected, influenza infection resulted in induction of genes that are involved in inflammation chemotaxis (CXCL1, CXCL10, Il1b, Il1r), defense against viral infection (ISG15, IFNB1, IRF7, IFIT1 and IFIT3) and various chemokines (CCL2, CCL3, CCL4, CXCL2) as well as down-regulation of genes related to lung homeostasis (secretoglobins and relevant transcription factors (e.g. NK×2.1)) (FIG. 1A). Furthermore, many genes which were down-regulated following infection belong to oxygen-reduction processes, surfactant homeostasis (SFTPA1, SFTPC), cell-cell adhesion molecules such as integrins, cadherin, claudin (CLDN18, ITGB2, CDH5) and lipid metabolism (APOE, APOC1, APOA1BP). Additional genes that were statistically significantly up-regulated are set forth in Table 2B herein below.

TABLE 2B

| Symbols | Genes (mouse) |
|---|---|
| 1190002H23RIK | NM_025427 |
| 1500012F01RIK | NM_001081005 |
| 2010001M09RIK | NM_027222 |
| AA467197 | NM_001004174 |
| Acta1 | NM_009606 |
| Actb | NM_007393 |
| Adam15 | NM_001037722 |
| Adam8 | NM_007403 |
| Adamts15 | NM_001024139 |
| Adamts4 | NM_172845 |
| Aif1 | NM_019467 |
| Alpl | NM_007431 |
| Angptl4 | NM_020581 |
| Apod | NM_007470 |
| Apol6 | NM_028010 |
| Apol9a | NM_001162883 |
| Apol9b | NM_173743 |
| Arrb2 | NM_145429 |
| Atf3 | NM_007498 |
| AW112010 | NM_001177351 |
| B2m | NM_009735 |
| B4galt1 | NM_022305 |
| Bak1 | NM_007523 |
| Batf2 | NM_028967 |
| Bcl3 | NM_033601 |
| Bdkrb1 | NM_007539 |
| Bgn | NM_007542 |
| Bst2 | NM_198095 |
| C1qa | NM_007572 |
| C1qb | NM_009777 |
| C1qc | NM_007574 |
| C1qtnf6 | NM_028331 |
| C3ar1 | NM_009779 |
| Casp4 | NM_007609 |
| Ccl2 | NM_011333 |
| Ccl20 | NM_001159738 |
| Ccl4 | NM_013652 |
| Ccl5 | NM_013653 |
| Ccl7 | NM_013654 |
| Cd274 | NM_021893 |
| Cd300lf | NM_001169153 |
| Cd3d | NM_013487 |
| Cd72 | NM_001110322 |
| Cd8a | NM_009857 |
| Cd8b1 | NM_009858 |
| Cdca3 | NM_013538 |
| Cdkn1a | NM_007669 |
| Cebpd | NM_007679 |
| Cfb | NM_001142706 |
| Cidea | NM_007702 |
| Ckap4 | NM_175451 |
| Ckm | NM_007710 |
| Cldn4 | NM_009903 |
| Cmklr1 | NM_008153 |
| Cmpk2 | NM_020557 |
| Col1a1 | NM_007742 |
| Col1a2 | NM_007743 |
| Col3a1 | NM_009930 |
| Cox7a1 | NM_009944 |
| Cpxm1 | NM_019696 |
| Csrnp1 | NM_153287 |
| Ctgf | NM_010217 |
| Ctps | NM_016748 |

TABLE 2B-continued

| Symbols | Genes (mouse) |
|---|---|
| Ctss | NM_021281 |
| Ctsz | NM_022325 |
| Cxcl1 | NM_008176 |
| Cxcl10 | NM_021274 |
| Cxcl12 | NM_021704 |
| Cxcl13 | NM_018866 |
| Cxcl16 | NM_023158 |
| Cxcl2 | NM_009140 |
| Cxcl5 | NM_009141 |
| Cxcl9 | NM_008599 |
| Cyp4f18 | NM_024444 |
| Cyr61 | NM_010516 |
| Daxx | NM_001199733 |
| Dbp | NM_016974 |
| Ddit4 | NM_029083 |
| Ddx58 | NM_172689 |
| Dhx58 | NM_030150 |
| Dntt | NM_009345 |
| Dtx31 | NM_001013371 |
| Ecm1 | NM_007899 |
| Edem1 | NM_138677 |
| Eif2ak2 | NM_011163 |
| Eln | NM_007925 |
| Epha2 | NM_010139 |
| Epsti1 | NM_029495 |
| F3 | NM_010171 |
| Fam26f | NM_175449 |
| Fbn1 | NM_007993 |
| Fcer1g | NM_010185 |
| Fcgr1 | NM_010186 |
| Fcgr4 | NM_144559 |
| Fgfr1 | NM_001079908 |
| Fkbp5 | NM_010220 |
| Flnb | NM_134080 |
| Fn1 | NM_010233 |
| Fscn1 | NM_007984 |
| Fst | NM_008046 |
| Fxyd5 | NM_001111073 |
| Gadd45g | NM_011817 |
| Gbp10 | NM_001039646 |
| Gbp2 | NM_010260 |
| Gbp3 | NM_018734 |
| Gbp4 | NM_008620 |
| Gbp5 | NM_153564 |
| Gbp6 | NM_194336 |
| Gbp9 | NM_172777 |
| Glycam1 | NM_008134 |
| Gm12250 | NM_001135115 |
| Gm13889 | NM_001145034 |
| Gm14446 | NM_001101605 |
| Gm4841 | NM_001034859 |
| Gm4951 | NM_001033767 |
| Gpd1 | NM_010271 |
| Gpx3 | NM_008161 |
| Grn | NM_008175 |
| Gvin1 | NM_001039160 |
| Gzmb | NM_013542 |
| H2-Q7 | NM_010394 |
| H2-Q9 | NM_001201460 |
| H2-T10 | NM_010395 |
| H2-T22 | NM_010397 |
| H2-T23 | NM_010398 |
| H2-T9 | NM_010399 |
| Has1 | NM_008215 |
| Hcls1 | NM_008225 |
| Helz2 | NM_183162 |
| Hmga1 | NM_001166537 |
| Hmga1-rs1 | NM_001166477 |
| Hspa8 | NM_031165 |
| I830012O16Rik | NM_001005858 |
| Ier5 | NM_010500 |
| Ifi203 | NM_001045481 |
| Ifi204 | NM_008329 |
| Ifi205 | NM_172648 |
| Ifi2712a | NM_029803 |
| Ifi35 | NM_027320 |
| Ifi44 | NM_133871 |
| Ifi47 | NM_008330 |

TABLE 2B-continued

| Symbols | Genes (mouse) |
|---|---|
| Ifih1 | NM_027835 |
| Ifit1 | NM_008331 |
| Ifit2 | NM_008332 |
| Ifit3 | NM_010501 |
| Ifitm3 | NM_025378 |
| Igtp | NM_018738 |
| Iigp1 | NM_001146275 |
| Il10ra | NM_008348 |
| Il18bp | NM_010531 |
| Il1b | NM_008361 |
| Il1rn | NM_001039701 |
| Il21r | NM_021887 |
| Irf1 | NM_001159396 |
| Irf5 | NM_012057 |
| Irf7 | NM_016850 |
| Irf8 | NM_008320 |
| Irg1 | NM_008392 |
| Irgm1 | NM_008326 |
| Irgm2 | NM_019440 |
| Isg15 | NM_015783 |
| Isg20 | NM_020583 |
| Itga5 | NM_010577 |
| Junb | NM_008416 |
| Kcnn4 | NM_001163510 |
| Krt13 | NM_010662 |
| Krt4 | NM_008475 |
| Laptm5 | NM_010686 |
| Lars2 | NM_153168 |
| Lck | NM_001162433 |
| Lcn2 | NM_008491 |
| Lgals3bp | NM_011150 |
| Lgals9 | NM_001159301 |
| Lgmn | NM_011175 |
| Lilrb4 | NM_013532 |
| Lox | NM_010728 |
| Loxl1 | NM_010729 |
| Loxl2 | NM_033325 |
| Loxl3 | NM_013586 |
| Ly6a | NM_010738 |
| Ly6c1 | NM_010741 |
| Ly6c2 | NM_001099217 |
| Ly6i | NM_020498 |
| Lyve1 | NM_053247 |
| Mmp14 | NM_008608 |
| Mmp3 | NM_010809 |
| Mmp8 | NM_008611 |
| Mnda | NM_001033450 |
| Mndal | NM_001170853 |
| Mpeg1 | NM_010821 |
| Ms4a4b | NM_021718 |
| Ms4a4c | NM_029499 |
| Ms4a6b | NM_027209 |
| Ms4a6c | NM_028595 |
| Ms4a6d | NM_026835 |
| Mt1 | NM_013602 |
| Mt2 | NM_008630 |
| Mx1 | NM_010846 |
| Mx2 | NR_003508 |
| Mxd1 | NM_010751 |
| Myh1 | NM_030679 |
| Myh8 | NM_177369 |
| Mylpf | NM_016754 |
| Nampt | NM_021524 |
| Nfkbia | NM_010907 |
| Nlrc5 | NM_001033207 |
| Nppa | NM_008725 |
| Nt5c3 | NM_026004 |
| Oas1a | NM_145211 |
| Oas1g | NM_011852 |
| Oas2 | NM_145227 |
| Oasl1 | NM_145209 |
| Oasl2 | NM_011854 |
| Ogfr | NM_031373 |
| Parp12 | NM_172893 |
| Parp14 | NM_001039530 |
| Parp9 | NM_030253 |
| Per1 | NM_001159367 |
| Pfkfb3 | NM_001177757 |

TABLE 2B-continued

| Symbols | Genes (mouse) |
|---|---|
| Phf11b | NM_001164327 |
| Phf11d | NM_199015 |
| Pirb | NM_011095 |
| Pla2g7 | NM_013737 |
| Plac8 | NM_139198 |
| Plat | NM_008872 |
| Plau | NM_008873 |
| Pld4 | NM_178911 |
| Pnp | NM_013632 |
| Pnp2 | NM_001123371 |
| Pou2af1 | NM_011136 |
| Ppa1 | NM_026438 |
| Prmt1 | NM_019830 |
| Prss22 | NM_133731 |
| Psmb10 | NM_013640 |
| Psmb8 | NM_010724 |
| Psme2 | NM_011190 |
| Pstpip1 | NM_011193 |
| Ptafr | NM_001081211 |
| Ptk7 | NM_175168 |
| Ptx3 | NM_008987 |
| Pycard | NM_023258 |
| Pyhin1 | NM_175026 |
| Qsox1 | NM_001024945 |
| Relb | NM_009046 |
| Retnla | NM_020509 |
| Rhox8 | NM_001004193 |
| Rpsa | NM_011029 |
| Rsad2 | NM_021384 |
| Rtp4 | NM_023386 |
| S100a14 | NM_001163526 |
| S100a4 | NM_011311 |
| S100a6 | NM_011313 |
| S100a8 | NM_013650 |
| S100a9 | NM_009114 |
| Saa1 | NM_009117 |
| Saa3 | NM_011315 |
| Samd9l | NM_010156 |
| Samhd1 | NM_001139520 |
| Sbno2 | NM_183426 |
| Sdc3 | NM_011520 |
| Sell | NM_001164059 |
| Sema7a | NM_011352 |
| Serinc3 | NM_012032 |
| Serpina3f | NM_001033335 |
| Serpina3g | NM_009251 |
| Serpina3m | NM_009253 |
| Serpina3n | NM_009252 |
| Serpine1 | NM_008871 |
| Serping1 | NM_009776 |
| Sfn | NM_018754 |
| Sh3pxd2b | NM_177364 |
| Slc15a3 | NM_023044 |
| Slc25a37 | NM_026331 |
| Slc7a5 | NM_011404 |
| Slfn1 | NM_011407 |
| Slfn2 | NM_011408 |
| Slfn4 | NM_011410 |
| Slfn5 | NM_183201 |
| Slfn8 | NM_001167743 |
| Slfn9 | NM_172796 |
| Snx32 | NM_001024560 |
| Socs1 | NM_009896 |
| Socs3 | NM_007707 |
| Sparcl1 | NM_010097 |
| Sphk1 | NM_011451 |
| Spp1 | NM_009263 |
| Sprr1a | NM_009264 |
| Stat1 | NM_009283 |
| Stat2 | NM_019963 |
| Tap1 | NM_013683 |
| Tap2 | NM_011530 |
| Tapbp | NM_001025313 |
| Tcf7 | NM_009331 |
| Tgfbi | NM_009369 |
| Tgm2 | NM_009373 |
| Tgtp1 | NM_011579 |
| Tgtp2 | NM_001145164 |

TABLE 2B-continued

| Symbols | Genes (mouse) |
|---|---|
| Thbs1 | NM_011580 |
| Themis2 | NM_001033308 |
| Thrsp | NM_009381 |
| Thy1 | NM_009382 |
| Timp1 | NM_001044384 |
| Tinagl1 | NM_001168333 |
| Tnc | NM_011607 |
| Tnfaip2 | NM_009396 |
| Tnfrsf12a | NM_013749 |
| Tnni2 | NM_009405 |
| Tor3a | NM_023141 |
| Tpm2 | NM_009416 |
| Trafd1 | NM_172275 |
| Trex1 | NM_011637 |
| Trib1 | NM_144549 |
| Trim25 | NM_009546 |
| Trim30a | NM_009099 |
| Tuba1c | NM_009448 |
| Tubb5 | NM_011655 |
| Tubb6 | NM_026473 |
| Ubc | NM_019639 |
| Ucp1 | NM_009463 |
| Usp18 | NM_011909 |
| Vcan | NM_001134475 |
| Wars | NM_001164488 |
| Xaf1 | NM_001037713 |
| Xdh | NM_011723 |
| Zbp1 | NM_021394 |
| Znfx1 | NM_001033196 |

Figure 1B:
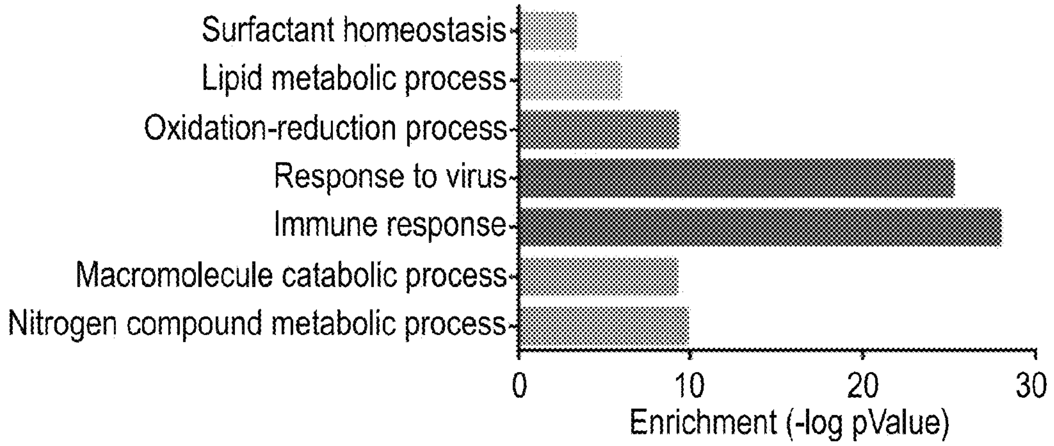
Figure 1C:
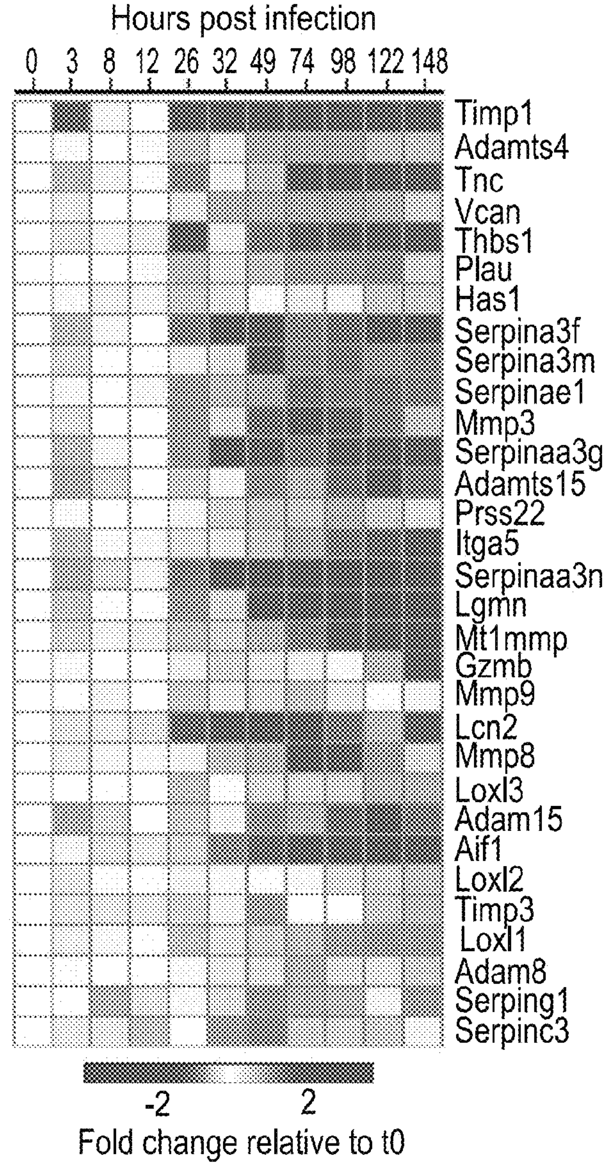
Figure 1D:
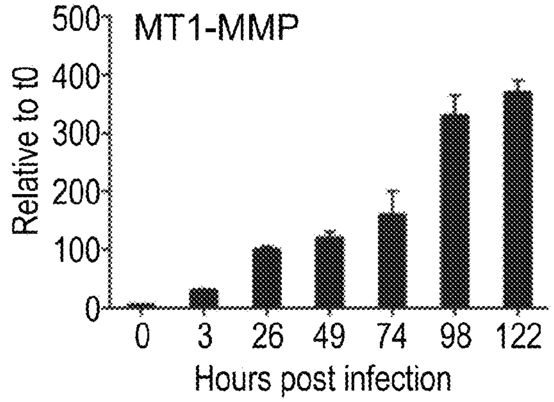

Of special notice was a large group of genes involved in ECM remodeling including macromolecule metabolism and protease synthesis (FIG. 1A). Remarkably, this group of genes was highly over-represented throughout infection, exhibiting a wide panel of pathways involved in multiple ECM remodeling events (FIG. 1A-1C). An enrichment of functional categories relating to extra cellular modulators involved in proteolysis, collagen remodeling and catabolism, fibrinolysis, wound healing, homeostasis and cell migration ($p \leq 10^4$) was uncovered, peaking 74 hours post infection (FIG. 1B). All together, 479 out of 3530 differentially expressed genes (13.6%) are related to ECM remodeling. These included serine proteases, lysyl oxidases, cathepsins, disintegrins (ADAMs), metalloproteinases (MMPs) and their natural inhibitors (TIMPs), which serve as ECM modifiers that determine the turnover of different ECM components. Within this group of genes, robust induction of MT1-MMP at both the RNA (400 fold change; FIG. 1D) and protein levels 48 hours post infection (FIG. 6A-B) was found. Using quantitative real time PCR, the temporal changes in MT1-MMP expression was corroborated as well as other representative genes belonging to the MMP family (MMP -3, 8 and 9) and modulating the ECM (FIG. 6A, 6B, 6C).

Example 2

MTI-MMP Expression is Induced in Myeloid Cells Post Influenza Infection

Figure 7A:
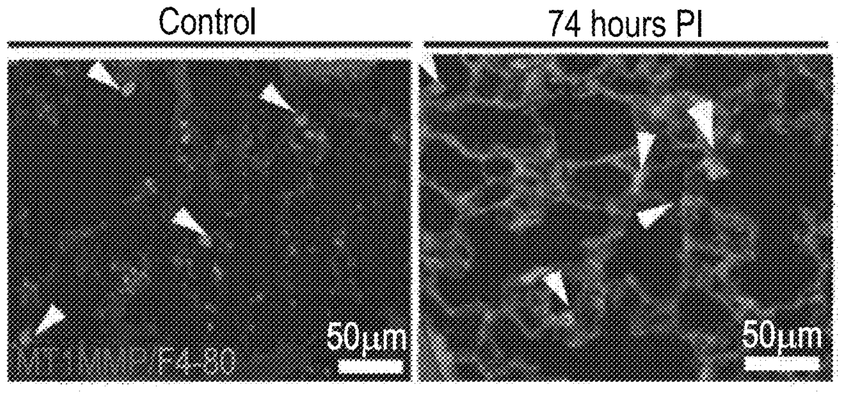
Figure 7B:
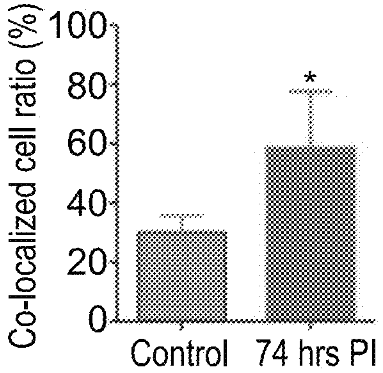
Figure 7C:
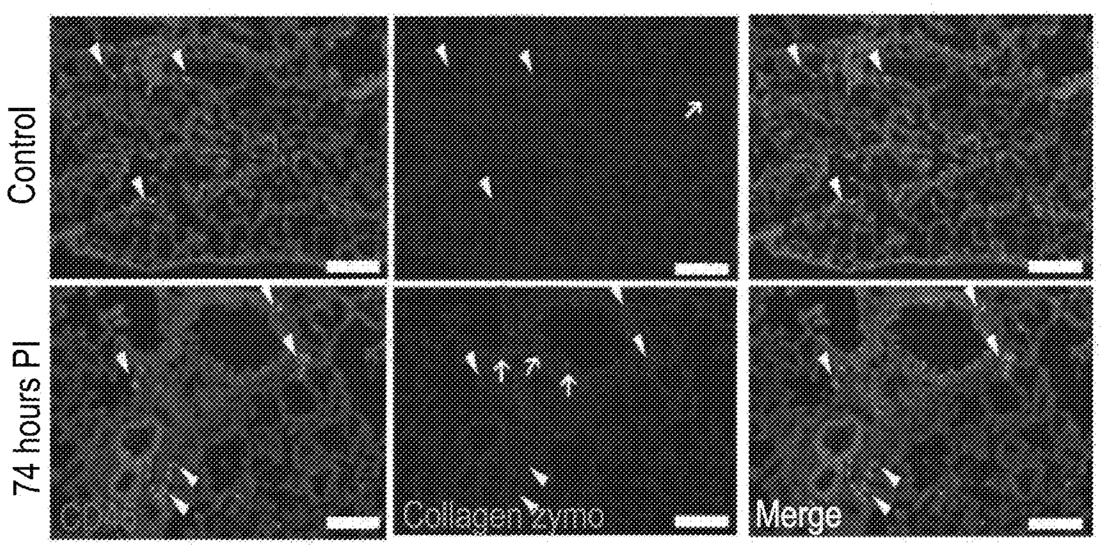
Figure 7D:
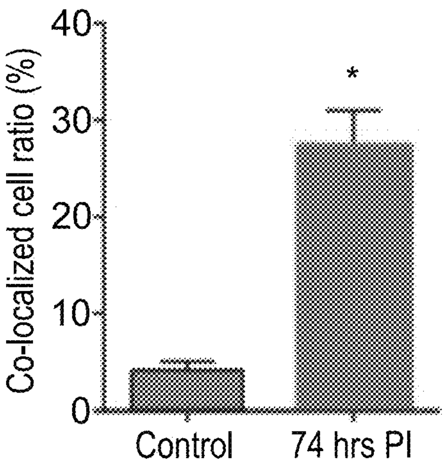

In order to identify the cell population acting as the source of MT1-MMP during infection course by flow cytometry was performed. Of the population of cells expressing MT1-MMP in the non-infected lung, the overwhelming majority was non-hematopoietic cell population ($CD45^-$, 89.5%), while only 10.5% were of hematopoietic origin ($CD45^+$) (FIG. 2A). Post infection, the CD45+MT1-MMP expressing population increased four-fold (40.9%). Specifically, the $CD11b^+$.$MT1\text{-}MMP^+$ portion of the immune cells increased from 32.9% to 64.9%, while the non-hematopoietic ($CD45^-$) MT1-MMP-expressing cells decreased by two-fold (FIG. 2A). Histogram plots (FIG. 2B) further show that the overall increase in MT1-MMP expression post infection (FIG. 2B) can be associated with increased expression of MT1-MMP in CD11b+ cells (FIG. 2B), rather than lung epithelial cells, in which MT1-MMP was reduced post infection (FIG. 2B). MT1-MMP expression in $CD45^+$ versus $CD45^-$ sorted populations before and during infection was further validated at the RNA level using qPCR (FIG. 2C). Immunostaining for MT1-MMP as well as F4/80 markers in influenza-infected lungs confirm our observation that MT1-MMP expressing cells largely co-localize with F4/80 positive cells at 74 hours post infection. Since macrophages are both CD11b+ and F4/80+ immune cells, these findings suggest that macrophages are a significant source of MT1-MMP following infection (FIG. 7A arrow heads, 7B). In order to monitor the collagenase activity of influenza-infected lungs, in situ zymography was used. It was found that following infection, collagenolytic activity is mostly associated with CD45+ cells, as well as $CD45^-$ cells lining the bronchi of infected lungs (FIG. 7C arrows, D).

In order to further characterize the MT1-MMP-expressing populations before and after (74 hours) infection, RNA-seq analysis was performed on sorted MT1-MMP-expressing CD45+ and $CD45^-$ subpopulations. In total, 2169 genes were found to be differentially expressed in cells post-infection as compared to un-infected cells in both CD45+ and $CD45^-$ populations (FIG. 8). Consistent with the analysis from whole lung RNA-seq, an increase in activation of inflammatory signaling pathways and cytokine production in both immune (CD45+) and stromal ($CD45^-$) cells expressing MT1-MMP following infection was observed (FIG. 8). The immune cells, in particular, exhibited significant up-regulation of cytokines (CCL2, CCL3, CCL4, CXCL2, IL1b) and anti-viral response genes (e.g. SLFN4, IFIT1 and IFIT2), while the stromal cells exhibited down-regulation of genes associated with lung homeostatic functions such as surfactant production (e.g. SFTPB, SFTPC). The immune population showed increase in expression of monocyte/macrophage/DC markers (e.g. CD11b) and decrease of multiple B cell markers (e.g. CD19, CD37, CD79). Thus, MT1-MMP expression post-infection is associated with activated immune cells from the myeloid compartment (FIG. 8).

Example 3

Influenza Infection Induces Destruction of ECM Morphology and Composition

Figures 9A, 9B, 9C, 9D:
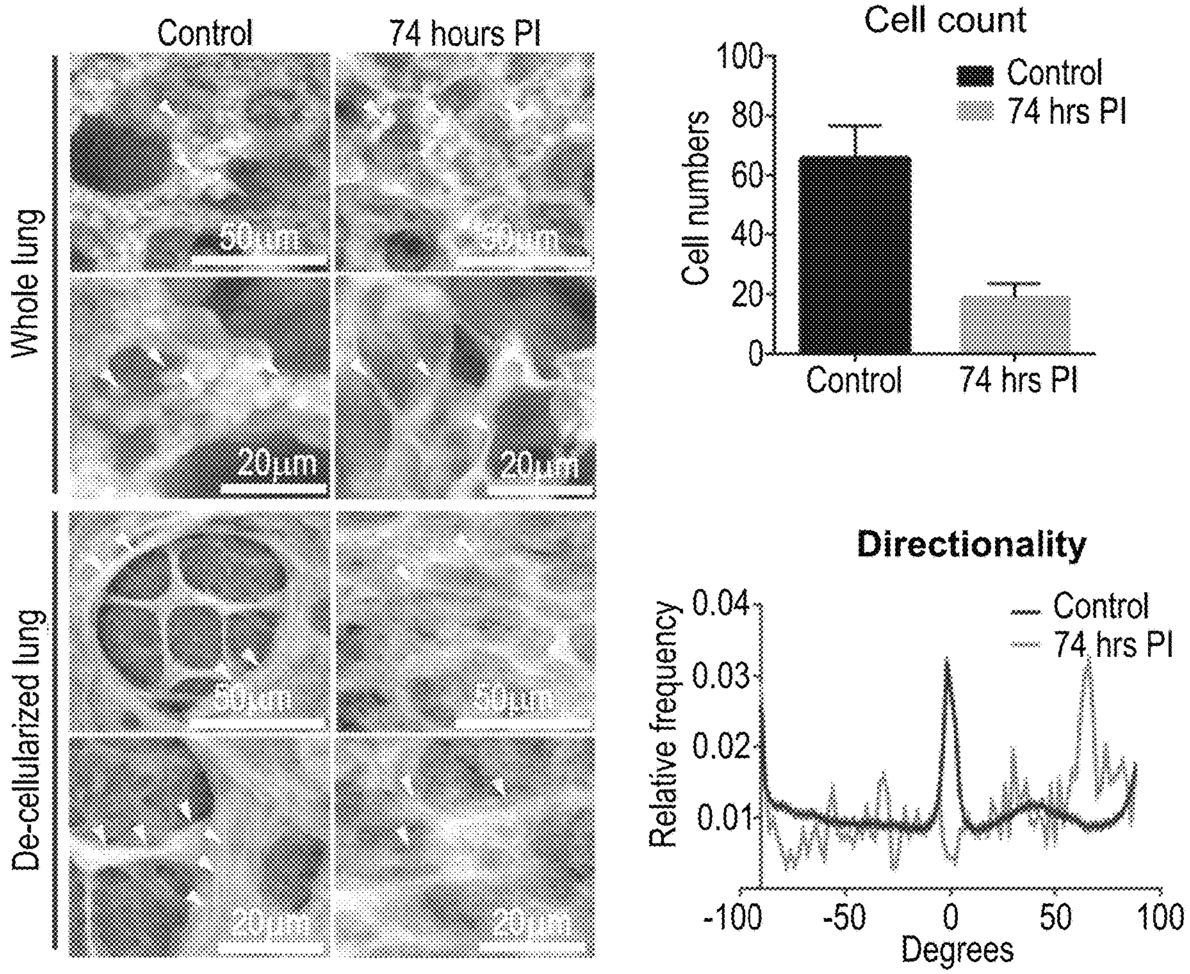

MT1-MMP plays a major role in cancer-associated invasion processes through degradation of fibrillar collagen, laminin and other ECM components. To evaluate the functional role of MT1-MMP in influenza infection, mass spectrometry analysis (FIG. 3A) as well as scanning electron microscopy (SEM) imaging of lung tissues devoid of its cellular compartment (de-cellularized) before and after infection was performed (FIGS. 9A-9B). SEM analysis of influenza-infected lungs showed massive distortion of ECM morphology (FIGS. 3B-3C) as well as rearrangement of collagen fibers, specifically in the alveolar walls. At 74 hours post-infection, collagen bundles on the boundaries of alveolar sacs displayed unraveled fiber ends and dispersed orientation angles (FIG. 3B). This was further confirmed by measuring the orientation of the fibrils composing the alveolar walls (FIG. 3C). In addition, the alveolar space and septa were distorted in the infected lungs (FIG. 3B). To validate these results and further analyze the integrity of the whole tissue—including the cells and ECM in their native environment—during infection, a novel form of electron microscopy imaging, AirSEM (Solomonov et al., 2014) was used. AirSEM enables visualization of native hydrated tissues in ambient conditions, thus avoiding potential artifacts associated with sample preparation for SEM. Imaging of virally-infected lung tissues exhibited tissue destruction characterized by both alveolar and bronchial cell depletion as well as distortion of alveolar sacs and ducts followed by alveolar wall thinning (FIGS. 9A-9B). Finally, AirSEM imaging of fresh lung ECM scaffolds (de-cellularized tissues) showed similar alveolar collagen degradation and distortion patterns as observed in conventional SEM analysis (FIGS. 9A-9B).

Example 4

Figure 3A:
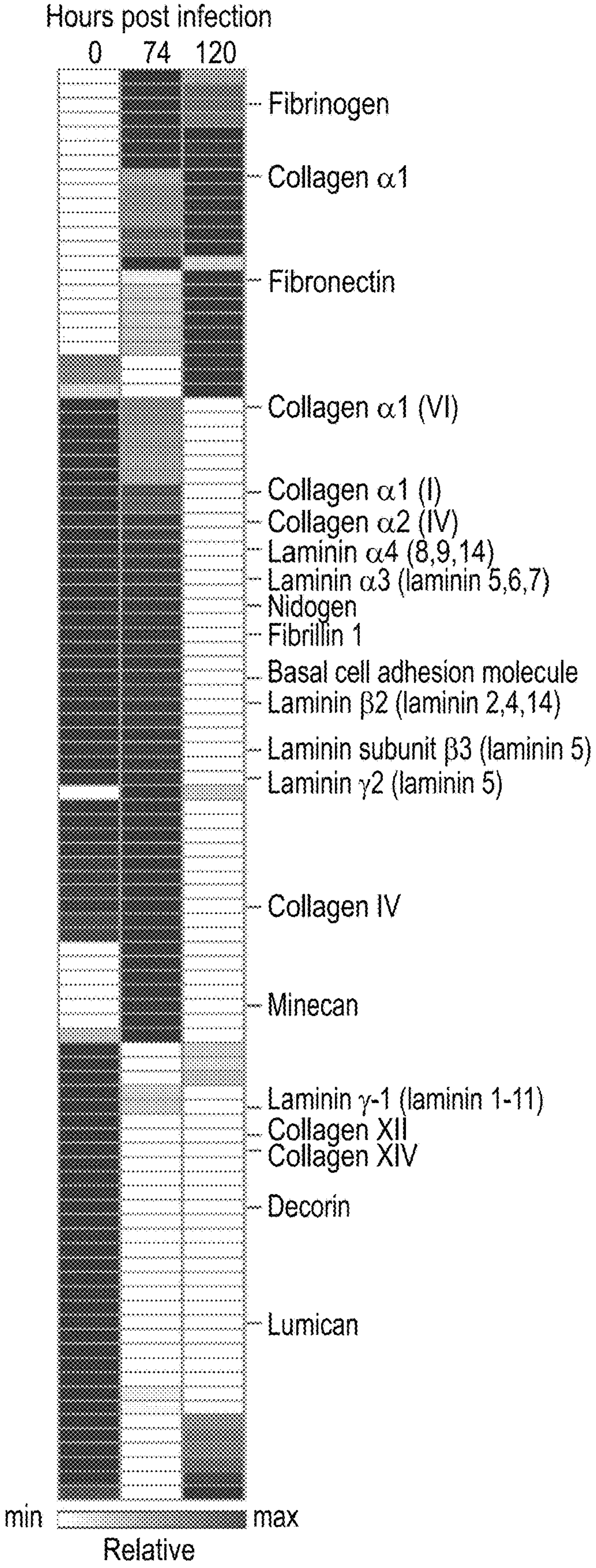
Figure 3B:
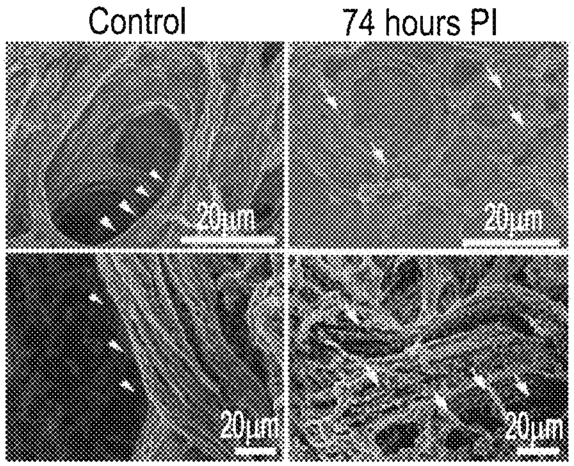
Figure 3C:
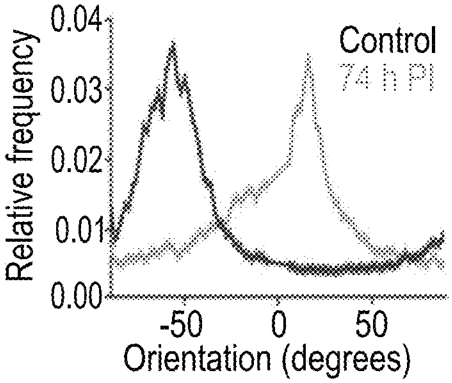
Figure 3D:
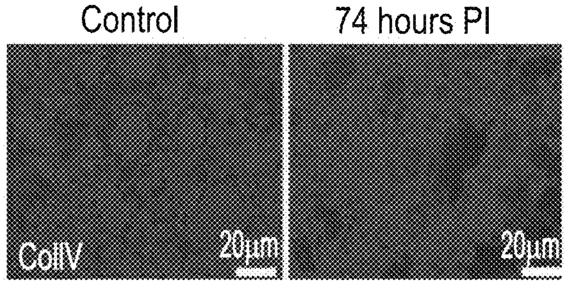
Figure 3E:
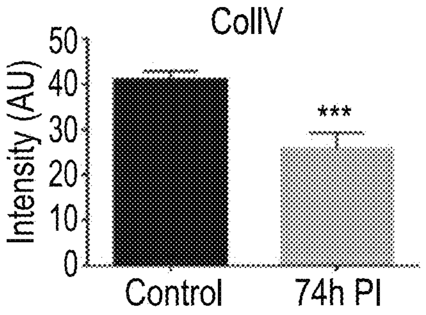
Figure 3F:
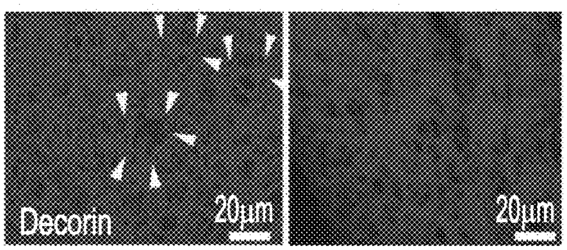
Figure 3G:
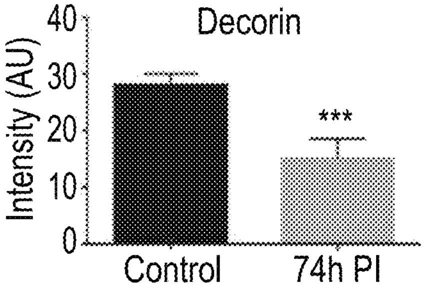
Figure 3H:
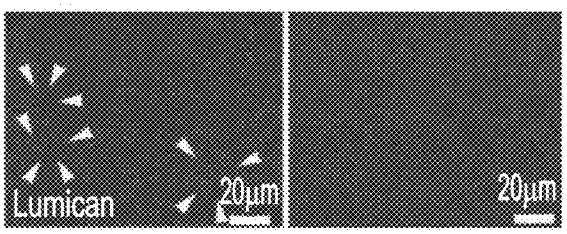
Figure 3I:
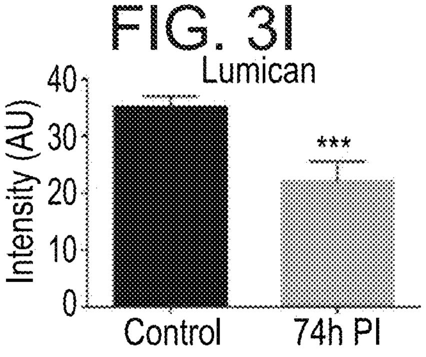

Global Proteomics Analysis Identifies Degradation of ECM Scaffolds During Influenza Infection In order to globally examine the proteolytic implications on ECM remodeling during influenza infection, a tandem mass spectrometry (LC-MS-MS) approach was used (FIG. 3A, Table 3, herein below). Analysis of the de-cellularized lung tissue 74 and 120 hours post infection compared with non-infected tissue showed compositional changes that could be connected to structural changes observed in the architecture of collagen fibrils lining the alveolar wall (FIGS. 3B-3C). Specifically, the proteomic data analysis of the influenza-infected lungs identified modifications in the molecular composition of the ECM, including gradual depletion of collagen and subtypes of laminin molecules (FIG. 3A). In addition, multiple basement-membrane-associated components as well as basal-cell-adhesion molecules (e.g. Nidogen, Decorin, Collagen types IV, XII, XIV and Fibrillin; FIG. 3A) were depleted from infected lung tissue indicating massive transformation of ECM integrity and molecular composition. The loss of representative ECM molecules (Collagen IV, Decorin and Lumican) was confirmed by staining the ECM scaffolds of infected and non-infected lungs (FIGS. 3D-3I). Importantly, several of the components depleted during infection, such as type I collagen, laminin nidogen, lumican, mimecan, fibrillin and decorin, are known MT1-MMP-substrates (Koziol et al., 2012; McQuibban et al., 2000; Noel et al., 2012; Overall, 2002; Shimizu-Hirota et al., 2012; Stegemann et al., 2013). Since multiple MT1-MMP substrates are degraded during the course of influenza infection, it was hypothesized that lung ECM proteolysis and host mortality can be protected by specifically blocking the collagenase activity of MT1-MMP.

TABLE 3

| Protein annotation | Normalized control | Normalized T72 | Normalized T120 |
|---|---|---|---|
| ADP/ATP translocase 1 OS = *Mus musculus* GN = Slc25a4 PE = 1 SV = 4 - [ADT1_MOUSE] | 6.153575947 | 5.977276302 | 0 |
| ADP/ATP translocase 2 OS = *Mus musculus* GN = Slc25a5 PE = 1 SV = 3 - [ADT2_MOUSE] | 6.223198168 | 5.887684499 | 0 |
| Advanced glycosylation end product-specific receptor OS = *Mus musculus* GN = Ager PE = 2 SV = 1 - [C5H3H4_MOUSE] | 6.473725601 | 0 | 0 |
| Agrin OS = *Mus musculus* GN = Agrn PE = 4 SV = 1 - [M0QWP1_MOUSE] | 6.308175158 | 6.593093331 | 6.511599322 |
| Alpha-amylase 1 OS = *Mus musculus* GN = Amy1 PE = 1 SV = 2 - [AMY1_MOUSE] | 0 | 5.65986227 | 7.460711241 |
| Annexin A1 OS = *Mus musculus* GN = Anxa1 PE = 1 SV = 2 - [ANXA1_MOUSE] | 0 | 5.824702042 | 0 |
| Annexin A2 (Fragment) OS = *Mus musculus* GN = Anxa2 PE = 2 SV = 1 - [B0V2N8_MOUSE] | 5.679465046 | 5.957616046 | 6.195405289 |
| Aquaporin-5 OS = *Mus musculus* GN = Aqp5 PE = 2 SV = 1 - [AQP5_MOUSE] | 6.162716299 | 5.961971735 | 0 |
| Basal cell adhesion molecule OS = *Mus musculus* GN = Bcam PE = 2 SV = 1 - [BCAM_MOUSE] | 6.227912096 | 5.999952109 | 0 |
| Basement membrane-specific heparan sulfate proteoglycan core protein OS = *Mus musculus* GN = Hspg2 PE = 2 SV = 1 - [E9PZ16_MOUSE] | 7.415377503 | 7.322287706 | 7.230770907 |
| Beta-actin-like protein 2 OS = *Mus musculus* GN = Actbl2 PE = 1 SV = 1 - [ACTBL_MOUSE] | 6.386138757 | 6.785714287 | 7.052084571 |
| Beta-globin OS = *Mus musculus* GN = Hbb-b1 PE = 2 SV = 1 - [A8DUK4_MOUSE] | 6.447007246 | 6.964298502 | 6.938126292 |
| Carboxylesterase 1D OS = *Mus musculus* GN = Ces1d PE = 1 SV = 1 - [CES1D_MOUSE] | 5.527869285 | 5.634653635 | 0 |
| Caveolin (Fragment) OS = *Mus musculus* GN = Cav1 PE = 2 SV = 2 - [D3Z148_MOUSE] | 6.495955194 | 6.212414678 | 0 |
| Chitinase-3-like protein 4 OS = *Mus musculus* GN = Chi3l4 PE = 1 SV = 2 - [CH3L4_MOUSE] | 5.78250122 | 0 | 0 |
| Collagen alpha-1(I) chain OS = *Mus musculus* GN = Col1a1 PE = 1 SV = 4 - [CO1A1_MOUSE] | 7.075805627 | 7.028473097 | 6.753210524 |
| Collagen alpha-1(III) chain OS = *Mus musculus* GN = Col3a1 PE = 2 SV = 4 - [CO3A1_MOUSE] | 6.934207535 | 7.060366511 | 7.23163175 |
| Collagen alpha-1(IV) chain OS = *Mus musculus* GN = Col4a1 PE = 2 SV = 4 - [CO4A1_MOUSE] | 7.695020525 | 7.694567589 | 7.536290851 |
| Collagen alpha-1(VI) chain OS = *Mus musculus* GN = Col6a1 PE = 2 SV = 1 - [CO6A1_MOUSE] | 6.86809465 | 6.551279889 | 6.15880609 |
| Collagen alpha-1(XII) chain OS = *Mus musculus* GN = Col12a1 PE = 4 SV = 1 - [J3KMS9_MOUSE] | 5.714611383 | 0 | 0 |
| Collagen alpha-1(XIV) chain OS = *Mus musculus* GN = Col14a1 PE = 2 SV = 1 - [B7ZNH7_MOUSE] | 6.125016434 | 0 | 0 |

TABLE 3-continued

| Protein annotation | Normalized control | Normalized T72 | Normalized T120 |
|---|---|---|---|
| Collagen alpha-2(I) chain OS = *Mus musculus* GN = Col1a2 PE = 2 SV = 2 - [CO1A2_MOUSE] | 6.543280973 | 6.813995104 | 7.023591569 |
| Collagen alpha-2(IV) chain OS = *Mus musculus* GN = Col4a2 PE = 2 SV = 4 - [CO4A2_MOUSE] | 7.550827668 | 7.530963433 | 7.33268 6213 |
| Collagen alpha-2(VI) chain OS = *Mus musculus* GN = Col6a2 PE = 2 SV = 3 - [CO6A2_MOUSE] | 6.947369979 | 6.792465562 | 6.635688357 |
| Collagen alpha-3(IV) chain OS = *Mus musculus* GN = Col4a3 PE = 1 SV = 2 - [CO4A3_MOUSE] | 7.21593568 | 7.650127224 | 7.416342179 |
| Collagenase 3 OS = *Mus musculus* GN = Mmp13 PE = 1 SV = 1 - [MMP13_MOUSE] | 7.72568074 | 7.15902446 | 7.286304725 |
| Decorin OS = *Mus musculus* GN = DSP PE = 2 SV = 1 - [PGS2_MOUSE] | 6.22520272 | 0 | 0 |
| Desmoglein-1-alpha OS = *Mus musculus* GN = Dsg1a PE = 2 SV = 2 - [DSG1A_MOUSE] | 5.548747085 | 5.852724683 | 6.62085048 |
| Desmoplakin OS = *Mus musculus* GN = Dsp PE = 2 SV = 1 - [DESP_MOUSE] | 6.162304582 | 6.382926331 | 6.992943381 |
| Dimethylaniline monooxygenase [N-oxide-forming] 2 OS = *Mus musculus* GN = Fmo2 PE = 1 SV = 3 - [FMO2_MOUSE] | 5.714661158 | 5.311917766 | 0 |
| Elongation factor 1-alpha 1 OS = *Mus musculus* GN = Eef1a1 PE = 1 SV = 3 - [EF1A1_MOUSE] | 5.598955869 | 5.764182366 | 0 |
| EMILIN-1 OS = *Mus musculus* GN = Emilin1 PE = 1 SV = 1 - [EMIL1_MOUSE] | 0 | 0 | 6.392836508 |
| Fibrillin-1 OS = *Mus musculus* GN = Fbn1 PE = 4 SV = 1 - [A2AQ53_MOUSE] | 5.877764759 | 5.704777353 | 0 |
| Fibrinogen beta chain OS = *Mus musculus* GN = Fgb PE = 2 SV = 1 - [FIBB_MOUSE] | 5.858490424 | 6.687289698 | 0 |
| Fibrinogen gamma chain OS = *Mus musculus* GN = Fgg PE = 2 SV = 1 - [FIBG_MOUSE] | 5.83914522 | 7.040881119 | 6.623714799 |
| Fibrinogen, alpha polypeptide OS = *Mus musculus* GN = Fga PE = 2 SV = 1 - [Q99K47_MOUSE] | 6.056325883 | 7.261485562 | 6.90940505 |
| Fibronectin OS = *Mus musculus* GN = Fn1 PE = 1 SV = 4 - [FINC_MOUSE] | 6.818688119 | 6.880740949 | 7.353539538 |
| Filamin, alpha (Fragment) OS = *Mus musculus* GN = Flna PE = 4 SV = 1 - [B7FAV1_MOUSE] | 7.008505708 | 6.628436178 | 6.827984047 |
| Gelsolin OS = *Mus musculus* GN = Gsn PE = 1 SV = 3 - [GELS_MOUSE] | 5.729356743 | 5.763326472 | 0 |
| Haptoglobin OS = *Mus musculus* GN = Hp PE = 1 SV = 1 - [HPT_MOUSE] | 0 | 6.109791413 | 0 |
| Hemoglobin subunit alpha OS = *Mus musculus* GN = Hba PE = 1 SV = 2 - [HBA_MOUSE] | 0 | 6.10790139 | 6.398904972 |
| Hemopexin OS = *Mus musculus* GN = Hpx PE = 1 SV = 2 - [HEMO_MOUSE] | 0 | 6.010280907 | 0 |
| Histone H2A OS = *Mus musculus* GN = Hist1h2al PE = 2 SV = 1 - [F8WIX8_MOUSE] | 7.392138835 | 6.917080096 | 7.013660548 |
| Histone H2A type 1-H OS = *Mus musculus* GN = Hist1h2ah PE = 1 SV = 3 - [H2A1H_MOUSE] | 7.392138835 | 6.926879953 | 6.857002872 |
| Histone H2B type 1-F/J/L OS = *Mus musculus* GN = Hist1h2bf PE = 1 SV = 2 - [H2B1F_MOUSE] | 7.491390907 | 7.124577253 | 7.005403699 |
| Histone H3 (Fragment) OS = *Mus musculus* GN = H3f3a PE = 2 SV = 1 - [E0CZ27_MOUSE] | 7.101484514 | 6.959792034 | 7.049922513 |
| Histone H4 OS = *Mus musculus* GN = Hist1h4a PE = 1 SV = 2 - [H4_MOUSE] | 7.676125661 | 7.580781002 | 7.458167442 |
| Ig gamma-1 chain C region secreted form OS = *Mus musculus* GN = Ighg1 PE = 1 SV = 1 - [IGHG1_MOUSE] | 5.961455553 | 0 | 0 |
| Ig kappa chain V-II region 26-10 OS = *Mus musculus* PE = 1 SV = 1 - [KV2A7_MOUSE] | 6.419014568 | 5.836803643 | 0 |
| Ig mu chain C region secreted form OS = *Mus musculus* GN = Igh-6 PE = 1 SV = 2 - [IGHM_MOUSE] | 6.201286175 | 6.434377902 | 6.526314192 |
| Indolethylamine N-methyltransferase OS = *Mus musculus* GN = Inmt PE = 1 SV = 1 - [INMT_MOUSE] | 5.637864703 | 0 | 0 |
| Junction plakoglobin OS = *Mus musculus* GN = Jup PE = 1 SV = 3 - [PLAK_MOUSE] | 6.264791243 | 6.465410008 | 7.017601329 |
| Lactotransferrin OS = *Mus musculus* GN = Ltf PE = 2 SV = 4 - [TRFL_MOUSE] | 0 | 5.762688986 | 0 |
| Laminin subunit alpha-2 OS = *Mus musculus* GN = Lama2 PE = 2 SV = 1 - [F8VQ43_MOUSE] | 5.937766596 | 0 | 0 |
| Laminin subunit alpha-3 OS = *Mus musculus* GN = Lama3 PE = 4 SV = 1 - [E9PUR4_MOUSE] | 6.674990286 | 6.260528414 | 0 |
| Laminin subunit alpha-4 OS = *Mus musculus* GN = Lama4 PE = 1 SV = 2 - [LAMA4_MOUSE] | 6.511385176 | 6.099945813 | 0 |
| Laminin subunit alpha-5 OS = *Mus musculus* GN = Lama5 PE = 1 SV = 4 - [LAMA5_MOUSE] | 6.607315399 | 6.547091642 | 6.327053775 |
| Laminin subunit beta-1 OS = *Mus musculus* GN = Lamb1 PE = 1 SV = 3 - [LAMB1_MOUSE] | 5.951335808 | 0 | 0 |
| Laminin subunit beta-2 OS = *Mus musculus* GN = Lamb2 PE = 2 SV = 2 - [LAMB2_MOUSE] | 6.610256604 | 6.263976054 | 0 |

TABLE 3-continued

| Protein annotation | Normalized control | Normalized T72 | Normalized T120 |
|---|---|---|---|
| Laminin subunit beta-3 OS = *Mus musculus* GN = Lamb3 PE = 2 SV = 2 - [LAMB3_MOUSE] | 6.687215625 | 6.379447773 | 0 |
| Laminin subunit gamma-1 OS = *Mus musculus* GN = Lamc1 PE = 2 SV = 1 - [F8VQJ3_MOUSE] | 6.70043806 | 6.209442052 | 6.048843786 |
| Laminin subunit gamma-2 OS = *Mus musculus* GN = Lamc2 PE = 4 SV = 1 - [G5E874_MOUSE] | 6.218905096 | 6.142010192 | 0 |
| Lumican OS = *Mus musculus* GN = Lum PE = 1 SV = 2 - [LUM_MOUSE] | 6.189723414 | 0 | 0 |
| Lysozyme C-2 OS = *Mus musculus* GN = Lyz2 PE = 1 SV = 2 - [LYZ2_MOUSE] | 5.83391544 | 6.30672877 | 0 |
| MCG1050941 OS = *Mus musculus* GN = Gm5414 PE = 2 SV = 1 - [Q6IFZ8_MOUSE] | 6.899619386 | 7.13581107 | 7.369324207 |
| MCG16555 OS = *Mus musculus* GN = Vdac3-ps1 PE = 4 SV = 1 - [J3QPE8_MOUSE] | 5.516224232 | 0 | 0 |
| Microfibril-associated glycoprotein 4 OS = *Mus musculus* GN = Mfap4 PE = 1 SV = 1 - [MFAP4_MOUSE] | 6.342904739 | 6.43463342 | 0 |
| Mimecan OS = *Mus musculus* GN = Ogn PE = 2 SV = 1 - [MIME_MOUSE] | 0 | 5.701058917 | 0 |
| Myelin proteolipid protein OS = *Mus musculus* GN = Plp1 PE = 1 SV = 2 - [MYPR_MOUSE] | 6.987098666 | 6.432634236 | 6.586369313 |
| Myeloid bactenecin (F1) OS = *Mus musculus* GN = Ngp PE = 2 SV = 1 - [O08692_MOUSE] | 5.44115199 | 6.142101018 | 0 |
| Myeloperoxidase OS = *Mus musculus* GN = Mpo PE = 2 SV = 2 - [PERM_MOUSE] | 0 | 6.382761391 | 0 |
| Myosin-10 OS = *Mus musculus* GN = Myh10 PE = 1 SV = 2 - [MYH10_MOUSE] | 6.107244043 | 0 | 0 |
| Myosin-11 OS = *Mus musculus* GN = Myh11 PE = 4 SV = 1 - [E9QPE7_MOUSE] | 6.549138497 | 6.023621662 | 6.486852262 |
| Myosin-9 OS = *Mus musculus* GN = Myh9 PE = 1 SV = 4 - [MYH9_MOUSE] | 6.534077311 | 5.875775823 | 6.34610934 |
| Neurofilament heavy polypeptide OS = *Mus musculus* GN = Nefh PE = 1 SV = 3 - [NFH_MOUSE] | 6.138902554 | 6.97864523 | 6.975120413 |
| Nidogen-1 OS = *Mus musculus* GN = Nid1 PE = 1 SV = 2 - [NID1_MOUSE] | 7.128370461 | 7.113290014 | 6.730533502 |
| Nidogen-2 OS = *Mus musculus* GN = Nid2 PE = 1 SV = 2 - [NID2_MOUSE] | 6.241408448 | 5.983593362 | 0 |
| Peptidyl-prolyl cis-trans isomerase B OS = *Mus musculus* GN = Ppib PE = 2 SV = 2 - [PPIB_MOUSE] | 6.012874469 | 0 | 0 |
| Periostin OS = *Mus musculus* GN = Postn PE = 1 SV = 2 - [POSTN_MOUSE] | 6.725725241 | 6.251665549 | 6.20505634 |
| Peroxiredoxin-1 (Fragment) OS = *Mus musculus* GN = Prdx1 PE = 2 SV = 1 - [B1AXW5_MOUSE] | 5.981037111 | 5.753060397 | 6.142601977 |
| Phosphate carrier protein, mitochondrial OS = *Mus musculus* GN = Slc25a3 PE = 1 SV = 1 - [MPCP_MOUSE] | 5.91683531 | 0 | 0 |
| Platelet glycoprotein 4 OS = *Mus musculus* GN = Cd36 PE = 1 SV = 2 - [CD36_MOUSE] | 6.16384265 | 5.950272926 | 0 |
| Polyubiquitin-C (Fragment) OS = *Mus musculus* GN = Ubc PE = 2 SV = 1 - [E9Q5F6_MOUSE] | 6.968911307 | 6.84889605 | 6.756181153 |
| Prelamin-A/C OS = *Mus musculus* GN = Lmna PE = 1 SV = 2 - [LMNA_MOUSE] | 5.749092722 | 0 | 0 |
| Protein 4732456N10Rik OS = *Mus musculus* GN = 4732456N10Rik PE = 3 SV = 1 - [E9Q1Z0_MOUSE] | 7.2526558 | 7.399852941 | 7.726082657 |
| Protein Col4a5 (Fragment) OS = *Mus musculus* GN = Col4a5 PE = 4 SV = 1 - [F7CK55_MOUSE] | 7.141558716 | 7.11299109 | 7.245885041 |
| Protein Col4a6 OS = *Mus musculus* GN = Col4a6 PE = 2 SV = 1 - [B1AVK5_MOUSE] | 6.667663539 | 7.041405713 | 0 |
| Protein Col6a3 OS = *Mus musculus* GN = Col6a3 PE = 4 SV = 1 - [J3QQ16_MOUSE] | 7.182772976 | 6.887860833 | 6.651938048 |
| Protein Krt78 OS = *Mus musculus* GN = Krt78 PE = 2 SV = 1 - [E9Q0F0_MOUSE] | 7.991649161 | 8.184126545 | 8.640017022 |
| Protein-glutamine gamma-glutamyltransferase 2 OS = *Mus musculus* GN = Tgm2 PE = 1 SV = 4 - [TGM2_MOUSE] | 6.606623968 | 6.34960286 | 6.828607255 |
| Serotransferrin OS = *Mus musculus* GN = Tf PE = 1 SV = 1 - [TRFE_MOUSE] | 5.569903604 | 5.983104216 | 0 |
| Serum albumin OS = *Mus musculus* GN = Alb PE = 1 SV = 3 - [ALBU_MOUSE] | 6.769856217 | 7.211712096 | 6.555648421 |
| Spectrin alpha chain, non-erythrocytic 1 OS = *Mus musculus* GN = Sptan1 PE = 2 SV = 1 - [A3KGU5_MOUSE] | 6.273962184 | 0 | 0 |
| Spectrin beta chain, non-erythrocytic 1 OS = *Mus musculus* GN = Sptbn1 PE = 1 SV = 2 - [SPTB2_MOUSE] | 5.993515702 | 0 | 0 |
| Tenascin GRCm38.p3 [GCF_000001635.23] | 7.12532211 | 6.112490357 | 6.730512501 |
| Titin OS = *Mus musculus* GN = Ttn PE = 2 SV = 1 - [E9Q8K5_MOUSE] | 5.743291257 | 6.295132427 | 0 |
| Tubulin alpha-1C chain OS = *Mus musculus* GN = Tuba1c PE = 1 SV = 1 - [TBA1C_MOUSE] | 6.33172549 | 5.982744883 | 6.399140301 |
| Tubulointerstitial nephritis antigen-like OS = *Mus musculus* GN = Tinagl1 PE = 2 SV = 1 - [H3BJ97_MOUSE] | 5.831458484 | 0 | 0 |

TABLE 3-continued

| Protein annotation | Normalized control | Normalized T72 | Normalized T120 |
|---|---|---|---|
| Voltage-dependent anion- selective channel protein 1 OS = *Mus musculus* GN = Vdac1 PE = 1 SV = 3 - [VDAC1_MOUSE] | 5.666833354 | 5.405315445 | 0 |
| von Willebrand factor OS = *Mus musculus* GN = Vwf PE = 1 SV = 2 - [VWF_MOUSE] | 5.757768857 | 0 | 0 |

Example 5

Figures 4A, 4B, 4C, 4D, 4E:
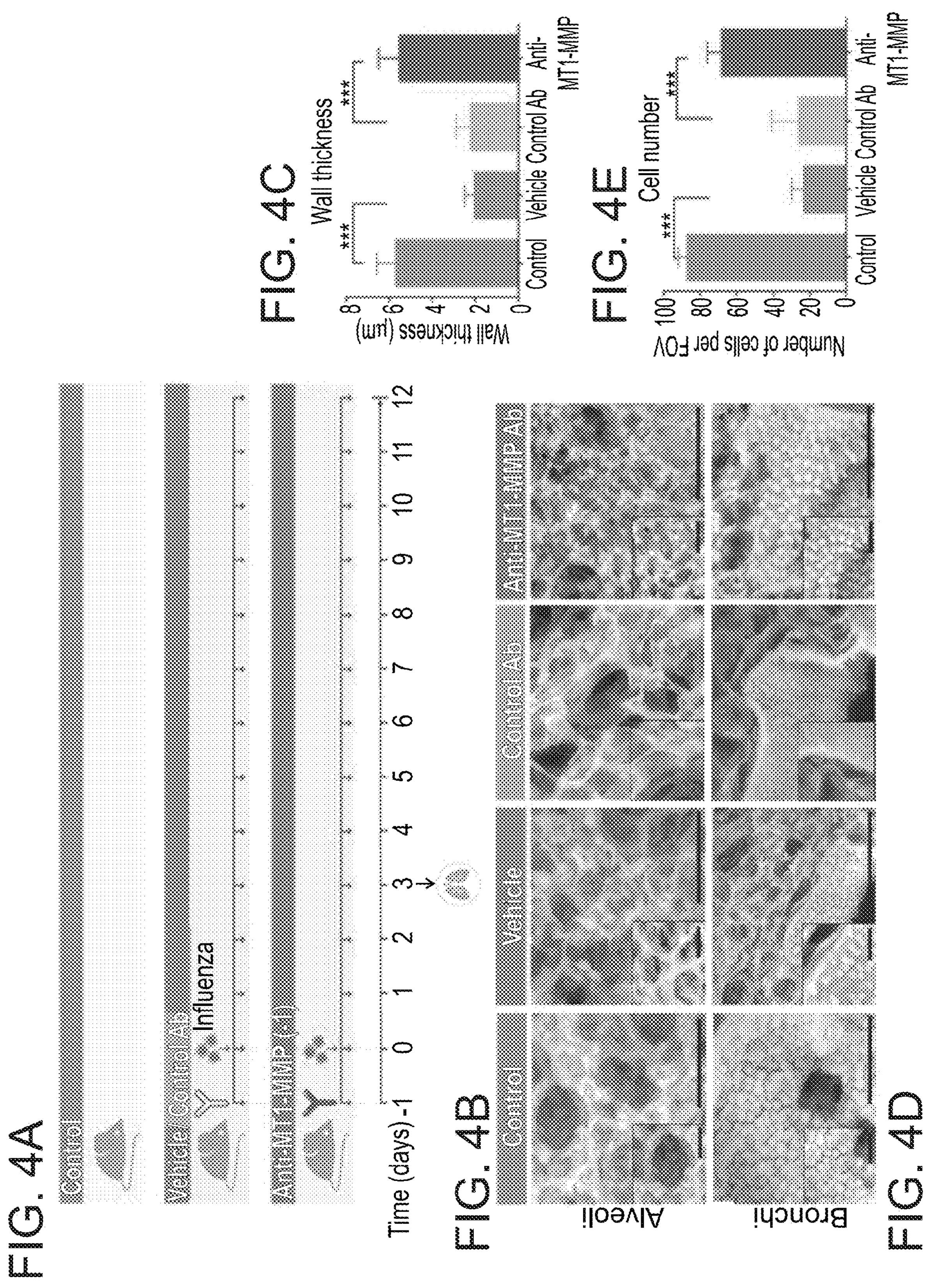
Figure 4G:
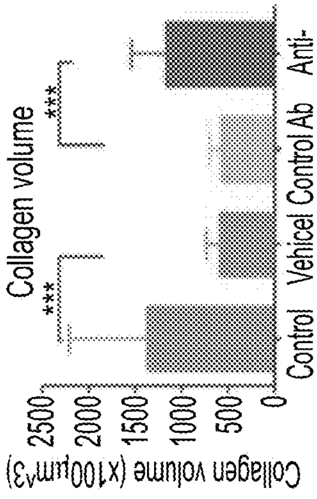
Figure 4I:
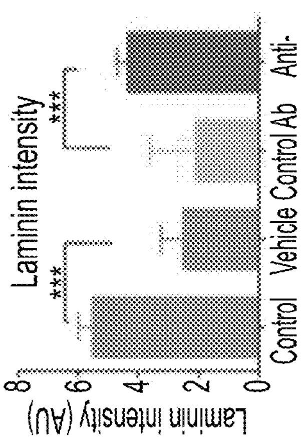
Figure 4K:
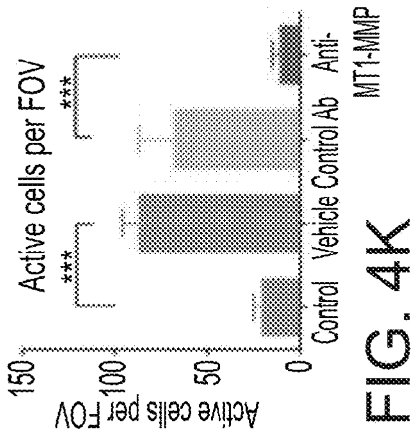
Figure 4F:
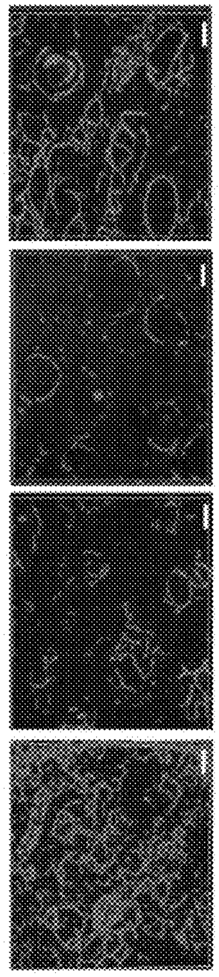
Figure 4H:
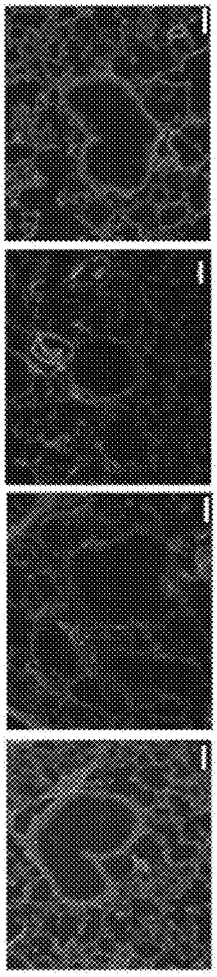
Figure 4J:
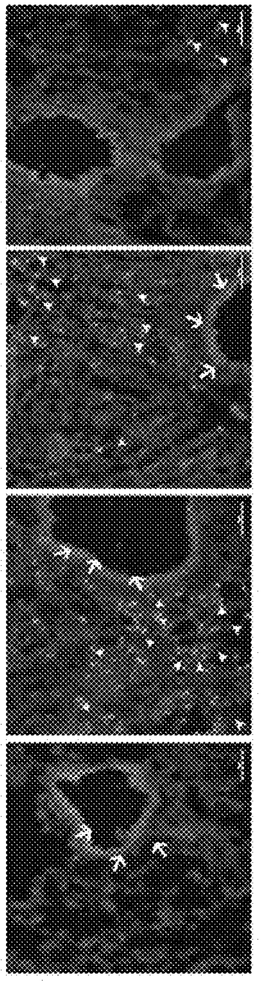

Inhibition of MTI-MMP Protects from Tissue Destruction Without Modulating the Immune Response MT1-MMP knockout mice suffer from multiple abnormalities and die within 3-5 weeks after birth (Holmbeck et al., 1999); hence, the role of MT1-MMP was evaluated using a selective allosteric inhibitory antibody of MT1-MMP (LEM 2/15) effective at nano-molar concentrations (Udi et al., 2015). Importantly, this antibody has been shown to selectively interact with MT1-MMP expressed on the cell surface and inhibit its collagenase activity without significantly interfering with proMMP-2 activation and enzyme dimerization on the cell surface (Udi et al., 2015). In order to evaluate the role of MT1-MMP during influenza infection, mice were infected with sub-lethal doses of influenza virus and treated with either vehicle (PBS), control antibody or anti-MT1-MMP antibody during the course of the disease (26, 49, 74 hours; FIGS. 4A-4K). Representative images are shown from tissue sections at 74 hours post infection in FIGS. 4A-4K. AirSEM imaging of hydrated de-cellularized tissues demonstrated that blocking MT1-MMP collagenolytic activity protected tissue integrity (both alveolar and bronchi structures), ECM morphology, and collagen structure as well as the molecular composition of ECM scaffolds (FIGS. 4B-4E). 3D analysis of two-photon microscopy in second harmonic generation showed that collagen type I fibers were more abundant and maintained a continuous alveolar sac boundaries when infected mice were treated with an anti-MT1-MMP inhibitor (FIGS. 4F-4G). Furthermore, blocking MT1-MMP proteolytic activity also protected laminin, a major basement-membrane constituent, from degradation in the infected lungs (FIGS. 4H-4J). Finally, functional in situ zymography indicated significant attenuation of proteolysis following treatment (FIGS. 4J-4K), suggesting that MT1-MMP is a major driver of tissue destruction in the infection setting.

Figure 11A:
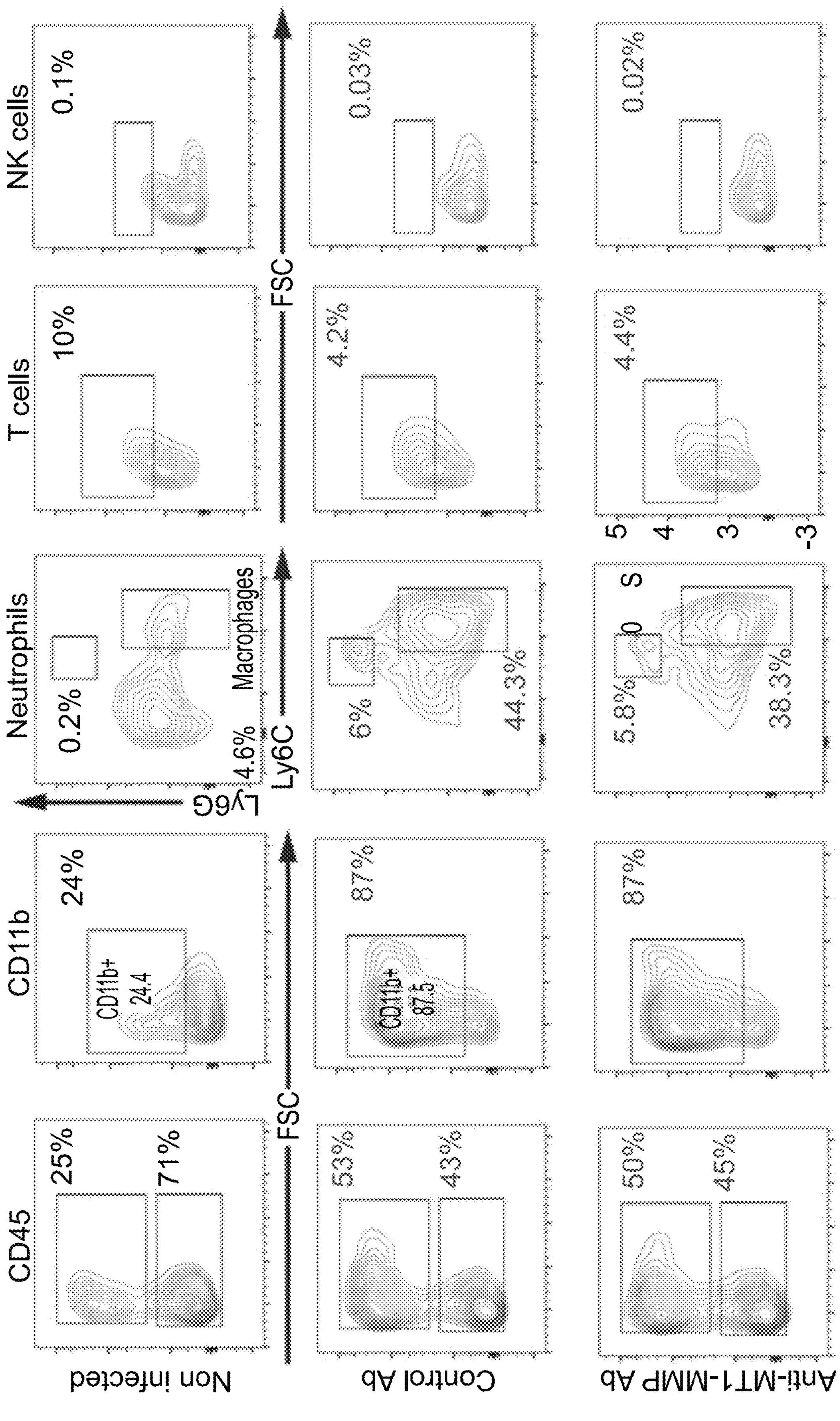
Figures 11B, 11C, 11D, 11E, 11F:
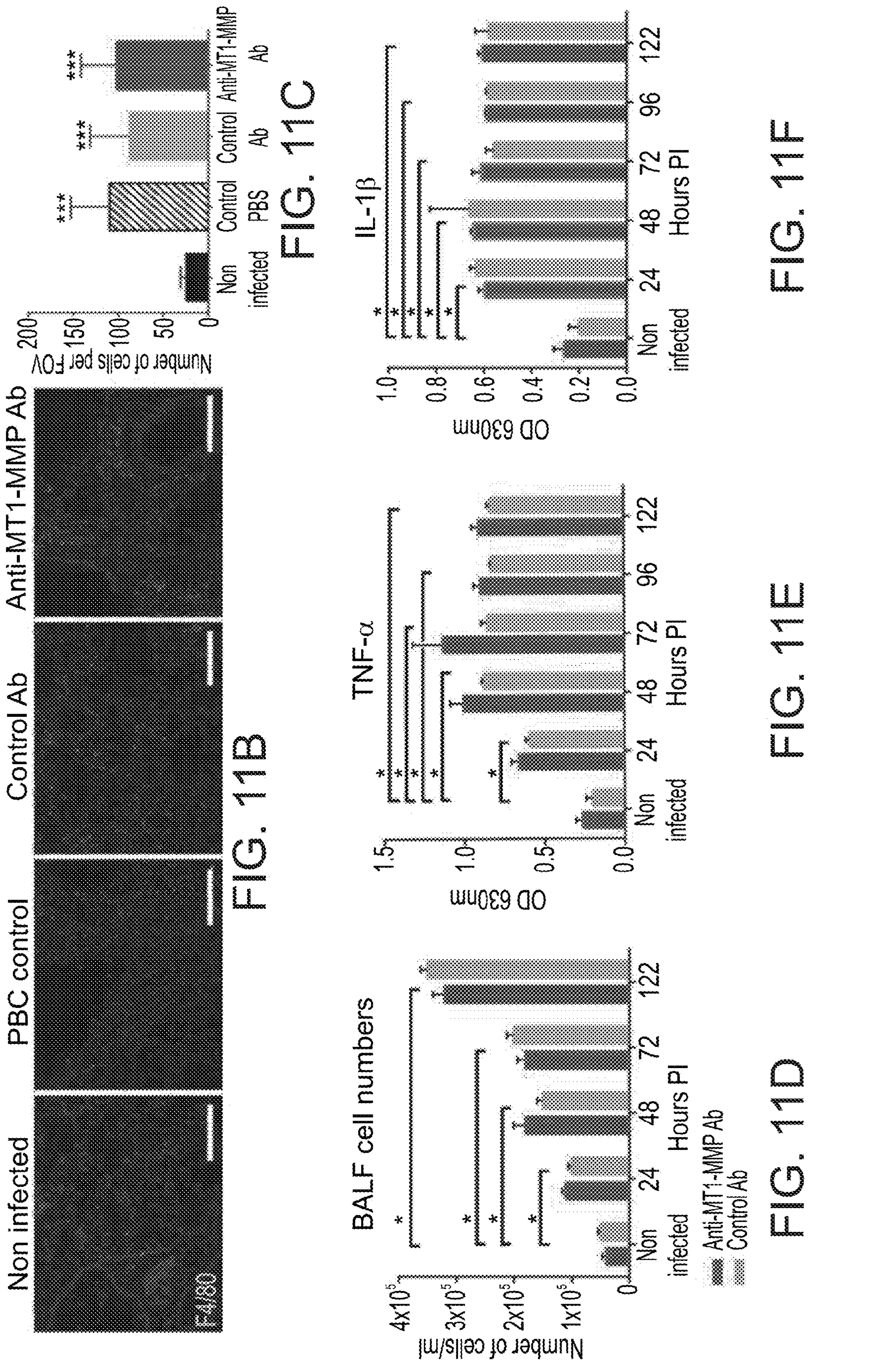

In order to better understand whether MT1-MMP is involved in immune modulation, the abundance of macrophages, neutrophils, lymphocytes and natural killer (NK) cells was analyzed at 74 hours post-infection using either anti-MT1-MMP inhibitor or a control antibody. The results show that there is enhanced recruitment of both macrophages and neutrophils to infected lungs with no detectable differences between anti-MT1-MMP and control-treated animals (FIG. 11A). In addition, in lung tissue sections stained for F4/80 marker, similar macrophage infiltration was observed upon anti-MT1-MMP treatment (FIGS. 11B-11C). Additionally, broncho-alveolar lavage fluid (BALF) was collected from both anti-MT1-MMP treated as well as control treated mice in order to evaluate cytokine level of major immune-modulating cytokines (IL-1β and TNF-α), which have been shown to play a major role in the infection process (Aldridge et al., 2009; Glaccum et al., 1997; Goldbach-Mansky and Kastner, 2009). Both IL-1β and TNF-α were strongly induced in influenza-infected mice regardless of MT1-MMP activity (FIGS. 11D-11F), suggesting the immune response was unaffected.

Figures 12A, 12B, 12C, 12D, 12E, 12F:
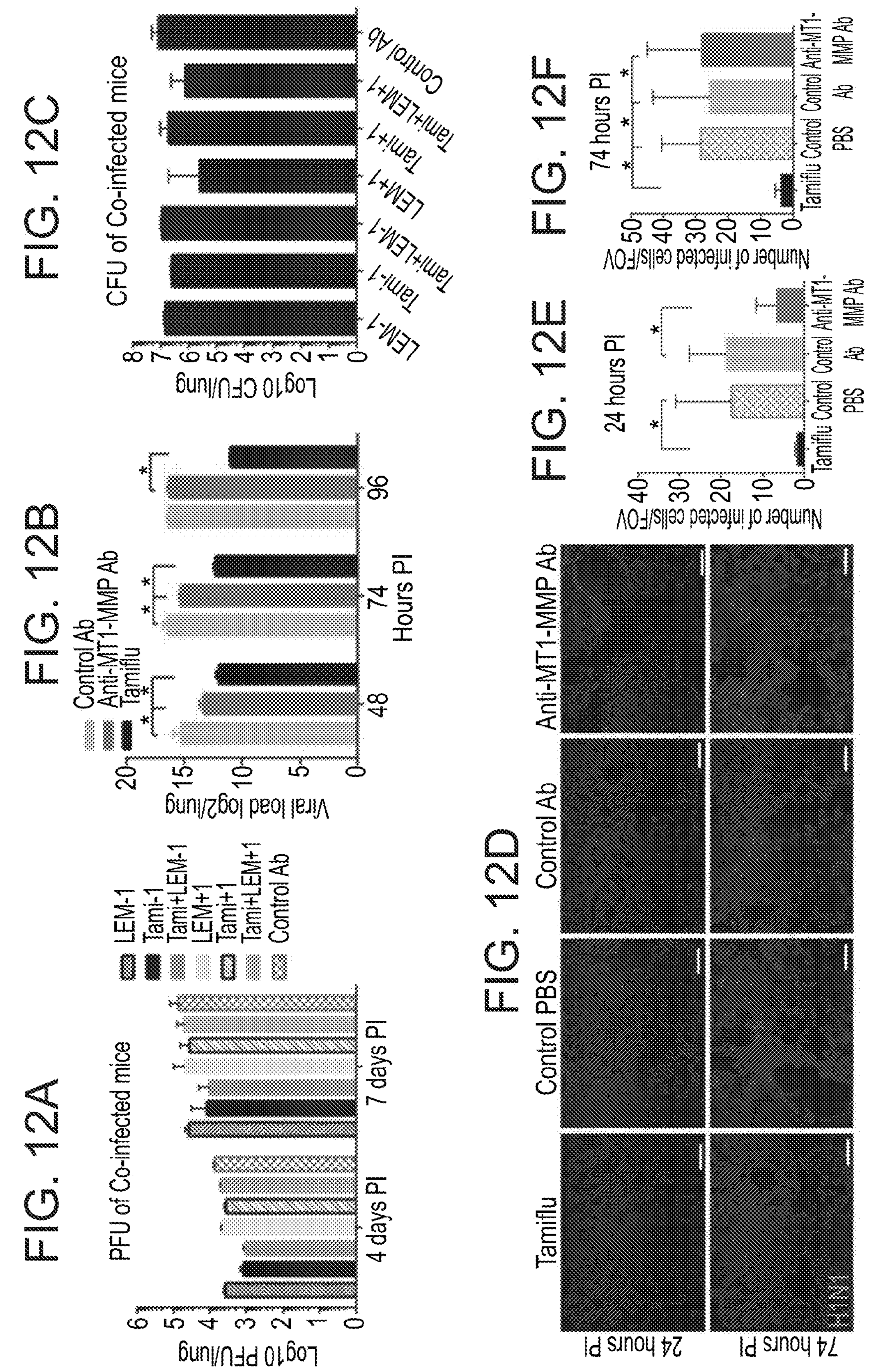

To evaluate whether MT1-MMP activity modulates viral loads during influenza infection, the plaque forming unit (PFU) assay was carried out (FIG. 12A) and also the viral RNA was quantified using PFU assay (FIG. 12B). In addition, lung tissue sections were stained for viral abundance at both 24 and 74 hours post infection (FIGS. 12D-12F). Overall, these analyses showed minimal effect of MT1-MMP inhibition on viral burden which was limited to the early phases of infection (24 hours); at later stages, no effect was discernible. These results demonstrate that MT1-MMP is not significantly involved in immune modulation or regulation of viral loads; thus, the major MT1-MMP influence on influenza infection is the massive ECM fibrillary protein degradation and tissue damage stemming from its collagenase activity.

Example 6

Figures 13A, 13B, 13C, 13D:
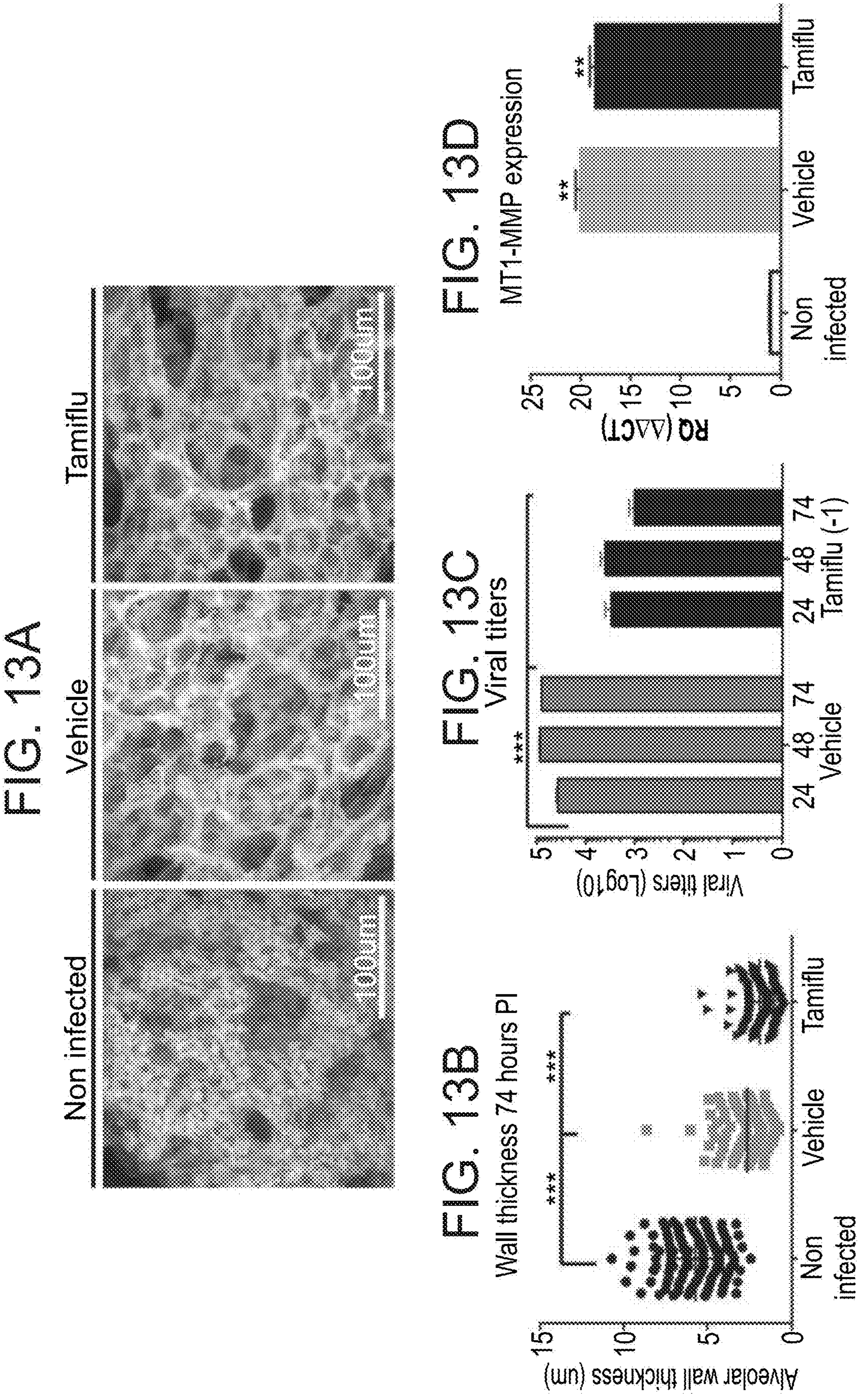

Tissue Damage Results from Host Proteolytic Activity Rather than Viral Cytopathology The present inventors then investigated whether the destructive phenotypes in the lung tissue are a direct consequence of viral cytopathology or rather a result of a host-associated immune response driving the dysregulated ECM proteolysis. The conventional influenza treatment, Oseltamivir phosphate (Tamiflu), a selective inhibitor of influenza A and B viral neuraminidase was analyzed (FIGS. 13A-13D). Virus titers from whole-lung homogenates of vehicle-treated and Tamiflu-treated mice were quantified using qPCR (FIG. 13C) and compared to topography of lung structural features visualized in lung tissue sections using AirSEM (FIGS. 9A-9B). Tamiflu dramatically reduces the viral burden (10-100 fold), meaning the tissue is exposed to low but persistent viral presence (FIG. 13C). In spite of the lower viral titers, the same destructive lung tissue and ECM phenotypes were observed, including multifocal alveolar wall thinning and a substantial loss of alveolar cells, in both vehicle-treated and Tamiflu-treated mice (FIG. 13A, 13B). Such irreversible destruction may be the main cause for loss of barrier integrity, and thus provides a window of opportunity for bacterial invasion. These results prompted the present inventors to test whether protecting ECM integrity via blocking MT1-MMP proteolysis can improve the lethal outcome of influenza-bacteria co-infections.

Example 7

Figure 5D:
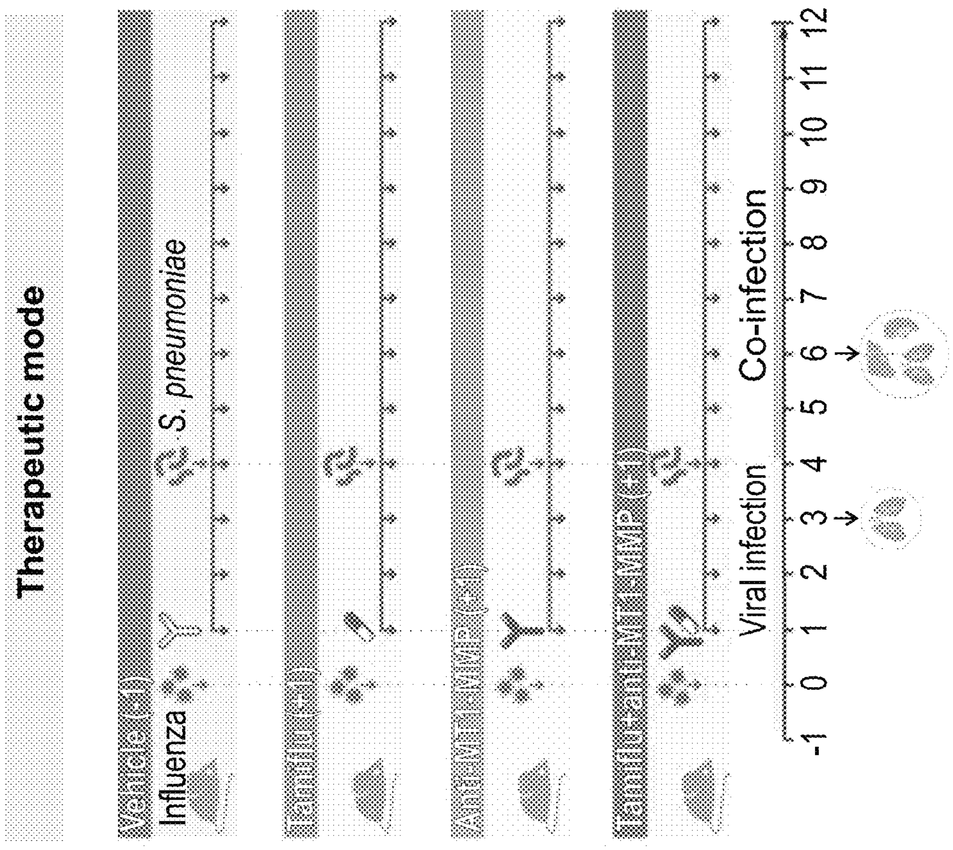
Figure 5A:
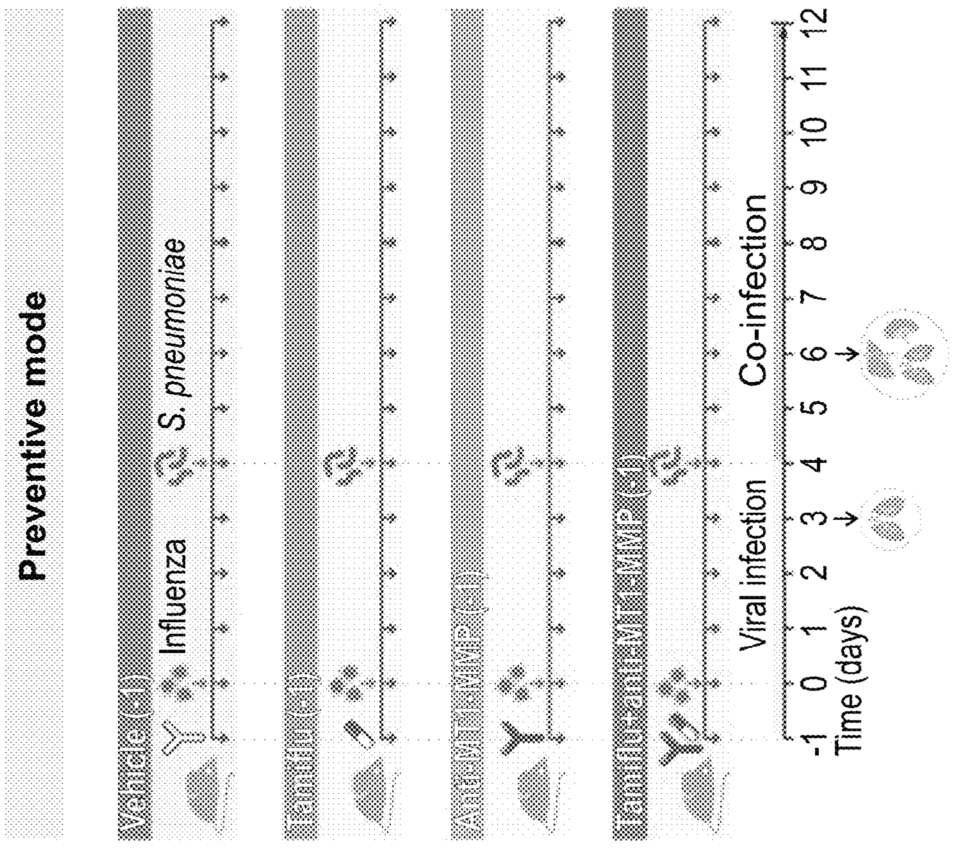
Figure 5B:
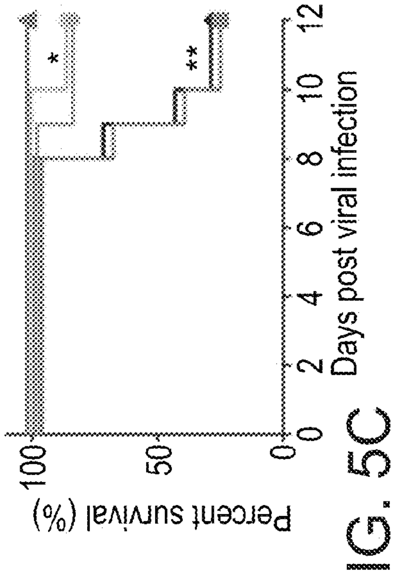

Blocking MTI-MMP in Infected Mice Promotes Tissue Maintenance and Prevents Sepsis As noted above, the viral infection of influenza results in overwhelming damage to the ECM molecular composition and lung structure even with current first-line influenza medication targeting the virus. To further support the physiological consequences of influenza-induced ECM proteolysis and to mimic the frequent conditions that endanger influenza-infected hospitalized patients, an established protocol of influenza secondary bacterial infection using *S. pneumoniae* was used (McCullers and Herman, 2001; McCullers, 2003; McCullers, 2004). 10 groups of mice (10 mice per group) were infected twice within a range of 96 hours combining PR8 influenza virus followed by *S. pneumoniae*, with both at sub-lethal doses (FIGS. 5A-5H), and the different groups were treated with either vehicle, irrelevant control antibody, Tamiflu, anti-MT1-MMP, or a combined therapy of both agents. To mimic potential treatment modes, mice were treated in two different protocols; prophylactic (before the infection) or therapeutic (post infection) (FIGS. 5A-5B). The group of mice that was treated with Tamiflu as a preventive agent (Tamiflu-1) exihibited the same survival rates and clinical scores as the group that received anti-MT1-MMP (FIGS. 5B-5C), suggesting that anti-viral or ECM protection are equally effective in preventing co-infection induced mortality when administered as a preventive treatment.

Figure 5E:
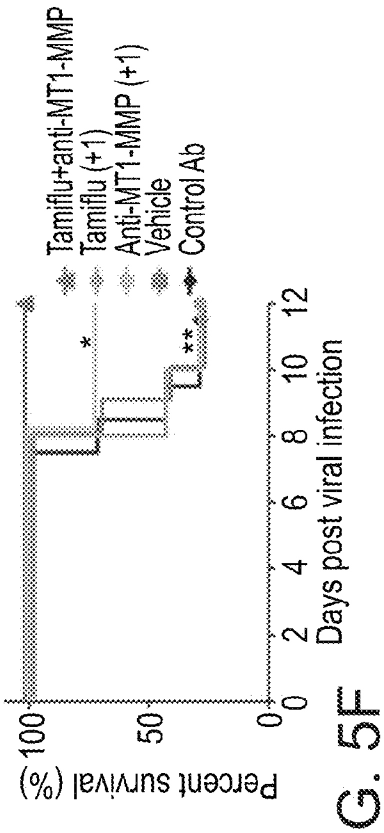
Figure 5C:
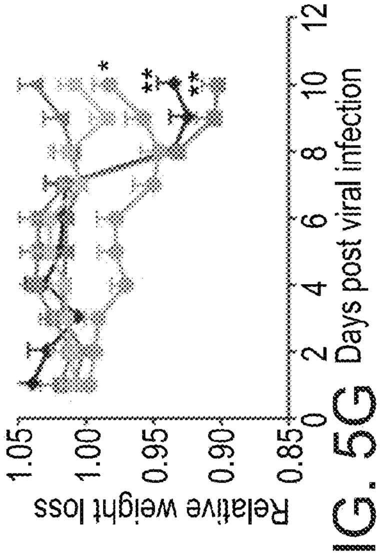
Figure 5F:
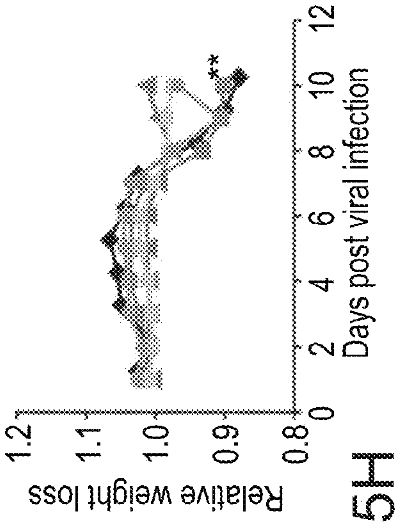
Figure 5G:
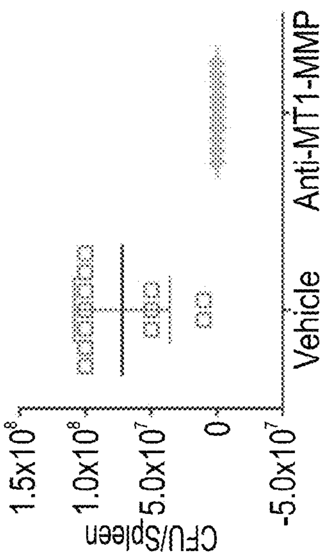
Figure 5H:
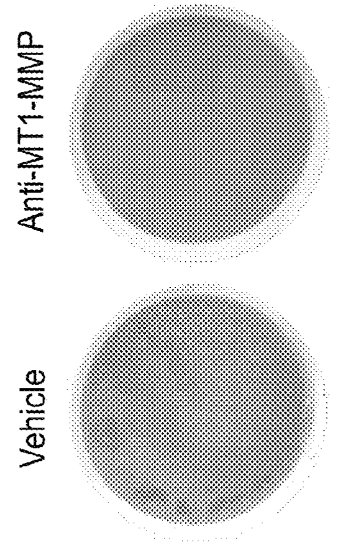

In line with reports (Jefferson et al., 2014) demonstrating that Tamiflu is not effective in reducing hospitalozation duration or influenza symptoms when administered post-infection, co-infected mice treated with Tamiflu (+1 group) did not exhibit an improved response when compared with the vehicle group (20% survival) (FIGS. 5E-5F). In these same therapeutic settings (FIG. 5D), treatment with the anti-MT1-MMP inhibitor was significantly better, indicating a pronounced theraputic effect (70% survival). Importantly, combined application of Tamiflu and anti-MT1-MMP treatment resulted in 100% survival rates when used preventatively or therapeutically (FIGS. 5B-5E). This was further supported by AirSEM images demonstrating the destructive phenotype of alveolar and bronchial structures of the Tamiflu (−1) group, which suggest that even as a prophylactic measure, Tamiflu is ineffective in preventing collateral damage in the lung ECM (FIGS. 14A-14B). To extend these observations of ECM fibrillar protein degradation, destruction of basement membrane constituents and disruption of the air-blood barrier in influenza infection, the present inventors further tested for bacterial dissemination into the blood stream (sepsis) and infections in distant organs of co-infected mice. It was found that vehicle-treated mice developed bacteremia and show dissemination of *S. pneumoniae* into the spleen 2 days post bacterial infection, while mice receiving anti-MT1-MMP inhibitor did not develop systemic bacterial dissemination and maintained a local and confined lung infection (FIGS. 5G-5H).

Discussion

The present examples suggest that therapeutic strategies to fight influenza infections should be aimed not only at the viral infectivity but also with the purpose of increasing tissue tolerance. This is especially true when taking into consideration that secondary bacterial infections involving *S. pneumoniae, Staphylococcus aureus*, and *Haemophilus influenzae* among others that are the main risk factors for reduced survival among high-risk populations (McCullers and Herman, 2001; McCullers, 2014; Morens et al., 2008). Co-infections, in many cases, involve severe lung inflammation driven by robust responses of the immune system to the viral insult. These responses dramatically impair tissue homeostasis, including disruption of the respiratory epithelium, ECM and basement membrane elements. The host response to viral infections includes tissue damage associated with oxidative stress (Avissar et al., 1996; Bozinovski et al., 2012; Campbell et al., 1987; Suliman et al., 2001; Yatmaz et al., 2013). On the one hand, MMP activity is required for the normal immune response to infection. On the other hand, host-derived MMPs may also cause infection-related immunopathology. This paradox results from the delicate balance between normal MMP function and destructive MMP-related host tissue damage (Elkington et al., 2005). Since MMPs play a crucial role in irreversible remodeling of the ECM, these robust proteases are tightly controlled and regulated (Gaffney J, 2015; Lopez-Otin and Matrisian, 2007; Turk, 2006). Moreover, maintaining tissue homeostasis during infection can be challenging when immune cells expressing active proteases are recruited towards respiratory pathogens.

Using genome-wide transcriptional profiling of influenza infected lungs, an extraordinarily large number of genes engaged in extracellular matrix turnover and protein catabolism were observed at various time points during the infection course. Previous studies have assessed the transcriptional signatures during influenza infection by comparing in vitro host responses to different influenza viral strains using human respiratory bronchial and epithelial cell lines as well as in vivo experiments in mice and ferrets (Bortz et al., 2011; Brandes M, 2013; Chevrier et al., 2011; Elkington et al., 2005; Hartmann et al., 2015; Josset et al., 2014; Kash et al., 2004; Leon et al., 2013; Ljungberg et al., 2012; Peng et al., 2014; Shapira et al., 2009). To evaluate the relevance of MT1-MMP to human infections, data from primary human bronchial epithelial cells infected in vitro with a H1N1 influenza strain A/PR/8/34 was analyzed. While human macrophages would be a better model, this data show that MT1-MMP is up-regulated also in a primary human cell model (FIG. 15) (Shapira et al., 2009) suggesting the relevance of our findings to the human ECM remodeling response to influenza infection.

Expanding on these studies, the present inventors focused a systematic analysis on ECM remodeling and, specifically, the activity of MT1-MMP during influenza infection. Noticeably, it was found that MT1-MMP is expressed almost entirely by stromal cells in the healthy lung during homeostasis. In contrast, following infection, MT1-MMP expression is primarily observed in the immune compartment and was accompanied by increased collagenolytic activity. Analysis of MT1-MMP-expressing cell populations showed a robust relationship with cytokine, chemokines and anti-viral response genes confirming that MT1-MMP is an inherent circuit of the host anti-viral response program. It was also found that multiple known substrates of MT1-MMP (Koziol Al, 2012; Stegemann et al., 2013), including fibrillary and basement membrane collagens (colIV, colXII, colXIV) as well as proteoglycans, are irreversibly cleaved and lost from the lungs of influenza-infected mice. These compositional changes were accompanied by ECM scaffold degradation and depletion of epithelial cells, thus contributing to a destructive phenotype that included loss of alveolar space, thinning of the alveolar wall and distortion of airway structures. Together, it has been shown that influenza infections induce expression and activity of MT1-MMP, which contributes to uncontrolled degradation of the structural ECM components that are required for maintaining the lung integrity and function.

Elevated MT1-MMP expression levels have been described in the context of cancer cell metastasis implicating MT1-MMP as an invasive marker associated with advanced stages and poor prognosis (Zarrabi et al., 2011). This property was attributed to the collagenolytic activity of MT1-MMP, degrading the peri-cellular environment and endothelial barriers to make a path for metastatic cells. However, the role of MT1-MMP in influenza infection has not been previously reported. Accordingly, elevated expression levels of tissue inhibitors of metalloproteinases (TIMPs), such as TIMP-1 and TIMP-3, the endogenous inhibitors of most metalloproteinases were noted. Nevertheless, expression levels of TIMP-2 the endogenous inhibitor of MT1-MMP were not significantly changed. Other ECM enzymes have been shown to play a role in influenza infection as well (Bradley et al., 2012). A significant increase in MMP-8 at the protein level was also noted (FIGS. 6A-6D).

Previous studies have sought to disentangle viral cytopathic effects from inflammatory collateral damage during influenza infection (Boon et al., 2011; Kash et al., 2004; Kobasa et al., 2007; Tate et al., 2009). It has now been shown that even in low viral titers, lung ECM destruction is significant. This suggests that the main damage to the ECM during infection is a parallel pathway driven by proteolytic events associated with host response irrespective of direct viral loads (Jamieson et al., 2013; Medzhitov et al., 2012; Schneider and Ayres, 2008). Under these conditions, it has now been shown that ECM damage can be almost completely rescued by selectively modulating MT1-MMP proteolytic activity. Using an anti-MT1-MMP inhibitory Fab fragment, it was possible to maintain tissue structure and improve the outcome of influenza infections irrespective of viral replication. It is noteworthy that this MT1-MMP antibody is highly selective in targeting the collagenase activity and does not interfere with enzyme dimerization and maturation of pro-MMP-2 required for tissue homeostasis (Udi et al., 2015). The present study shows that MT1-MMP is not critically involved in immune cell recruitment or IL-1β and TNF-α production. This is in line with previous studies showing that macrophage-derived MT1-MMP regulated subjacent cellular proteolysis rather than directly being involved in migration or cell trafficking through host tissues (Shimizu-Hirota et al., 2012).

In order to mimic the natural disease progression, co-infection settings of influenza and *S. pneumoniae* were used to show that targeting the virus with Tamiflu alone is ineffective in controlling ECM damage and does not predict successful management of the disease following bacterial infection. Importantly, inhibition of MT1-MMP activity, which protected tissue architecture and composition without significantly affecting the viral loads, exhibited improved disease management when administrated as either a prophylactic or therapeutic agent. In agreement, mice treated with Tamiflu developed sepsis due to dissemination of bacteria from the lungs to the systemic circulation, while those treated with the MT1-MMP inhibitory antibody exhibited reduced spread of bacteria through blood-air disruption. This further suggests that the maintenance of tissue homeostasis is a parallel process that, at least in our influenza model, is as important therapeutically as controlling the viral load. Importantly, the combination of the two treatments achieved complete survival rates both in the prophylactic and therapeutic modes. This further supports the present findings that the combination of the two strategies, targeting viral replication as well as maintaining host barrier homeostasis and preventing tissue destruction, greatly increases the survival outcome.

REFERENCES

Achdout, H., Arnon, T. I., Markel, G., Gonen-Gross, T., Katz, G., Lieberman, N., Gazit, R., Joseph, A., Kedar, E., and Mandelboim, O. (2003). Enhanced recognition of human NK receptors after influenza virus infection. J Immunol 171, 915-923.

Aldridge, J. R., Jr., Moseley, C. E., Boltz, D. A., Negovetich, N. J., Reynolds, C., Franks, J., Brown, S. A., Doherty, P. C., Webster, R. G., and Thomas, P. G. (2009). TNF/iNOS-producing dendritic cells are the necessary evil of lethal influenza virus infection. Proc Natl Acad Sci USA 106, 5306-5311.

Allen, I. C., Scull, M. A., Moore, C. B., Holl, E. K., McElvania-TeKippe, E., Taxman, D. J., Guthrie, E. H., Pickles, R. J., and Ting, J. P. (2009). The NLRP3 inflammasome mediates in vivo innate immunity to influenza A virus through recognition of viral RNA. Immunity 30, 556-565.

Altboum, Z., Steuerman, Y., David, E., Barnett-Itzhaki, Z., Valadarsky, L., Keren-Shaul, H., Meningher, T., Mendelson, E., Mandelboim, M., Gat-Viks, I., et al. (2014). Digital cell quantification identifies global immune cell dynamics during influenza infection. Molecular systems biology 10, 720.

Avissar, N., Finkelstein, J. N., Horowitz, S., Willey, J. C., Coy, E., Frampton, M. W., Watkins, R. H., Khullar, P., Xu, Y. L., and Cohen, H. J. (1996). Extracellular glutathione peroxidase in human lung epithelial lining fluid and in lung cells. The American journal of physiology 270, L173-182.

Boon, A. C., Finkelstein, D., Zheng, M., Liao, G., Allard, J., Klumpp, K., Webster, R., Peltz, G., and Webby, R. J. (2011). H5N1 influenza virus pathogenesis in genetically diverse mice is mediated at the level of viral load. mBio 2.

Bortz, E., Westera, L., Maamary, J., Steel, J., Albrecht, R. A., Manicassamy, B., Chase, G., Martinez-Sobrido, L., Schwemmle, M., and Garcia-Sastre, A. (2011). Host- and strain-specific regulation of influenza virus polymerase activity by interacting cellular proteins. mBio 2.

Bozinovski, S., Seow, H. J., Crack, P. J., Anderson, G. P., and Vlahos, R. (2012). Glutathione peroxidase-1 primes pro-inflammatory cytokine production after LPS challenge in vivo. PloS one 7, e33172.

Bradley, L. M., Douglass, M. F., Chatterjee, D., Akira, S., and Baaten, B. J. (2012). Matrix metalloprotease 9 mediates neutrophil migration into the airways in response to influenza virus-induced toll-like receptor signaling. PLoS pathogens 8, e1002641.

Brandes M, K. F., Kuchen S, Germain RN. (2013). A systems analysis identifies a feedforward inflammatory circuit leading to lethal influenza infection. Cell 3, 197-212.

Brandes, M., Klauschen, F., Kuchen, S., and Germain, R. N. (2013). A systems analysis identifies a feedforward inflammatory circuit leading to lethal influenza infection. Cell 154, 197-212.

Campbell, E. J., Senior, R. M., and Welgus, H. G. (1987). Extracellular matrix injury during lung inflammation. Chest 92, 161-167.

Chevrier, N., Mertins, P., Artyomov, M. N., Shalek, A. K., lannacone, M., Ciaccio, M. F., Gat-Viks, I., Tonti, E., DeGrace, M. M., Clauser, K. R., et al. (2011). Systematic discovery of TLR signaling components delineates viral-sensing circuits. Cell 147, 853-867.

Elkington, P. T., O'Kane, C. M., and Friedland, J. S. (2005). The paradox of matrix metalloproteinases in infectious disease. Clinical and experimental immunology 142, 12-20.

Gaffney J, S. I., Zehorai E, Sagi I (2015). Multilevel regulation of matrix metalloproteinases in tissue homeostasis indicates their molecular specificity in vivo (Honoken, N.J.: John Wiley & Sons, Inc).

Genis, L., Galvez, B. G., Gonzalo, P., and Arroyo, A. G. (2006). MT1-MMP: Universal or particular player in angiogenesis? Cancer Metast Rev 25, 77-86.

Glaccum, M. B., Stocking, K. L., Charrier, K., Smith, J. L., Willis, C. R., Maliszewski, C., Livingston, D. J., Peschon, J. J., and Morrissey, P. J. (1997). Phenotypic and functional characterization of mice that lack the type I receptor for IL-1. J Immunol 159, 3364-3371.

Goldbach-Mansky, R., and Kastner, D. L. (2009). Autoinflammation: the prominent role of IL-1 in monogenic autoinflammatory diseases and implications for common illnesses. The Journal of allergy and clinical immunology 124, 1141-1149; quiz 1150-1141.

Greenlee, K. J., Werb, Z., and Kheradmand, F. (2007). Matrix metalloproteinases in lung: multiple, multifarious, and multifaceted. Physiological reviews 87, 69-98.

Hartmann, B. M., Thakar, J., Albrecht, R. A., Avey, S., Zaslaysky, E., Marjanovic, N., Chikina, M., Fribourg, M., Hayot, F., Schmolke, M., et al. (2015). Human Dendritic Cell Response Signatures Distinguish 1918, Pandemic, and Seasonal H1N1 Influenza Viruses. Journal of virology 89, 10190-10205.

Hindiyeh, M., Levy, V., Azar, R., Varsano, N., Regev, L., Shalev, Y., Grossman, Z., and Mendelson, E. (2005). Evaluation of a multiplex real-time reverse transcriptase PCR assay for detection and differentiation of influenza viruses A and B during the 2001-2002 influenza season in Israel. Journal of clinical microbiology 43, 589-595.

Holmbeck, K., Bianco, P., Caterina, J., Yamada, S., Kromer, M., Kuznetsov, S. A., Mankani, M., Robey, P. G., Poole, A. R., Pidoux, I., et al. (1999). MT1-MMP-deficient mice develop dwarfism, osteopenia, arthritis, and connective tissue disease due to inadequate collagen turnover. Cell 99, 81-92.

Jaitin, D. A., Kenigsberg, E., Keren-Shaul, H., Elefant, N., Paul, F., Zaretsky, I., Mildner, A., Cohen, N., Jung, S., Tanay, A., et al. (2014). Massively parallel single-cell RNA-seq for marker-free decomposition of tissues into cell types. Science 343, 776-779.

Jamieson, A. M., Pasman, L., Yu, S., Gamradt, P., Homer, R. J., Decker, T., and Medzhitov, R. (2013). Role of tissue protection in lethal respiratory viral-bacterial coinfection. Science 340, 1230-1234.

Jefferson, T., Jones, M., Doshi, P., Spencer, E. A., Onakpoya, I., and Heneghan, C. J. (2014). Oseltamivir for influenza in adults and children: systematic review of clinical study reports and summary of regulatory comments. BMJ 348, g2545.

Josset, L., Zeng, H., Kelly, S. M., Tumpey, T. M., and Katze, M. G. (2014). Transcriptomic characterization of the novel avian-origin influenza A (H7N9) virus: specific host response and responses intermediate between avian (H5N1 and H7N7) and human (H3N2) viruses and implications for treatment options. mBio 5, e01102-01113.

Kash, J. C., Basler, C. F., Garcia-Sastre, A., Carter, V., Billharz, R., Swayne, D. E., Przygodzki, R. M., Taubenberger, J. K., Katze, M. G., and Tumpey, T. M. (2004). Global host immune response: pathogenesis and transcriptional profiling of type A influenza viruses expressing the hemagglutinin and neuraminidase genes from the 1918 pandemic virus. J Virol 78, 9499-9511.

Kobasa, D., Jones, S. M., Shinya, K., Kash, J. C., Copps, J., Ebihara, H., Hatta, Y., Kim, J. H., Halfmann, P., Hatta, M., et al. (2007). Aberrant innate immune response in lethal infection of macaques with the 1918 influenza virus. Nature 445, 319-323.

Koziol Al, M.-A. M., Clemente C, Gonzalo P, Arroyo A G. (2012). Site-specific cellular functions of MT1-MMP. Eur J Cell Biol 91, 889-895.

Koziol, A., Martin-Alonso, M., Clemente, C., Gonzalo, P., and Arroyo, A. G. (2012). Site-specific cellular functions of MT1-MMP. European journal of cell biology 91, 889-895.

Lavin, Y., Winter, D., Blecher-Gonen, R., David, E., Keren-Shaul, H., Merad, M., Jung, S., and Amit, I. (2014). Tissue-resident macrophage enhancer landscapes are shaped by the local microenvironment. Cell 159, 1312-1326.

Leon, A. J., Banner, D., Xu, L. L., Ran, L. S., Peng, Z. Y., Yi, K., Chen, C., Xu, F. P., Huang, J. R., Zhao, Z., et al. (2013). Sequencing, Annotation, and Characterization of the Influenza Ferret Infectome. Journal of virology 87, 1957-1966.

Lin, K. L., Suzuki, Y., Nakano, H., Ramsburg, E., and Gunn, M. D. (2008). CCR2+ monocyte-derived dendritic cells and exudate macrophages produce influenza-induced pulmonary immune pathology and mortality. J Immunol 180, 2562-2572.

Ljungberg, K., McBrayer, A., Camp, J. V., Chu, Y. K., Tapp, R., Noah, D. L., Grimes, S., Proctor, M. L., Liljestrom, P., Jonsson, C. B., et al. (2012). Host Gene Expression Signatures Discriminate between Ferrets Infected with Genetically Similar H1N1 Strains. PloS one 7.

Lopez-Otin, C., and Matrisian, L. M. (2007). Emerging roles of proteases in tumour suppression. Nature reviews Cancer 7, 800-808.

Lopez-Otin, C., and Overall, C. M. (2002). Protease degradomics: a new challenge for proteomics. Nature reviews Molecular cell biology 3, 509-519.

Lu, P., Takai, K., Weaver, V. M., and Werb, Z. (2011). Extracellular matrix degradation and remodeling in development and disease. Cold Spring Harb Perspect Biol 3.

McCullers, D. L., and Herman, J. P. (2001). Adrenocorticosteroid receptor blockade and excitotoxic challenge regulate adrenocorticosteroid receptor mRNA levels in hippocampus. Journal of neuroscience research 64, 277-283.

McCullers, J., Bartmess, K C (2003). Role of neuraminidase in lethal synergism between influenza virus and *Streptococcus pneumoniae*. J Infect Dis 187, 1000-1009.

McCullers, J. A. (2004). Effect of antiviral treatment on the outcome of secondary bacterial pneumonia after influenza. The Journal of infectious diseases 190, 519-526.

McCullers, J. A. (2006). Insights into the interaction between influenza virus and pneumococcus. Clinical microbiology reviews 19, 571-582.

McCullers, J. A. (2014). The co-pathogenesis of influenza viruses with bacteria in the lung. Nature reviews Microbiology 12, 252-262.

McCullers, J. A., and Rehg, J. E. (2002). Lethal synergism between influenza virus and *Streptococcus pneumoniae*: characterization of a mouse model and the role of platelet-activating factor receptor. The Journal of infectious diseases 186, 341-350.

McQuibban, G. A., Gong, J. H., Tam, E. M., McCulloch, C. A., Clark-Lewis, I., and Overall, C. M. (2000). Inflammation dampened by gelatinase A cleavage of monocyte chemoattractant protein-3. Science 289, 1202-1206.

Medzhitov, R., Schneider, D. S., and Soares, M. P. (2012). Disease tolerance as a defense strategy. Science 335, 936-941.
Morens, D. M., Taubenberger, J. K., and Fauci, A. S. (2008). Predominant role of bacterial pneumonia as a cause of death in pandemic influenza: implications for pandemic influenza preparedness. The Journal of infectious diseases 198, 962-970.
Morrison, C. J., Butler, G. S., Rodriguez, D., and Overall, C. M. (2009). Matrix metalloproteinase proteomics: substrates, targets, and therapy. Curr Opin Cell Biol 21, 645-653.
Newby, A. C. (2008). Metalloproteinase expression in monocytes and macrophages and its relationship to atherosclerotic plaque instability. Arteriosclerosis, thrombosis, and vascular biology 28, 2108-2114.
Noel, A., Gutierrez-Fernandez, A., Sounni, N. E., Behrendt, N., Maquoi, E., Lund, I. K., Cal, S., Hoyer-Hansen, G., and Lopez-Otin, C. (2012). New and paradoxical roles of matrix metalloproteinases in the tumor microenvironment. Frontiers in pharmacology 3, 140.
Ogunniyi, A. D., Giammarinaro, P., and Paton, J. C. (2002). The genes encoding virulence-associated proteins and the capsule of *Streptococcus pneumoniae* are up-regulated and differentially expressed in vivo. Microbiology 148, 2045-2053.
Overall, C. M. (2002). Molecular determinants of metalloproteinase substrate specificity: matrix metalloproteinase substrate binding domains, modules, and exosites. Mol Biotechnol 22, 51-86.
Parks, W. C., and Shapiro, S. D. (2001). Matrix metalloproteinases in lung biology. Respiratory research 2, 10-19.
Peltola, V. T., and McCullers, J. A. (2004). Respiratory viruses predisposing to bacterial infections: role of neuraminidase. The Pediatric infectious disease journal 23, S87-97.
Peng, X., Alfoldi, J., Gori, K., Eisfeld, A. J., Tyler, S. R., Tisoncik-Go, J., Brawand, D., Law, G. L., Skunca, N., Hatta, M., et al. (2014). The draft genome sequence of the ferret (*Mustela putorius* furo) facilitates study of human respiratory disease. Nat Biotechnol 32, 1250-U1114.
Read, A. F., Graham, A. L., and Raberg, L. (2008). Animal Defenses against Infectious Agents: Is Damage Control More Important Than Pathogen Control? Plos Biol 6, 2638-2641.
Schneider, D. S., and Ayres, J. S. (2008). Two ways to survive infection: what resistance and tolerance can teach us about treating infectious diseases. Nature reviews Immunology 8, 889-895.
Sela-Passwell, N., Kikkeri, R., Dym, O., Rozenberg, H., Margalit, R., Arad-Yellin, R., Eisenstein, M., Brenner, O., Shoham, T., Danon, T., et al. (2012). Antibodies targeting the catalytic zinc complex of activated matrix metalloproteinases show therapeutic potential. Nature medicine 18, 143-147.
Shapira, S. D., Gat-Viks, I., Shum, B. O., Dricot, A., de Grace, M. M., Wu, L., Gupta, P. B., Hao, T., Silver, S. J., Root, D. E., et al. (2009). A physical and regulatory map of host-influenza interactions reveals pathways in H1N1 infection. Cell 139, 1255-1267.
Shimizu-Hirota, R., Xiong, W., Baxter, B. T., Kunkel, S. L., Maillard, I., Chen, X. W., Sabeh, F., Liu, R., Li, X. Y., and Weiss, S. J. (2012). MT1-MMP regulates the PI3K delta.Mi-2/NuRD-dependent control of macrophage immune function (vol 26, pg 395, 2012). Gene Dev 26, 1122-1122.
Soares, M. P., Gozzelino, R., and Weis, S. (2014). Tissue damage control in disease tolerance. Trends in immunology 35, 483-494.
Solomonov, I., Talmi-Frank, D., Milstein, Y., Addadi, S., Aloshin, A., and Sagi, I. (2014). Introduction of correlative light and airSEM microscopy imaging for tissue research under ambient conditions. Scientific reports 4, 5987.
Stegemann, C., Didangelos, A., Barallobre-Barreiro, J., Langley, S. R., Mandal, K., Jahangiri, M., and Mayr, M. (2013). Proteomic identification of matrix metalloproteinase substrates in the human vasculature. Circulation Cardiovascular genetics 6, 106-117.
Suliman, H. B., Ryan, L. K., Bishop, L., and Folz, R. J. (2001). Prevention of influenza-induced lung injury in mice overexpressing extracellular superoxide dismutase. American journal of physiology Lung cellular and molecular physiology 280, L69-78.
Tate, M. D., Brooks, A. G., and Reading, P. C. (2011). Specific sites of N-linked glycosylation on the hemagglutinin of H1N1 subtype influenza A virus determine sensitivity to inhibitors of the innate immune system and virulence in mice. J Immunol 187, 1884-1894.
Tate, M. D., Deng, Y. M., Jones, J. E., Anderson, G. P., Brooks, A. G., and Reading, P. C. (2009). Neutrophils ameliorate lung injury and the development of severe disease during influenza infection. J Immunol 183, 7441-7450.
Taubenberger, J. K., and Morens, D. M. (2006). 1918 Influenza: the mother of all pandemics. Emerging infectious diseases 12, 15-22.
Teijaro, J. R., Walsh, K. B., Rice, S., Rosen, H., and Oldstone, M. B. (2014). Mapping the innate signaling cascade essential for cytokine storm during influenza virus infection. Proceedings of the National Academy of Sciences of the United States of America 111, 3799-3804.
Thomas, P. G., Dash, P., Aldridge, J. R., Jr., Ellebedy, A. H., Reynolds, C., Funk, A. J., Martin, W. J., Lamkanfi, M., Webby, R. J., Boyd, K. L., et al. (2009). The intracellular sensor NLRP3 mediates key innate and healing responses to influenza A virus via the regulation of caspase-1. Immunity 30, 566-575.
Tumpey, T. M., Garcia-Sastre, A., Taubenberger, J. K., Palese, P., Swayne, D. E., Pantin-Jackwood, M. J., Schultz-Cherry, S., Solorzano, A., Van Rooijen, N., Katz, J. M., et al. (2005). Pathogenicity of influenza viruses with genes from the 1918 pandemic virus: functional roles of alveolar macrophages and neutrophils in limiting virus replication and mortality in mice. Journal of virology 79, 14933-14944.
Turk, B. (2006). Targeting proteases: successes, failures and future prospects. Nature reviews Drug discovery 5, 785-799.
Udi, Y., Grossman, M., Solomonov, I., Dym, O., Rozenberg, H., Moreno, V., Cuniasse, P., Dive, V., Arroyo, A. G., and Sagi, I. (2015). Inhibition mechanism of membrane metalloprotease by an exosite-swiveling conformational antibody. Structure 23, 104-115.
Watanabe, T., Kiso, M., Fukuyama, S., Nakajima, N., Imai, M., Yamada, S., Murakami, S., Yamayoshi, S., Iwatsuki-Horimoto, K., Sakoda, Y., et al. (2013). Characterization of H7N9 influenza A viruses isolated from humans. Nature 501, 551-555.
White, M. R., Doss, M., Boland, P., Tecle, T., and Hartshorn, K. L. (2008). Innate immunity to influenza virus: implications for future therapy. Expert review of clinical immunology 4, 497-514.

Yatmaz, S., Seow, H. J., Gualano, R. C., Wong, Z. X., Stambas, J., Selemidis, S., Crack, P. J., Bozinovski, S., Anderson, G. P., and Vlahos, R. (2013). Glutathione peroxidase-1 reduces influenza A virus-induced lung inflammation. American journal of respiratory cell and molecular biology 48, 17-26.

Zarrabi, K., Dufour, A., Li, J., Kuscu, C., Pulkoski-Gross, A., Zhi, J., Hu, Y., Sampson, N. S., Zucker, S., and Cao, J. (2011). Inhibition of matrix metalloproteinase 14 (MMP -14)-mediated cancer cell migration. The Journal of biological chemistry 286, 33167-33177.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A method of treating a respiratory viral infection in a subject in need thereof comprising administering to the subject a therapeutically effective amount of an agent which down-regulates an extracellular matrix-associated polypeptide wherein said extracellular matrix-associated polypeptide is MT1-MMP1, thereby treating the respiratory viral infection.

2. The method of claim 1, wherein said agent is an antibody.

3. The method of claim 1, wherein the administering is effected no more than 2 days after the start of symptoms of the infection.

4. The method of claim 1, wherein said infection is an upper respiratory tract infection.

5. The method of claim 1, wherein said infection is a lower respiratory tract infection.

6. The method of claim 1, further comprising administering to the subject an anti-viral agent.

7. The method of claim 6, wherein said anti-viral agent is a neuraminidase inhibitor (NAI).

8. The method of claim 7, wherein said neuraminidase inhibitor is selected from the group consisting of Laninamivir, Oseltamivir, Peramivir and Zanamivir.

9. The method of claim 1, wherein said agent is an antibody that targets residues 160-173 and/or residues 218-233 of said MT1-MMP1.

10. The method of claim 1, wherein said agent is an antibody that down-regulates the collagenase activity of said MT1-MMP1.

* * * * *